United States Patent [19]
Yee et al.

[11] Patent Number: 5,455,246
[45] Date of Patent: Oct. 3, 1995

[54] PIPERIDINE DERIVATIVES

[75] Inventors: Ying K. Yee, Kennett Square, Pa.; Cyrus J. Ohnmacht; Diane A. Trainor, both of Wilmington, Del.; Joseph J. Lewis, West Chester, Pa.

[73] Assignee: Imperial Chemical Industries, plc, London, England

[21] Appl. No.: 121,117

[22] Filed: Sep. 13, 1993

Related U.S. Application Data

[62] Division of Ser. No. 926,792, Aug. 6, 1992, Pat. No. 5,266,570.

[30] Foreign Application Priority Data

Aug. 15, 1991 [GB] United Kingdom ............... 9117640
Apr. 10, 1992 [GB] United Kingdom ............... 9207966

[51] Int. Cl.$^6$ ............... A61K 31/535; A61K 31/445; A61K 31/505; C07D 413/04
[52] U.S. Cl. ............... 514/235.5; 514/256; 514/266; 514/269; 514/272; 514/275; 514/318; 514/319; 544/129; 544/277; 544/294; 546/193; 546/194; 546/195
[58] Field of Search ............... 544/129, 277, 544/294; 514/235.5, 266, 256, 269, 272, 275, 318, 319; 546/194, 195, 193

[56] References Cited

U.S. PATENT DOCUMENTS

| | | |
|---|---|---|
| 3,399,201 | 8/1968 | Schmidt et al. . |
| 3,422,106 | 1/1969 | Boissier et al. . |
| 3,455,928 | 7/1969 | Schmidt et al. . |
| 3,489,799 | 1/1970 | Schmidt et al. . |
| 3,632,653 | 1/1972 | Schmidt et al. . |
| 3,706,765 | 12/1972 | Wilhelm et al. . |
| 3,778,467 | 12/1973 | Wilhelm et al. . |
| 3,870,796 | 3/1975 | Hunger et al. . |
| 4,017,542 | 4/1977 | Wilhelm et al. . |
| 4,045,560 | 8/1977 | Sunagawa et al. . |
| 4,045,580 | 8/1977 | Wilhelm et al. . |
| 4,153,629 | 5/1979 | Tanida et al. . |
| 4,216,231 | 8/1980 | Tanida et al. . |
| 4,224,344 | 9/1980 | Sunagawa et al. . |
| 4,318,926 | 5/1982 | Schmidt-Ruppin et al. . |
| 4,358,620 | 11/1982 | Sunagawa et al. . |
| 5,266,570 | 11/1993 | Yee et al. ............... 514/237.2 |

FOREIGN PATENT DOCUMENTS

| | | |
|---|---|---|
| 610863 | 10/1961 | Belgium . |
| 843875 | 7/1975 | Belgium . |
| 918677 | 1/1973 | Canada . |
| 2556-143 | 12/1974 | Germany . |
| 2068-170 | 12/1975 | Japan . |
| 2122-358 | 4/1976 | Japan . |
| 3005-176 | 5/1976 | Japan . |
| 52-007953 | 1/1977 | Japan . |
| 69074455 | 5/1965 | Netherlands . |
| 533079 | 3/1973 | Switzerland . |

OTHER PUBLICATIONS

Sunagawa et al., "Dibenzotetracyclic Derivatives II. Synthesis of 9-Aminoalkyl-9,10-dihydro-9,10-methanoanthracenes" *Chem. Pharm. Bull.* (1979), 27, 1806–1812.

CA 119:271004c Preparation of . . . antagonists. Ohnmacht et al., p. 980, 1993.

*Primary Examiner*—Joseph K. McKane
*Attorney, Agent, or Firm*—Michael D. Alexander; Ruth H. Newtson

[57] ABSTRACT

Compounds of formula I, Ia or Ib and pharmaceutically acceptable salts thereof, useful in the treatment of neuropsychiatric disorders such as psychoses; pharmaceutical compositions comprising a compound of formula I and a pharmaceutically acceptable diluent or carrier; and methods of treating neuropschiatric disorders comprising administering to a mammal (including man) in need of such treatment an effective amount of a compound of formula I, or a pharmaceutically acceptable salt thereof.

16 Claims, No Drawings

PIPERIDINE DERIVATIVES

This application is a divisional of Ser. No. 07/926,792, filed Aug. 06, 1992 now U.S. Pat. No. 5,266,570.

This invention relates to methanoanthracene compounds useful because they have been determined to be antagonists of dopamine at $D_2$ receptors. The compounds exhibit antidopaminergic activity and are useful in alleviating neuropsychiatric disorders such as psychoses, as antipsychotics, and as neuroleptics. In addition, as $D_2$ antagonists, compounds according to the invention may also be useful in the amelioration of other disorders in which dopaminergic activity has been implicated, for example gastrointestinal disorders, emesis, and tardive dyskinesia.

According to the invention there is provided a compound of formula I, Ia, and Ib (formulae set out, together with other formulae referred to by Roman Numerals, on pages following the Examples), or a pharmaceutically acceptable salt thereof, wherein X and Y are independently selected from hydrogen, halo, and (1-6C)alkoxy;

$R^2$ is selected from

A) (1-10C)alkyl which may be substituted by hydroxy, phenyl, naphthyl, heterocyclyl attached to the adjacent carbonyl group of formula I through a ring carbon atom, phenyl(1-6C)alkyl wherein the (1-6C) alkyl moiety may bear a (1-6C)alkoxy group, heterocyclyl(1-6C)alkyl, (2-10C)alkenyl, heterocyclyl(2-6)alkenyl, heterocyclylthio(1-6C)alkyl, (3-6C)cycloalkyl, (3-6C)cycloalkyl(1-6C)alkyl wherein the alkyl moiety may bear a (1-6C)alkoxy group, (di(1-6C)alkyl)amino(1-6)alkyl, (1-6C)alkylcarbonylamino(1-6C)alkyl;

B) (1-6C)alkoxy(1-6C)alkyl wherein the alkyl or alkoxy moiety may bear a fluoromethyl, difluoromethyl, or trifluoromethyl group, (di(1-6C)alkoxy)(1-6C)alkyl wherein each alkoxy moiety may independently bear a fluoromethyl, difluoromethyl, or trifluoromethyl group, (1-6C)alkoxy(1-6C)alkoxy, (1-6C)alkoxy(1-6C)alkoxy(1-6C)alkyl, phenyloxy(1-6C)alkyl, naphthyloxy(1-6C)alkyl, heterocyclyloxy(1-6C)alkyl, heterocyclyl(1-6C)alkoxy(1-6C)alkyl, (3-6C)cycloalkyloxy(1-6C)alkyl, C) (1-6C)alkylamino, phenylamino, naphthylamino, heterocyclylamino, phenyl(1-6C)alkylamino, naphthyl(1-6C)alkylamino, heterocyclyl(1-6C)alkylamino, (3-6C)cycloalkylamino, (3-6C)cycloalkyl(1-6C)alkylamino, and heterocyclyl which is attached to the adjacent carbonyl group by a ring nitrogen;

D) (1-10C)alkoxy, (3-6C)cycloalkyloxy, (3-6C)cycloalkyl(1-6C)alkoxy, heterocyclyloxy, phenyl(1-6C)alkoxy, naphthyl(1-6C)alkoxy, and heterocyclyl(1-6C)alkoxy;

wherein said phenyl and naphthyl moieties in (A)–(D) may each bear 0–3 substituents independently selected from the group consisting of (1-6C)alkyl, (1-6C)alkoxy, hydroxy, halo, cyano, nitro, benzoyl, aminosulfonyl having the formula $SO_2NR^aR^b$ and aminocarbonyl having the formula $CONR^cR^d$ wherein $R^a$, $R^b$, $R^c$ and $R^d$ are independently selected from hydrogen and (1-6C)alkyl, or wherein $R^a$ and $R^b$, and $R^c$ and $R^d$, together with the nitrogen atom to which each is attached, form a 5-membered or 6-membered heterocyclic ring in which the said nitrogen is the only heteroatom;

and wherein, said heterocyclyl moieties are selected from the group consisting of five- and six-membered heterocyclyl radicals containing from 1–3 heteroatoms selected from nitrogen, oxygen, and sulfur, and which may bear 0–2 substituents selected from (1-6C)alkyl, (1-6C)alkoxy, chloro, and fluoro; and when a linking group intervenes between a said heterocyclyl moiety and the carbonyl group of formula I, the said heterocyclyl group is connected to the linking group by a ring carbon atom;

R' is selected from
2-pyrimidinyl, which may be substituted with from 0–2 substituents selected from halo, phenyl, amino, (1-6C)alkoxy, hydroxy, nitro, and (1-6C)alkyl,
4-pyrimidinyl, 2-pyridyl,
2-purinyl; and R" is 4-morpholinyl substituted by 0–2 substituents selected from (1-6C)alkyl.

The invention further provides a pharmaceutical composition suitable for the treatment of neuropsychiatric disorders, comprising a compound of formula I, Ia, or Ib as defined above, or a pharmaceutically acceptable salt thereof, and a pharmaceutically acceptable diluent or carrier.

The invention further provides a method of treating neuropsychiatric disorders, comprising administering to a mammal (including man) in need of such treatment an effective amount of a compound of formula I, Ia, or Ib, or a pharmaceutically acceptable salt thereof.

The groups (A), (B), (C), and (D) noted above are referred to as "Group A", "Group B", and so forth, in the discussion of syntheses subsequently presented. The piperidine side chains containing these groups generally correspond, respectively, to (A) amides, (B) oxygenated amides, (C) ureas, and (D) urethanes.

In this specification the terms "alkyl" and "alkoxy" include both straight and branched chain radicals, but it is to be understood that references to individual radicals such as "propyl" or "propoxy" embrace only the straight chain (37 normal") radical, branched chain isomers such as "isopropyl" or "isopropoxy" being referred to specifically.

The term "halo" is inclusive of fluoro, chloro, bromo, and iodo unless noted otherwise.

The term "heterocyclyl" is inclusive of heteroaryl radicals and non-aromatic ring radicals containing ring heteroatoms.

It will be appreciated by those skilled in the art that compounds of formula I may contain an asymmetrically substituted carbon and/or sulfur atom, and accordingly may exist in, and be isolated in, optically-active and racemic forms. Some compounds may exhibit polymorphism. It is to be understood that the present invention encompasses any racemic, optically-active, polymorphic or stereoisomeric form, or mixtures thereof, which form possesses properties useful in the treatment of psychoses, it being well known in the art how to prepare optically-active forms (for example, by resolution of the racemic form by recrystallization techniques, by synthesis form optically-active starting materials, by chiral synthesis, or by chromatographic separation using a chiral stationary phase) and how to determine efficacy for the treatment of psychoses by the standard tests described hereinafter.

Particular values of (1-10C)alkyl include methyl, ethyl, propyl, isopropyl, butyl, isobutyl, sec-butyl, tert-butyl, pentyl, isopentyl, neopentyl, hexyl, isohexyl, heptyl, isoheptyl, octyl, isoctyl, 2,2,4-trimethylpentyl, nonyl, isononyl, and decyl.

Particular values of (1-6C)alkyl include methyl, ethyl, propyl, isopropyl, butyl, isobutyl, sec-butyl, tert-butyl, pentyl, isopentyl, neopentyl, hexyl, and isohexyl.

Particular values of (1-10C)alkoxy include methoxy, ethoxy, propoxy, isopropoxy, butoxy, isobutoxy, sec-butoxy, tert-butoxy, pentoxy, isopentoxy, neopentoxy, hexoxy, isohexoxy, heptoxy, isoheptoxy, octoxy, isoctoxy, 2,2,4-trimethylpentoxy, nonoxy, isononoxy, and decoxy.

Particular values of (1-6C)alkoxy include methoxy, ethoxy, propoxy, isopropoxy, butoxy, isobutoxy, sec-butoxy, tert-butoxy, pentoxy, isopentoxy, neopentoxy, hexoxy, and isohexoxy.

Particular values of (2-10C)alkenyl include ethenyl, prop-1-enyl, prop-2-enyl (i.e. allyl), but-1-enyl, but-2-enyl, but-3-enyl, pent-1-enyl, pent-2-enyl, pent-3-enyl, pent-4-enyl, hex-1-enyl, hex-2-enyl, hex-3-enyl, hex-4-enyl, hex-5-enyl, hept-1-enyl, hept-3-enyl, oct-1-enyl, oct-3-enyl, oct-5-enyl, non-1-enyl, non-3-enyl, non-5-enyl, non-7-enyl, and dec-1-enyl.

Particular values of (2-6C)alkenyl include the values given above, including ethenyl, prop-1-enyl, prop-2-enyl (i.e. allyl), but-1-enyl, but-2-enyl, but-3-enyl, pent-1-enyl, pent-2-enyl, pent-3-enyl, pent-4-enyl, hex-1-enyl, hex-2-enyl, hex-3-enyl, hex-4-enyl, and hex-5-enyl.

Particular values of (3-6C)cycloalkyl include cyclopropyl, cyclobutyl, cyclopentyl, and cyclohexyl.

Particular values of five- and six-membered heterocyclyl radicals containing from 1–3 heteroatoms selected from nitrogen, oxygen, and sulfur include heteroaryl radicals such as 2-, 3-, and 4-pyridyl, 2-pyrazinyl, 2- and 4-pyrimidinyl, 3- and 4-pyridazinyl, 3-, 4- and 5-isothiazolyl, 2-, 4- and 5-oxazolyl, 2-, 4- and 5-thiazolyl, 4- and 5-oxadiazolyl, 2- and 3-furyl, 2-, 4-, and 5-imidazolyl, and 2- and 3-thienyl. The aforementioned heteroaryl radicals are understood to include the bicyclic benz-fused derivatives thereof. Also included are non-aromatic values such as 2-tetrahydrofuranyl, 3-tetrahydrofuranyl, 2-tetrahydropyranyl, 3-tetrahydropyranyl, 4-tetrahydropyranyl, 2-(1,3-dioxolanyl), 4-(1,3-dioxolanyl), 2-(1,3-dioxanyl), 4-(1,3-dioxanyl), 5-(1,3-dioxanyl), 2-(1,4-dioxanyl), 1-pyrrolidinyl, 1-piperidinyl, and 4-morpholinyl.

Particular values of 2-pyrimidinyl substituted by 0–2 substituents include 2-pyrimidinyl, 4-amino-5-fluoropyrimidin-2-yl, 5-iodopyrimidin-2-yl, 5-phenylpyrimidin-2-yl, 4-methoxypyrimidin-2-yl, 4-hydroxypyrimidin-2-yl, 5-fluoropyrimidin-2-yl, 4-amino-5-nitropyrimidin-2-yl, 4,5-diaminopyrimidin-2-yl, 4,6-dimethylpyrimidin-2-yl, and 4,6-dichloropyrimidin-2-yl.

More particular values of (1-10C)alkyl include the values of (1-6C)alkyl, including methyl, ethyl, propyl, isopropyl, butyl, isobutyl, sec-butyl, tert-butyl, pentyl, isopentyl, neopentyl, hexyl, and isohexyl.

A more particular value of (3-6C)cycloalkyl is cyclopentyl.

More particular values of (1-6C)alkyl include values of (1-3C)alkyl, including methyl, ethyl, propyl and isopropyl.

More particular values of (1-10C)alkoxy include the values of (1-6C)alkoxy, including methoxy, ethoxy, propoxy, isopropoxy, butoxy, isobutoxy, sec-butoxy, tert-butoxy, pentoxy, isopentoxy, neopentoxy, hexoxy, and isohexoxy.

More particular values of (1-6C)alkoxy include values of (1-3C)alkoxy, including methoxy, ethoxy, propoxy, and isopropoxy.

More particular values of five- and six-membered heterocyclyl radicals containing from 1–3 heteroatoms selected from nitrogen, oxygen, and sulfur include 2-, 3-, and 4-pyridyl, 3-, 4- and 5-isothiazolyl, 2-, 4- and 5-thiazolyl, 2- and 4-imidazolyl, 2-tertrahydrofuranyl, 3-tetrahydrofuranyl, 2-(1,3-dioxolanyl), 4-(1,3-dioxolanyl), 2-(1,3-dioxanyl), 4-(1,3-dioxanyl), and 2-(1,4-dioxanyl).

Preferred compounds of formula I include compounds wherein X and Y are independently selected from hydrogen and chloro; wherein $R^2$ is selected from ethyl, propyl, butyl, cyclopentylmethyl, cyclohexylmethyl, tert-butyl, methoxymethyl, 2-methoxy-2-propyl, ethoxymethyl, isopropoxymethyl, cyclopentoxymethyl, 1-methoxyethyl, 1-ethoxyethyl, (cyclopentyl)(methoxy)methyl, dimethoxymethyl, diethoxymethyl, benzyl, phenylethyl, 2-pyridylmethyl, 2-pyridylmethoxy, 4-tetrahydropyranyloxymethyl, and 2,2,2-trifluoroethoxymethyl; R' is 2-pyrimidinyl; and R" is selected from trans-2,6-dimethyl-4-morpholinyl and 4-morpholinyl.

Specifically preferred compounds include:

N-(1-[(9S,10S)-(+)-2-Chloro-9,10-dihydro-9,10-methanoanthracen-9-ylmethyl)-4-piperidyl)-2-ethoxyacetamide;

(2R)-N-(1-[2-Chloro-9,10-dihydro-9,10-methanoanthracen-9-ylmethyl]-4-piperidyl)-2-methoxypropionamide;

(2R)-N-(1-[(9S,10S)-2-Chloro-9,10-dihydro-9,10-methanoanthracen-9-yl-methyl]-4-piperidyl)-2-methoxypropionamide;

N-(1-[2-Chloro-9,10-dihydro-9,10-methanoanthracen-9-ylmethyl]-4-piperidyl)-2-(2-pyridyl)acetamide;

N-(1-[2-Chloro-9,10-dihydro-9,10-methanoanthracen-9-ylmethyl]-4-piperidyl)-2-ethoxypropionamide;

N-(1-[2-Chloro-9,10-dihydro-9,10-methanoanthracen-9-ylmethyl]-4-piperidyl)-2-(2,2,2-trifluoroethoxy)acetamide;

N-(1-[2-Chloro-9,10-dihydro-9,10-methanoanthracen-9-ylmethyl]-4-piperidyl)-2,2-dimethylpropionamide;

2-Pyridylmethyl-N-(1-[2-chloro-9,10-dihydro-9,10-methanoanthracen-9-ylmethyl]-4-piperidyl)carbamate;

1-(2-Chloro-9,10-dihydro-9,10-methanoanthracen-9-yl-methyl)-4-(trans-2,6-dimethyl-4-morpholinyl)piperidine;

1-(2-Chloro-9,10-dihydro-9,10-methanoanthracen-9-yl-methyl)-4-(4-morpholinyl)piperidine dihydrochloride;

2-[1-(9S,10S-2-Chloro-9,10-dihydro-9,10-methanoanthracen-9-yl-methyl)-4-piperidylamino]pyrimidine;

N-(1-[(9S,10S)-2-Chloro-9,10-dihydro-9,10-methanoanthracen-9-yl-methyl]-4-(piperidyl)-2,2-diethoxyacetamide hydrochloride;

N-(1-[(9S,10S)-2-Chloro-9,10-dihydro-9,10-methanoanthracen-9-yl-methyl]-4-(piperidyl)-2-(2,2,2-trifluoroethoxy)acetamide;

N-(1-[(9S,10S)-2-Chloro-9,10-dihydro-9,10-methanoanthracen-9-yl-methyl]-4-(piperidyl)-2-methoxy-2-methylpropionamide;

N-(1-[2-Chloro-9,10-dihydro-9,10-methanoanthracen-9-yl-methyl]-4-(piperidyl)-2-(4-tetrahydropyranyloxy) acetamide;

Epimer I of N-(1-[(9S,10S)-2-chloro-9,10-dihydro-9,10-methanoanthracen-9-ylmethyl]-4-(piperidyl)-2-cyclopentyl-2-methoxyacetamide hydrochloride; and Epimer II of N-(1[(9S,10S)-2-chloro-9,10-dihydro-9,10-methanoanthracen-9-ylmethyl]-4-(piperidyl)-2-ethoxypropionamide.

When X is chloro and Y is hydrogen, in general, 9S,10S stereochemistry is preferred,. In this case, stereochemistry can be determined by coupling an acid chloride of formula IV (G=chloro) with a chiral compound, such as an oxazolidinone of formula VII, to yield two diastereomers. Separation and recrystallization of the diastereomers followed by X-ray structure determination provides absolute stereochemistry at the 9 and 10 positions.

A compound of formula I can be made by processes which include processes known in the chemical arts for the production of structurally analogous compounds. Such processes for the manufacture of an amide of formula I as defined above are provided as further features of the invention together with chemical intermediates involved therein, and are illustrated by the following procedures in which the meanings of generic radicals are as given above unless otherwise qualified. Such a process can be effected, generally,:

I. for compounds having formula I (a) when R2 is selected from Group A or B, by reacting an amine of formula II with an acid of formula $R^2COOH$. The reaction may be conducted in a suitable solvent such as pyridine, at a temperature in the range of from 0° to 25° C., and in the presence of activators such as 1-(3-dimethylaminopropyl)-3-ethylcarbodiimide hydrochloride (WSCDI) and 4-dimethylaminopyridine (DMAP).

(b) when R2 is selected from Group A or B, by reacting an amine of formula II with an acid halide of formula $R^2COZ$, wherein Z is a halo group, for example chloro or bromo. The reaction may be conducted in a suitable solvent such as pyridine, at a temperature in the range of from 0° to 25° C., and in the presence of a suitable catalyst (for example, DMAP). For processes (a) and (b), when $R^2$=(1-6C)alkoxy(1-6C)alkyl is desired, for example, the $R^2$ portion of the acid $R^2COOH$ or acid chloride $R^2COCl$ is a corresponding (1-6C)alkoxy(1-6C)alkyl moiety. Other desired $R^2$ moieties correspond similarly.

(c) when $R^2$ is alkoxymethyl (Group B), by reacting a compound of formula III (Z is as defined above) with an alcohol of formula $R^2OH$ in the presence of an alkali metal hydride (for example sodium hydride) and at a temperature in the range of from 0° to 80° C. The reaction may be conducted in a suitable solvent such as DMF or THF.

(d) when $R^2$ is alkoxymethyl (Group B), by reacting a compound of formula III with an alcohol of formula $R^2OH$ in the presence of an alkali metal hydride (for example sodium hydride) and silver tetrafluoroborate. The reaction may be conducted in a suitable solvent such as DMF or THF at a temperature in the range of from 0° to 25° C.

(e) when R2 is selected from Group C, by reacting a compound of formula II with an isocyanate of formula $R^2NCO$. The reaction may be conducted in a suitable solvent such as methylene chloride and at a temperature in the range of from 0° to 40° C.

(f) when R2 is selected from Group C, by reacting an isocyanate of formula IV with an amine of formula $R^2NH_2$. The reaction may be conducted in a suitable solvent such as methylene chloride and at a temperature in the range of from 0° to 40° C.

(g) when $R^2$ is selected from Group C, by reacting an imidazole of formula V with an amine of formula $R^2NH_2$. The reaction may be conducted in a suitable solvent such as THF and at a temperature in the range of from 0° to 70° C.

(h) when $R^2$ is selected from Group D, by reacting a compound of formula IV with a compound of formula $R^2OH$. The reaction may be conducted in a suitable solvent such as THF and at a temperature in the range of from 0° to 70° C., and in the presence of a catalyst such as DMAP.

(i) when $R^2$ is selected from Group D, by reacting an imidazole of formula V with an alcohol of formula $R^2OH$. The reaction may be conducted in a suitable solvent such as THF and at a temperature in the range of from 0° to 70° C.

(j) when $R^2$ is selected from Group D, by reacting an amine of formula II with a chloroformate of formula $R^2OCOCl$ wherein the value corresponding to $R^2$ is (1-10C)alkoxy. The reaction may be conducted in a suitable solvent such as THF and at a temperature in the range of from −78° to 25° C.;

II. for compounds having formula Ia (a) by treating a compound of formula II with a corresponding compound having the formula R'Cl or R'Br in the presence of a base such as triethylamine, for example by treating a corresponding compound of formula II with a corresponding 2-chloropyrimidine if a corresponding pyrimidin-2-yl is desired as R'. The reaction can be conducted in a solvent such as N-methyl pyrrolidone and at a temperature of 25° to 100° C.

(b) when R' is 2-pyridyl, by reacting a corresponding compound of formula II with 2-fluoropyridine in the presence of potassium fluoride. The reaction can be conducted in a solvent such as N-methylpyrrolidone and at a temperature of 25° to 150° C.

(c) by treating a compound of formula VI wherein G is hydrogen with a corresponding piperidine of formula VIII. The reaction can be conducted with a reducing agent such as sodium cyanoborohydride and in a solvent such as a lower alcohol (e.g., methanol) and at a temperature of 25° C.;

(d) when R' is 2-purinyl, by treating a compound of formula Ia wherein R' is 4,5-diaminopyrimidin-2-yl with formic acid at a temperature of 25° to 210° C.

III. for compounds having formula Ib where R" is a morpholinyl group, by treating a compound of formula IX with a corresponding morpholine at a temperature of 25° to 120° C.

If not commercially available, the necessary starting materials for the procedures such as that described above may be made by procedures which are selected from standard organic chemical techniques, techniques which are analogous to the synthesis of known, structurally similar compounds, or techniques which are analogous to the above described procedure or the procedures described in the examples. In the discussion which follows and the reaction Schemes pertaining thereto, standard chemical abbreviations and acronyms have been employed, including: "THF" for tetrahydrofuran; "DMF" for dimethylformamide; "TFA" for trifluoroacetic acid; "'Bu" for tert-butyl; "RT" for room temperature; "DMSO" for dimethylsulfoxide; "Me" for methyl; and "Ph" for phenyl. The variable "Z" is employed to refer to halo substituents (such as chloro).

A common intermediate for making compounds according to the invention is an acid (G is hydroxyl) or acid halide (G is a halo group such as chloro) or aldehyde (G is hydrogen) of formula VI. This intermediate can be made as illustrated in Scheme I (set out, together with other schemes referred to herein, on pages following the Examples and formulae). An anthraquinine of formula 10 can be reduced to the corresponding anthracene of formula 12 using zinc and aqueous ammonia. Anthracene 12 can then be converted to the corresponding 9-aldehyde 14 using phosphorus oxytrichloride and N-methylformanilide. Reaction of aldehyde 14 with vinyl acetate (Diels-Alder reaction) affords the bridged compound 16 which can then be oxidized with chromium trioxide (in the presence of sulfuric acid) to the corresponding acid 18. Acid 18 can then be successively treated with thionyl chloride (in, for example, toluene) to make the corresponding 9-acid chloride, followed by sodium azide (in, for example, a mixture of water and acetone) to make the corresponding 9-acyl azide, followed by heating (in, for example, toluene) to effect rearrangement to the corresponding isocyanate, followed by treatment with an alkali metal hydroxide (in an alcohol such as ethanol) to cleave the acetyl group to hydroxy and hydrolyze the isocyanate to amino, thereby yielding the 9-amine 20. Amine 20 can then be treated with an alkali metal (for example, sodium) nitride (in, for example, acetic acid) to effect a ring contraction and thereby yield the 9-aldehyde of formula 22. Aldehyde 22 can be oxidized with chromium trioxide in the presence of sulfuric acid to yield the corresponding 9-acid of formula 24 (corresponding to the acid of formula VI, G=hydroxyl). The corresponding 9-acid chloride can be obtained by treating acid 24 with thionyl chloride.

It is noted that if a 2,7-dihalo substituted methanoanthracene is desired, it can be prepared (as, for example, illustrated in the examples of co-pending application D36501, herein incorporated by reference), starting with an (unresolved) acid 24 which is mono-substituted at the 2-position with a desired halo (e.g., chloro) substituent, although in the discussion which follows it is to be understood that an optically enriched isomer (such as 26) can be employed if a corresponding optically enriched dihalo substituted product is desired. Acid 24 can be reacted with thionyl chloride to make the corresponding 9-acid chloride followed by the addition of a lower alcohol (such as methanol or ethanol) to afford a lower 9-alkyl ester. The 2-halo ester can then be nitrated at the 7-position by reaction with a suitable nitrating agent such as a combination of trifluoroacetic anhydride and ammonium nitrate under an inert gas (e.g., nitrogen) atmosphere. This reaction will generally produce a mixture of 2-halo-6-nitro and 2-halo-7-nitro positional isomers which can be separated by conventional separation techniques such as recrystallization or flash chromatography over silica gel. The 2-halo-7-nitro isomer can be reduced to the corresponding 7-amino-2-halo compound by a suitable reducing agent such as stannous chloride, and the 7-amino-2-halide thus obtained can be converted to the corresponding 2,7-dihalo alkyl ester by reaction with a diazotizing agent such as tert-butyl nitrite followed by treatment with a cupric halide such as cupric chloride or cupric bromide. The ester can then be cleaved with a suitable base (such as an alkali metal hydroxide) to afford the corresponding 2,7-halo substituted acid.

It is further noted that if an oxygenated substituted methanoanthracene (for example a 2-chloro-7-methoxy derivative) is desired, it can be prepared starting with a 7-amino-2-halo derivative as described above. The amine is treated with a diazotizing agent such as tert-butyl nitrite followed by treatment with the salt of a suitable acid such as trifluoroacetic acid (the salt for example being formed with potassium carbonate in trifluoroacetic acid). The resulting trifluoroacetate can be hydrolyzed by conventional means and (1-6C)alkyl groups attached to the oxygen by treatment with base in the presence of a corresponding (1-6C)alkyl halide (such as methyl iodide).

As indicated by the R,S notation in Scheme I, acid 24 is racemic. Resolution of racemic acid 24 can be accomplished by fractional crystallization of diastereomeric salts, formed by addition of a chiral amine such as (+)-pseudoephedrine, from a suitable solvent such as ethanol to yield optically enriched acid 26. Treatment of 26 with thionyl chloride yields a correspondingly optically enriched acid chloride. Optically enriched intermediates can be employed in chiral syntheses to make optically enriched compounds according to the invention.

An amine of formula II can be made, as illustrated in Scheme II, by treating a 9-acid of formula VI (G=hydroxyl) with thionyl chloride to convert it to the corresponding 9-acid chloride of formula VI (i.e., wherein G is a halo group such as chloro), followed by reacting the 9-acid chloride with 4-t-butoxycarbonylaminopiperidine, that is, 4-aminopiperidine in which the 4-amino group has been protected with a 4-t-butoxycarbonyl moiety, to afford protected aminopiperidine 40. Alternatively, protected aminopiperidine 40 can also be made by reacting an acid of formula VI directly with 4-t-butoxycarbonyl-aminopiperidine in the presence of activators such as DMAP and WSCDI. The reaction can be conducted in a suitable solvent such as pyridine. Protected aminopiperidine 40 can then be reacted with trifluoroacetic acid to deprotect the piperidine 4-amino group and the remaining amide carbonyl reduced borane-dimethylsulfide complex to afford the corresponding amine of formula II.

An alternative method for making an aminopiperidine of formula II is illustrated in Scheme III. An acid of formula VI can first be reacted with 4-t-butoxycarbonylaminopiperidine, followed by treatment with a suitable reduced agent such as sodium cyanoborohydride in the presence of a drying agent, such as a 3–4 A molecular sieve, to afford protected aminopoperidine 50. The protective group can then be suitably cleaved with trifluoroacetic acid in a solvent such as methylene chloride.

A compound of formula III can be made by reacting a corresponding aminopiperidine of formula II with bromoacetyl bromide in the presence of a base such as a trialkylamine, for example triethylamine or ethyldiisopropylamine in methylene chloride at −20° to 25° C.

An isocyanate of formula IV can be made by phosgenating a corresponding amine of formula II with triphosgene in refluxing methylene chloride.

An imidazole of formula V can be made by reacting a corresponding aminopiperidine of formula II with carbonyl diimidazole in THF at a temperature of 0° to 25° C.

An amino piperidine of formula VIII can be made by treating a corresponding benzylpiperidine of formula XI with 1-chloroethylformate. The reaction can be conducted in a solvent such as 1,2-dichloroethane and at a temperature of from 25° C. to reflux.

A compound of formula IX can be obtained by reacting a corresponding compound of formula VI (G=halo such as chloro) with 4-hydroxypiperidine to afford the corresponding 9-ylcarbonylpiperidin-4-ol compound. The carbonyl group can then be suitably reduced to methylene using a reducing agent such as lithium aluminum hydride, followed by oxidation of the piperidine-4-ol moiety to afford the corresponding piperidin-4-one.

A benzylpiperidine of formula XI can be made by treating 4-amino-1-benzylpiperidine with a corresponding compound of R'Cl or R'Br.

It is noted that many of the starting materials for synthetic methods as described above are commercially available and/or widely reported in the scientific literature.

Examples of suitable pharmaceutically acceptable salts are organic acid addition salts formed with acids which form a physiologically acceptable anion, for example, tosylate, methanesulfonate, acetate, oxalate, tartrate, citrate, succinate, benzoate, ascorbate, α-ketoglutarate, and α-glycerophosphate. Suitable inorganic slats may also be formed such as sulfate, nitrate, and hydrochloride. Pharmaceutically acceptable salts may be obtained using standard procedures well known in the art, for example by reacting a compound of formula I with a suitable acid affording a physiologically acceptable anion.

When used to treat psychoses, a compound of formula I is generally administered as an appropriate pharmaceutical composition which comprises a compound of formula I as defined hereinbefore together with a pharmaceutically acceptable diluent or carrier, the composition being adapted for the particular route of administration chosen. Such compositions are provided as a further feature of the invention. They may be obtained employing conventional procedures and excipients and binders and may be in a variety of dosage forms. For example, they may be in the form of tablets, capsules, solutions or suspensions for oral administration; in the form of suppositories for rectal administration; in the form of sterile solutions or suspensions for administration by intravenous, intravesicular, subcutaneous or intramuscular injection or infusion; or in the form of a patch for transdermal administration. Oral administration is preferred.

The dose of compound of formula I which is administered will necessarily be varied according to principles well known in the art taking account of the route of administration, the severity of the psychotic condition, and the size and age of the patient. In general, a compound of formula I will be administered to a warm blooded animal (such as man) so that an effective dose is received, generally a daily dose in the range of about 0.01 to about 40 mg/kg body weight. For example, if the compound is administered intramuscularly it is administered in the range of about 0.01 to about 10 mg/kg body weight. If it is administered orally, it is administered in the range of about 0.1 to about 40 mg/kg body weight.

It will be apparent to those skilled in the art that a compound of formula I can be co-administered with other therapeutic or prophylactic agents and/or medicaments that are not medically incompatible therewith. Compounds within the scope of the invention do not show any indication to overt toxicity in laboratory test animals at several multiples of the minimum effective dose.

The compounds of Formula I are antagonists of dopamine D-2 receptors, and as such are predicted to be useful as antipsychotic drugs. D-2 antagonism can be shown by standard tests such as antagonism of [$^3$H]-spiperone binding (Test A), and /or antagonism of apomorphine-induced climbing and apomorphine-induced disruption of swimming (Test B).

Test A

The receptor binding assay used to measure affinities of various compounds for the dopamine (DA) D-2 receptor subtype was that described by Saller and Salama in J Pharmacol Exp Ther 236, page 714, 1986.

Specifically, rat striatal membranes were used. Tissue membranes were prepared and washed once in 50 volumes of the appropriate Tris HCl buffer. For the D-2 receptor binding assay, striatal membranes were suspended to a final concentration of 8 mg/ml in 50 mM Tris HCl with 40 nM ketanserin, pH 7.7. Nonspecific binding to D-2 receptors was measured in the presence of 1.0 µM (+)-butaclamol. $IC_{50}$s (drug concentration which produced a 50% displacement) for the displacement of 0.5 nM [$^3$H] spiperone were determined using at least five concentrations of each drug in triplicate. One-half milliliter of membrane suspension was incubated with the compound of interest or vehicle or nonspecific drug, ligand and appropriate Tris HCl buffer. The final reaction volume totaled 1 ml of each tube and was incubated at 37° C. for 15 min to facilitate binding and ensure equilibrium had been met. A Brandel filtering system equipped with GF/B filters was used to separate bound from free drug. The amount of drug bound to the membranes was assessed using liquid scintillation counting techniques. $IC_{50}$ values were obtained from a least squares regression of a logit-log transformation of the data. Typical values obtained in this test for $IC_{50}$ were 9 nM (nanomolar) for the compound of Example 1 and 146 nM for the compound of Example 24.

Test B

Female Swiss-Webster mice weighing approximately 20 g were deprived of food for approximately 24 h and then dosed orally with various doses of either the vehicle or test agent over a range of doses (N=20 mice per treatment group). Thirty minutes later they were dosed with apomorphine HCl at 1.25 mg/kg, sc, and placed into climbing cages. The climbing cages were 9 cm wide, 15 cm deep and 30 cm high. One wall had 27 horizontal rungs spaced 1 cm apart. Thirteen minutes after apomorphine each mouse was observed continuously for 1 min and the highest and lowest rung reached by its front paws was recorded. The mean of these two scores was used as the score for that mouse. (The highest and lowest scores were 27 and 0, respectively.) Immediately after the 1-min climbing observation period each mouse was placed into a circular swimming tank for 2 min and the number of swims was counted. The height of the tank was 15 cm and the diameter was 28 cm. A circular obstacle measuring 10.5 cm in diameter and having a height of 17 cm was placed into the center of the tank, creating a circular swimming channel 8.75 cm wide. The water level was 5.5 cm and the water was kept at room temperature. Marks were placed on the floor and side of the tank 180 degrees apart. A "swim" was scored each time a mouse swam from one mark to the other. The mice were observed through overhead mirrors and the number of 180 degree swims was recorded for each mouse. Activity in this test was indicated by a decrease in the climbing score accompanied by an increase in the swimming score at a given dose of the test compound. Typical values of minimum effective doses in this test were 2.5 mg/kg for the compound of Example 1 and 40 mg/kg for the compound of Example 24.

In general, compounds were considered active if they provided an $IC_{50}$ value of 500 nM or less in Test A, and/or were active following an oral dose of 40 mg/kg or less in Test B.

The invention will now be illustrated by the following non-limiting examples in which, unless stated otherwise:

(i) temperatures are given in degrees Celsius (C.); operations were carried out at room or ambient temperature, that is, at a temperature in the range of 18°–25° C.

(ii) evaporation of solvent was carried out using a rotary evaporator under reduced pressure (600–4000 pascals; 4.5–30 mmHg) with a bath temperature of up to 60° C.;

(iii) flash chromatography was carried out on Merck Kieselgel (Art 9385) or Baker Flash silica gel; thin layer chromatography (TLC) was carried out on Analtech 0.25 mm silica gel GHLF plates (Art 21521), obtainable from Analtech, Newark, Del., USA;

(iv) high pressure liquid chromatography (HPLC) for analysis of enantiomeric purity determinations of chiral compounds was carried out on either a 25 cm×4.6 mm Chiralcel™ OD or a 15 cm×4.6 mm Ultron Ovomucoid column available from JT Baker, Inc.; HPLC analysis for most reactions and final products was carried out on either a 25 cm×4.6 mm Supelcosil™ LC-8-DB, a 25 cm×4.6 mm Supelcosil™ LC-18-DB column, available from Supelco, State College Pa., USA or a 25 cm×4.6 mm Zorbax™ RX column.

(v) in general, the course of reactions was followed by TLC and/or HPLC and reaction times are given for illustration only;

(vi) melting points are uncorrected and (dec) indicates decomposition; the melting points given are those obtained for the materials prepared as described; polymorphism may result in isolation of materials with different melting points in some preparations;

(vii) all final products were essentially pure by TLC and/or HPLC and had satisfactory nuclear magnetic resonance (NMR) spectra and microanlaytical data; (viii) yields are given for illustration only;

(ix) reduced pressures are given as absolute pressures in pascals (Pa); other pressures are given as gauge pressures in bars;

(x) chemical symbols have their usual meanings; the following abbreviations have also been used: v (volume), w (weight), mp (melting point), L (liters), mL (milliliters), g (grams), mmol (millimoles), mg (milligrams), min (minutes), h (hour);

(xi) solvent ratios are given in volumes: volume (v/v) terms; and (xii) "NMR" refers to proton NMR unless otherwise specified.

(xiii) specific optical rotations were measured at the sodium D line.

EXAMPLE 1

N-(1-[(9S,10S)-(+)-2-Chloro-9,10-dihydro-9,10-methanoanthracen-9-ylmethyl]-4-piperidyl)-2-ethoxyacetamide To a stirred solution of 4-amino-1-[(9S,10S)-2-chloro-9,10-dihydro-9,10-methanoanthracene-9-ylmethyl]piperidine (752 mg, 2.22 mmol), dimethylaminopyridine (542 mg, 4.44 mmol), 1-ethyl-3-(3-dimethylaminopropyl)carbodiimide hydrochloride (848 mg, 4.44 mmol), in methylene chloride (15 mL) was added ethoxyacetic acid (0.25 mL, 2.44 mmol). After stirring for 18 h, the mixture was treated with 1N sodium hydroxide (75 mL), and extracted with methylene chloride (3×75 mL). The combined extracts were washed with 1N sodium hydroxide (2×75 mL) and brine (50 mL), dried (sodium sulfate), filtered and concentrated to give a milky white syrup. Chromatography of this material over silica gel (eluant: ethyl acetate) provided the title compound as a colorless glass (807 mg, 86%), mp 68.0°–70.0° C.; MS(CI): 425 (M+H); 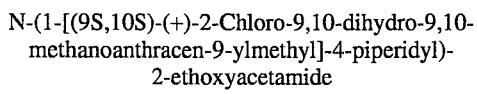 NMR (300 MHz,DMSO-$d_6$): 1.13(t, 3H, J=7.0 Hz), 1.49(m, 2H), 1.61(m, 2H), 2.26(m, 2H, J=11.9 Hz), 2.46(br s, 2H), 2.94(m, 2H), 3.33(m, part. submerged, 2H), 3.43(q, 2H, J=7.0 Hz), 3.62(m, 1H), 3.78(s, 2H), 4.33(s, 1H), 6.94(m, 3H), 7.23(br m, 4H), 7.48(d, 1H, J=8.3 Hz).

Analysis for $C_{25}H_{29}ClN_2O_2 \cdot 0.25\ H_2O$: Calculated: C, 69.92; H, 6.92; N, 6.52. Found: C, 70.16; H, 6.95; N, 6.39.

The starting 4-amino-1[(9S,10S)-2-chloro-9,10-dihydro-9,10-methanoanthracen-9-ylmethyl]piperidine was obtained as follows:

a. (9S, 10S)-2-Chloro-9,10-dihydro-9,10-methano-9-anthracenecarbonyl chloride

To a stirred suspension of (9S, 10S)-2-chloro-9,10-dihydro-9,10-methano-9-anthracenecarboxylic acid (1.0 g, 3.62 mmol), prepared as described in Example 109a, in toluene (10 mL) was added thionyl chloride (0.29 mL, 3.98 mmol). After refluxing for 1.5 h, the mixture was concentrated to give the title compound as a light yellow solid (1.05 g, quant.); MS(CI): 289 (M+H).

b. t-Butyl-N-(1-[(9S,10S)-2-chloro-9,10-dihydro-9,10-methanoanthracen-9-yl-carbonyl]-4-piperidyl)carbamate To a cold (ice bath) stirred solution of 4-t-butoxycarbonylaminopiperidine 0.80 g, 4.0 mmol) and pyridine (0.59 mL, 7.26 mmol) in methylene chloride (10 mL) was added the acid chloride produced in Example 1a (1.05 g, 3.63 mmol) in methylene chloride (15 mL). After stirring the resulting mixture for 1 h at 0° C., the cooling bath was removed and the reaction was allowed to warm to ambient temperature and stirred for an additional 18 h. The reaction mixture was then cooled to 0 C., treated with ice cooled 1N hydrochloric acid (15 mL), and extracted with methylene chloride (2×60 mL). The combined organic layers was washed with 1N hydrochloric acid (2×30 mL) and brine 30 mL), dried (sodium sulfate), filtered and concentrated to leave a colorless foam. This material was triturated with hot hexane:ether (3:1, 100 mL) to give the title compound as a colorless solid (1.24 g, 76%), mp 154.5°–5.5° C.; MS(CI): 453 (M+H); NMR (300 MHz,DMSO-$d_6$): 1.37(br s, 11H), 1.82(m, 2H), 2.72–2.99(br m, 4H), 3.29(m, 2H), 3.49–3.65(br m, 2H), 4.43(br s, 2H), 7.01(m, 4H), 7.35(m, 3H), 7.62(br s, 1H).

c. 4-Amino-1-[(9S,10S)-2-chloro-9,10-dihydro-9,10-methanoanthracen-9-yl-carbonyl] piperidine To a stirred solution of t-butyl-N-(1-[(9S,10S)-2-chloro-9,10-dihydro-9,10-methanoanthracen-9-ylmethyl]-4-piperidyl)carbamate produced in Example 1b (1.24 g, 2.74 mmol) in methylene chloride (15 mL) was added trifluoroacetic acid (2.11 mL, 27.37 mmol). After stirring the resulting mixture for 18 h, the reaction was concentrated to give a pale pink syrup. The syrup was dissolved in methylene chloride (100 mL), cooled to 0 C. (ice bath) and treated with 3N sodium hydroxide and extracted with methylene chloride (3×50 mL). The combined extracts was washed with 3N sodium hydroxide (2×75 mL) and brine (75 mL), dried (sodium sulfate), filtered, and concentrated to give the title compound as a white foamy glass (967 mg, 100%); mp 93°–5° C.; MS(CI); 353 (M+H); NMR (300 MHz,DMSO-$d_6$): 1.23(br m, 2H), 1.67–1.85(br m, 2H), 2.71–3.02(br m, 5H), 3.27–3.39(br m, part. submerged, 2H), 3.66(br s, 1H), 4.42(s, 1H), 4.47(s, 1H), 7.00(m, 3H), 7.30–7.66(br m, 4H).

d. 4-Amino-1-[(9S,10S)-2-chloro-9,10-dihydro-9,10-methanoanthracen-9-ylmethyl] piperidine To a stirred solution of the title compound produced in Example 1c (850 mg, 2.41 mmol), boron trifluoride etherate (0.45 mL, 3.62 mmol) in tetrahydrofuran (20 mL) was added borane-tetrahydrofuran (12.04 mL, 12.04 mmol). After refluxing for 18 h, the mixture was treated with methanolic hydrochloric acid (20 mL) and refluxed an additional 2 h. The mixture was treated with 1N sodium hydroxide until the pH was 12 and extracted with methylene chloride (3×75 mL). The combined extracts was washed with 10% sodium hydroxide (2×50 mL) and brine (50 mL), dried (sodium sulfate), filtered, and concentrated to give the title compound as a colorless syrup (752 mg, 92%); MS(CI): 339 (M+H); NMR (300 MHz,DMSO-$d_6$): 1.25(m, 2H), 1.82(m, 2H), 2.19(m, 2H), 2.49(m, part. submerged by DMSO, 3H), 2.91(m, 2H), 3.28(m, part. submerged by H2O, 2H), 4.32(s, 1H), 6.94(m, 3H), 7.18–7.27(br m, 4H).

e. Alternative procedure for 4-amino-1-[(9S,10S)-2-chloro-9,10-dihydro-9,10-methanoanthracen-9-ylmethyl]piperidine Using a procedure similar to that described in Example 1d except starting with a larger amount of 1c (7.94 g, 22.5 mmol). After refluxing for 18 h, the reaction was concentrated to give a yellow oil. This material was dissolved in cold (ice bath) ether (1200 mL) and treated with hydrogen chloride gas for 30 min. The resulting dihydrochloride was filtered and was dissolved in water (300 mL), treated with 1N sodium hydroxide (300 mL) and extracted with methylene chloride (2×500 mL). The combined extracts was washed with 1N sodium hydroxide (2×150 mL) and brine (150 mL), dried (sodium sulfate), filtered, and concentrated to give the title compound as a colorless oil (6.78 g, 89%).

EXAMPLE 2

N-(1-[(9S,10S)-(+)-2-Chloro-9,10-dihydro-9,10-methanoanthracen-9-ylmethyl]-4-piperidyl)-2-ethoxyacetamide oxalate To a solution of N-(1-[(9S,10S)-(+)-2-chloro-9,10-dihydro-9,10-methanoanthracen-9-ylmethyl]-piperidyl)-2-ethoxyacetamide (2.24 g, 5.27 mmol) in ether (50 mL) was added a solution of oxalic acid (0.47 g, 5.27 mmol) in ether (5 mL). The resulting solid was filtered and dried (0.05 mm/80 C.) to give the title compound as a white solid (2.26 g, 83%), mp 193.0°–3.5° C.; MS(CI): 425 (M+H); NMR (300 MHS,DMSO-$d_6$): 1.14(t, 3H, J=7.0 Hz), 1.67–1.79(br m, 4H), 2.58(s, 2H), 2.79(m, 2H), 3.25(m, 2H), 3.47(q, 2H, J=7.0 Hz), 3.70–3.88(br m, 3H), 4.41(s, 1H), 6.98(m, 3H), 7.30(m, 4H), 7.68(m, 1H).

Analysis for $C_{25}H_{29}ClN_2O_2.C_2H_2O_4.0.75\ H_2O$: Calculated: C, 61.36; H, 6.20; N, 5.30. Found: C, 61.34; H, 5.95; N, 5.17.

EXAMPLE 3

N-(1-[(9R,10R)-(–)-2-Chloro-9,10-dihydro-9,10-methanoanthracen-9-ylmethyl]-4-piperidyl)-2-ethoxyacetamide Using a procedure similar to that described in Example 1 except starting with 4-amino-1-[(9R,10R)-2-chloro-9,10-dihydro-9,10-methanoanthracen-9-ylmethyl]piperidine, the title compound was obtained as a white solid (59%), mp 93.0°–5.0° C.; MS(CI): 425 (M+H); $[\alpha]^{23}_D$=40° (c=0.01, CHCl$_3$); NMR (300 MHz,DMSO-$d_6$): 1.13(t, 3H, J=7.0 Hz), 1.49(m, 2H), 1.61(m, 2H), 2.26(br m, 2H), 2.46(br s, 2H), 2.94(m, 2H), 3.33(m, submerged, 2H), 3.43(q, 2H, J=7.0 Hz), 3.62(m, 1H), 3.78(s, 2H), 4.33(s, 1H), 6.94(m, 3H), 7.23(br m, 4H), 7.48(d, 1H, J=8.3 Hz).

Analysis for $C_{25}H_{29}ClN_2O_2.0.25\ H_2O$: Calculated: C, 69.92; H, 6.92; N, 6.52. Found: C, 70.04; H, 7.00; N, 6.46.

The starting 4-amino-1-[(9R,10R)-2-chloro-9,10-dihydro-9,10-methanoanthracen-9-ylmethyl]piperidine was prepared using a procedure similar to that described in Example 1a–1 d except starting with (9R,10R)-2-chloro-9,10-dihydro-9,10-methano-9-anthracenecarboxylic acid produce in Example 109b.

EXAMPLE 4

N-(1-[(9R,10R)-(–)-2-Chloro-9,10-dihydro-9,10-methanoanthracen-9-yl-methyl]-4-piperidyl)-2-ethoxyacetamide oxalate Using a procedure similar to that described in Example 2 except starting with N-(1-[(9R,10R)-(–)-2-chloro-9,10-dihydro-9,10-methanoanthracen-9-ylmethyl]-4-piperidyl)-2-ethoxyacetamide, the title compound was obtained as a white solid (97%), mp 194.0°–6.0° C.; MS(CI): 425 (M+H); NMR (300 MHz,DMSO-$d_6$): 1.14(t, 3H, J=6.5 Hz), 1.62–1.80(br m, 4H), 2.57(br s, 2H), 2.76(m, 2H), 3.19(m, 2H), 3.47(q, 2H, J=6.7 Hz), 3.70–3.80(br m, 5H), 4.40(s, 1H), 6.97(m, 3H), 7.30(m, 4H), 7.66(m, 1H).

Analysis for $C_{25}H_{29}ClN_2O_2.C_2H_2O_4.0.25\ H_2O$: Calculated: C, 62.42; H, 6.11; N, 5.39. Found: C, 62.20; H, 6.15; N, 5.31.

EXAMPLE 5

N-(1-[(9R,10R)-(–)-2-Chloro-9,10-dihydro-9,10-methanoanthracen-9-ylmethyl]-4-piperidyl)-2-ethoxyacetamide hydrochloride To a cold (ice bath) stirred solution of Example 3 (145 mg, 0.34 mmol) in ether (5 mL) was added ethereal hydrochloride (2 mL). After stirring at 0° C. for 0.5 h, the resulting suspension was filtered to give the title compound as a white solid (135 mg, 86%), mp 221.0°–3.0° C.; MS(CI): 425 (M+H); NMR (300 MHz, DMSO-$d_6$): 1.14(t, 3H, J=6.3 Hz), 1.19(m, 4H), 2.50(s, submerged by DMSO, 2H), 2.75(m, 2H), 3.40–3.55(br m, 4H), 3.83(s, 2H), 3.91(br s, 1H), 4.20–4.40(br m, 2H), 4.48(s, 1H), 7.01(m, 3H), 7.33(m, 4H), 7.93(d, 1H, J=8.0 Hz), 10.08(br, s, 1H).

Analysis for $C_{25}H_{29}ClN_2O_2.HCl.H_2O$: Calculated: C, 62.63; H, 6.73; N, 5.84. Found: C, 62.54; H, 6.52; N, 5.75.

EXAMPLE 6

N-(1-[2-Chloro-9,10-dihydro-9,10-methanoanthracen-9-ylmethyl]-4-piperidyl)-2-ethoxyacetamide Using a procedure similar to that described in Example 1 except starting with 4-amino-1-[2-chloro-9,10-dihydro-9,10-methanoanthracen-9-ylmethyl]piperidine and 2-ethoxyacetic acid, the title compound was obtained as a white glassy solid (68%), mp 112.5°–4.0° C.; MS(CI): 425 (M+H); NMR (300 MHz,DMSO-$d_6$): 1.12(t, 3H, J=7 Hz), 1.49(br m, 2H), 1.61(br m, 2H), 2.26(m, 2H)), 2.45(br m, 2H), 2.93(br m, 2H), 3.45(q, 2H, J=7 Hz), 3.62(br s, 1H), 3.78(s, 2H), 4.34(s, 1H), 6.94(m, 3H), 7.23(m, 4H), 7.48(d, 1H, J=8 Hz).

Analysis for $C_{25}H_{29}ClN_2O_2$: Calculated: C, 70.66; H, 6.88; N, 6.59. Found: C, 70.59; H, 6.85; N, 6.48.

The starting racemic amine was obtained as follows:

EXAMPLE 7 a) t-Butyl N-(1-[2-chloro-9,10-dihydro-9,10-methanoanthracen-9-ylmethyl]-4-piperidyl)carbamate To a stirred suspension of 2-chloro-9-formyl-9,10-dihydro-9,10-methanoanthracene (3.64 g, 14.25 mmol, described in Example 107i), 4-t-butoxycarbonylaminopiperidine (3.57 g, 17.81 mmol), and activated 3A sieves (powderized, 3.64 g) in methanol (50 mL, sieve dried) was added methanolic hydrochloric acid (ca. 3.5 mL) until the pH was 7.50. After 2 h, the mixture was treated with sodium cyanoborohydride (895 mg, 14.25 mmol) in four portions over a 4 h period. After stirring the resulting mixture an additional 72 h, ethyl acetate (100 mL) and 3N sodium hydroxide (100 mL) and filtered through celite. The filtrate was treated with 3N sodium hydroxide (250 mL) and extracted with ethyl acetate (2×300 mL). The combined extracts was dried (sodium sulfate), filtered and concentrated to give a tan foam. Chromatography of this material over silica gel (eluting in sequence with 1) 90:10 acetone:hexane (6 L) and 2) 85:15 acetone:hexane (1L)) to give the title compound as a white foam (3.24 g, 52%), mp 76.5°–80.0° C.; MS(CI): 439 (M+H); NMR (300 MHz, DMSO-$d_6$): 1.37(m, 11H), 1.64(m, 2H), 2.21(m, 2H), 2.46(s, 2H), 2.92(m, 2H), 3.17–3.42(br m, part. submerged by H2O, 3H), 4.33(s, 1H), 6.72(m, 1H), 6.95(m, 3H), 7.19(m, 2H), 7.26(m, 2H).

Analysis for $C_{26}H_{31}ClN_2O_2$: Calculated: C, 71.14; H, 7.12; N, 6.38. Found: C, 71.50; H, 7.21; N, 5.67.

b) 4-Amino-1-[2-chloro-9,10-dihydro-9,10-methanoanthracen-9-ylmethyl]piperidine

Using a procedure similar to that described in Example 1c except starting with racemic t-butyl N-(1-[2-chloro-9,10-dihydro-9,10-methanoanthracen-9-ylmethyl]-4-piperidyl)carbamate, the title compound was obtained as a white foam (96%); MS(CI): 339 (M+H); NMR (300 MHz,DMSO-$d_6$): 1.15–1.34(m, 2H), 1.59–1.73(m, 2H), 2.10–2.27(m, 2H), 2.39–2.65(m, 3H), 2.82–2.98(m, 2H), 3.03(br s, 2H), 3.28(d, 1H, J=13.9 Hz), 3.35(d, 1H, J=13.9 Hz), 4.33(s, 1H), 6.87–7.00(m, 3H), 7.12–7.31(m, 4H).

EXAMPLE 8

N-(1-[9,10-Dihydro-9,10-methanoanthracen-9-ylmethyl]-4-piperidyl)-2-ethoxyacetamide Using a procedure similar to that described in Example 1 except starting with 4-amino-1-[9,10-dihydro-9,10-methanoanthracen-9-ylmethyl]piperidine and 2-ethoxyacetic acid, the title compound was obtained as a white solid (76%), mp 158.0°–9.0° C.; MS(CI): 391 (M+H); NMR (300 MHz, DMSO-$d_6$): 1.12(t, 3H, J=7.0 Hz), 1.41–1.69(m, 4H), 2.27(m, 2H), 2.45(s, 2H), 2.95(m, 2H), 2.95(m, 2H), 3.45(q, 2H, J=7.0 Hz), 3.63(m, 1H), 3.78(s, 2H), 4.31(s, 1H), 6.92(m, 4H), 7.17–7.23(m, 4H), 7.47(d, 2H, J=8.0 Hz).

Analysis for $C_{25}H_{30}N_2O_2 \cdot 0.5\ H_2O$: Calculated: C, 75.15; H, 7.82; N, 7.01. Found: C, 75.31; H, 7.58; N, 6.98.

The starting racemic amine was obtained as follows:
a. t-Butyl N-(1-[9,10-dihydro-9,10-methanoanthracen-9-ylmethyl]-4-piperidyl)carbamate To a stirred solution of 4-t-butoxycarbonylaminopiperidine (1.10 g, 5.5 mmol) and powderized 3A sieve (1.14 g, dried under vacuum at 125 C. at 0.05 mm for 18 h) in methanol (9.1 mL, 3A sieve dried) was added 9-formyl-9,10-dihydro-9,10-methanoanthracene (1.10 g, 5.0 mmol, described in M. Sunagawa, et al; Chem. Pharm. Bull. Vol. 27 (1979) pp 1806–1812; U.S. Pat. No. 4,224,344 Sunagawa et al, Sumitomo, Ltd.; Sep. 23, 1980; U.S. Pat. No. 4,358,620 Sunagawa et al, Sumitomo, Ltd.; Nov. 9, 1982). After stirring for 24 h, 95% sodium cyanoborohydride (232 mg, 3.5 mmol) was added in two portions over 30 min. After stirring for 2 h, the solution was concentrated to ca. 3 mL and methylene chloride (30 mL) and sodium hydroxide (10 mL) were added. The solution was stirred for 30 min and filtered through diatomaceous earth with methylene chloride wash. The organic layer was washed with 1N sodium hydroxide, dried (sodium sulfate), filtered and concentrated to give an oil. This material was crystallized from hot methanol to give the title compound. The filtrate was concentrated and chromatographed over silica gel (eluting in sequence with: 1) methylene chloride; 2) 5:95 ethyl acetate:methylene chloride and 3) 10:90 ethyl acetate:methylene chloride) to give more of the product. This was combined with the product from above to give the title compound as a white solid (905 mg, 45%), mp 155.0°–160.5° C.; MS(CI): 405 (M+H); NMR (300 MHz, DMSO-$d_6$): 1.34(m, 11H), 1.63(m, 2H), 2.20(m, 2H), 2.43(s, 2H), 2.93(m, 2H), 3.15–3.34(m, 3H), 4.30(s, 1H), 6.72(d, 1H, J=8.0 Hz), 6.91(m, 4H), 7.15–7.27(m, 4H).

Analysis for CHNO: $C_{26}H_{32}N_2O_2$: Calculated: C, 77.19; H, 7.97; N, 6.92. Found: C, 77.17; H, 8.09; N, 6.82.

b. 4-Amino-1-[9,10-dihydro-9,10-methanoanthracen-9-ylmethyl]piperidine

Using a procedure similar to that described in Example 1c except starting with t-butyl N-(1-[9,10-dihydro-9,10-methanoanthracen-9-ylmethyl]-4-piperidyl)carbamate, the title compound was obtained as a white solid (quant), mp 116.0°–9.0° C.; MS(CI): 305 (M+H); NMR (300 MHz, DMSO-$d_6$): 1.13–1.28(m, 2H), 1.57–1.70(m, 2H), 2.13–2.25(m, 2H), 2.44(s, 2H), 2.46–2.60(m, part. submerged by DMSO, 1H), 2.85–2.96(m, 2H), 3.32(s, submerged by H2O, 2H), 4.30(s, 1H), 6.83–6.97(m, 4H), 7.17(m, 2H), 7.26(m, 2H).

EXAMPLE 9

(2S)-N-(1-[2-Chloro-9,10-dihydro-9,10-methanoanthracen-9-ylmethyl]-4-piperidyl)-2-methoxypropionamide oxalate Using a procedure similar to that described in Example 6 except starting with (2S)-2-methoxypropionic acid[3], the title compound was obtained as a white solid (63%), mp 189.0°–91.0° C.; MS(CI): 425 (M+H); NMR (300 MHz, DMSO-$d_6$): 1.19(d, 3H, 6.6 Hz), 1.55–1.85(br m, 4H), 2.57(s, 2H), 2.57(m, 2H), 3.22(br s, 5H), 3.60–3.85(br m, part. submerged, 4H), 4.41(s, 1H), 6.99(m, 3H), 7.30(m, 4H), 7.80(br s, 1H).

[3]Obtained using a similar procedure as described in T. Purdie and J. C. Irvine, *J.C.S.*, 1899, 75, 483.

Analysis for $C_{25}H_{29}ClN_2O_2 \cdot C_2H_2O_4 \cdot 0.25\ H_2O$: Calculated: C, 62.42; H, 6.11; N, 5.39. Found: C, 62.59; H, 6.02; N, 5.28.

EXAMPLE 10

(2R)-N-(1-[2-Chloro-9,10-dihydro-9,10-methanoanthracen-9-ylmethyl]-4-piperidyl)-2-methoxypropionamide oxalate Using a procedure similar to that described in Example 6 except starting with (2R)-2-methoxypropionic acid[1], the title compound was obtained as a white solid (63%), mp 190.0°–2.0° C.; MS(CI): 425 (M+H); NMR (300 MHz, DMSO-$d_6$): 1.19(d, 3H, H=6.5 Hz), 1.55–1.85(br m, 4H), 2.57(s, 2H), 3.22(br s, 5H), 3.60–3.85(br m, part. submerged, 4H), 4.41(s, 1H), 6.99(m, 3H), 7.30(m, 4H), 7.80(br s, 1H).

[1](2R)-2-Methoxypropionic acid, $[\alpha]_D^{26.5}=+65.0$ (c=0.01, $CHCl_3$, lit $[\alpha]_D^{22}=+72$, pure liquid) was prepared by the procedure of T. Purdie and J. C. Irvine, *J.C.S.*, 1899, 75, 483, except stirring from (2R)-(+)-methyl 2-methoxypropionate.

Analysis for $C_{25}H_{29}ClN_2O_2 \cdot C_2H_2O_4 \cdot 0.25\ H_2O$: Calculated: C, 62.42; H, 6.11; N, 5.39. Found: C, 62.59; H, 6.02; N, 5.28.

(2R)-methyl 2-methoxypropionate.

To a 20° C. solution of (2R)-(+)-methyl 2-hydroxypropionate (9.17 mL, 96 mmol) and methyl iodide (18 mL, 288 mmol) was added silver tetrafluoroborate (28.03 g, 144 mmol) in four portions. After the addition of each portion of silver fluoroborate, the exothermic reaction was allowed to cool to 20° C. before more silver fluoroborate was added. The mixture was stirred for 2 h and water (50 mL) followed by ether (100 mL) were added. The resulting mixture was filtered through diatomaceous earth with ether (150 mL) wash. The filtrate was carefully concentrated on a rotary evaporator and vacuum pumped for a short period in order to minimize the lost of the volatile product. This was converted to (2R)-2-methoxypropionic acid without further purification.

EXAMPLE 11

(2R)-N-(1-[(9S,10S)-2-Chloro-9,10-dihydro-9,10-methanoanthracen-9-ylmethyl]-4-piperidyl)-2-methoxypropionamide oxalate Using a procedure similar to that described in Example 1 and Example 2 (oxalate salt formation) except starting with 4-amino-1-[(9S,10S)-2-chloro-9,10-dihydro-9,10-methanoanthracen-9-ylmethyl]piperidine and (2R)-2-methoxypropionic acid, the title compound was obtained as a white solid (coupling: 65%, salt formation: 84%), mp 206.0°–207.5 (dec) °C.; MS(CI): 425 (M+H); NMR (300 MHz,DMSO-$d_6$): 1.19(d, 3H, J=6.7 Hz), 1.58–1.82(br m, 4H), 2.58(s, 2H), 2.76(m, 2H), 3.22(m, part. submerged by $H_2O$, 5H), 3.65(q, 1H, J=6.5 Hz), 3.74(m, 3H), 4.40(s, 1H), 6.98(m, 3H), 7.30(m, 4H), 7.80(m, 1H).

Analysis for $C_{25}H_{29}ClN_2O_2 \cdot C_2H_2O_4 \cdot 0.25\ H_2O$: Calculated: C, 62.42; H, 6.11; N, 5.39. Found: C, 62.56; H, 6.06; N, 5.37.

EXAMPLE 12

N-(1-[2-Chloro-9,10-dihydro-9,10-methanoanthracen-9-ylmethyl]-4piperidyl)-2-methoxy-2-cyclopentylacetamide oxalate Using a procedure similar to that described in Example 6 and Example 2 (oxalate salt formation) except starting with 2-methoxy-2-cyclopentylacetic acid, the title compound was obtained as a white solid (53%), mp 130.0°–5.0° C.; MS(CI): 479 (M+H); NMR (300 MHz,DMSO-$d_6$): 1.33–1.76(br m, 12 H), 2.07(m, 1H), 2.59(m, 4H), 2.79(m, 2H), 3.21(s, 3H), 3.32(d, 1H, J=7.2 Hz), 3.78(m, 3H), 4.69(s, 1H), 6.98(m, 3H), 7.30(m, 4H), 7.85(m, 1H).

Analysis for $C_{29}H_{35}ClN_2O_2 \cdot C_2H_2O_4 \cdot H_2O$: Calculated: C, 63.42; H, 6.69; N, 4.77. Found: C, 63.44; H, 6.22; N, 4.67.

EXAMPLE 33

N-[1-(2-Chloro-9,10-dihydro-9,10-methanoanthracen-9-ylmethyl)-4-piperidyl]-2-(2,3,4,5-tetrahydrofuran)amide Using a procedure similar to that described in Example 6 except starting with 2-tetrahydrofuroic acid, the title compound was obtained as a white glassy solid (70%), mp 78.0°–82.0° C.; MS(CI): 437 (M+H); NMR (300 MHz, DMSO-$d_6$): 1.49–1.59(br m, 4H), 1.78(br m, 2H), 2.07(br m, 2H), 2.25(br q, 2H, J=11.2 Hz), 2.50(br s, 2H), 2.93(br m, 2H), 3.29(d, submerged by H2O, 1H), 3.38(d, 1H, J=14 Hz), 3.58(br m, 1H), 3.73(q, 1H, J=6.8 Hz), 3.85(q, 1H, J=7.0 Hz), 4.14(m, 1H), 6.94(m, 3H), 7.20(m, 2H), 7.27(d, 2H, J=7.7 Hz), 7.49(d, 1H, J=8.1 Hz).

Analysis for $C_{26}H_{29}ClN_2O_2 \cdot 0.25\ H_2O$: Calculated: C, 70.74; H, 6.73; N, 6.35. Found: C, 70.93; H, 6.63; N, 6.35.

EXAMPLE 14

N-[1-(2-Chloro-9,10-dihydro-9,10-methanoanthracen-9-ylmethyl)-4-piperidyl]-2-(dimethylamino)acetamide Using a procedure similar to that described in Example 6 except starting with 2-(dimethylamino)acetic acid, the title compound was obtained as a white glassy solid (43%), mp 66.0°–70.0° C.; MS(CI): 424 (M+H); NMR (300 MHz, DMSO-$d_6$): 1.44(m, 2H), 1.63(m, 2H), 2.18(s, 6H), 2.28(m, 2H), 2.50(s, 2H), 2.82(s, 2H), 2.91(m, 2H), 3.30(d, submerged by $H_2O$, 1H), 3.38(d, 1H, J=14 Hz), 3.58(m, 1h), 4.33(s, 1H), 6.93(m, 3H), 7.20(d, 2H, J=9.0 Hz), 7.27(d, 2H, J=7.8 Hz), 7.52(d, 1H, J=8.0 Hz).

Analysis for $C_{25}H_{30}ClN_3O$: Calculated: C, 70.08; H, 7.17; N, 9.81. Found: C, 69.93; H, 7.09; N, 9.84.

EXAMPLE 15

N-[1-(2-Chloro-9,10-dihydro-9,10-methanoanthracen-9-ylmethyl)-4-piperidyl]-2-(acetylamino)acetamide Using a procedure similar to that described in Example 6 except starting with N-acetylglycine, the title compound was obtained as a white solid (63%), mp 128.0°–30.0° C.; MS(CI): 438 (M+H); NMR (300 MHz,DMSO-$d_6$): 1.40(m, 2H), 1.63(m, 2H), 1.83(s, 3H), 2.28(m, 2H), J=11.6 Hz), 2.46(br s, 2H), 2.94(m, 2H), 3.29(d, 1H, J=13.7 Hz), 3.35(d, 1H, submerged by $H_2O$), 3.55(br s, 1H), 3.61(d, 2H, =5.8 hz), 4.33(s, 1H), 6.94(m, 3H), 7.23(m, 4H), 7.71(d, 1H, J=7.8 Hz), 8.02(m, 1H).

Analysis for $C_{25}H_{28}ClN_3O_2$: Calculated: C, 68.58; H, 6.44; N, 9.60. Found: C, 68.35; H, 6.52; N, 9.36.

EXAMPLE 16

N-(1-[(9S,10S)-2-Chloro-9,10-dihydro-9,10-methanoanthracen-9-ylmethyl]-4-piperidyl)-2,2-dimethoxyacetamide Using a procedure similar to that described in Example 1 except starting with 2,2-dimethoxyacetic acid[1], the title compound was obtained as a white solid (coupling: 64%; salt formation: 80%), mp 187.5°–9.0° C.; MS(CI): 441 (M+H); NMR (300 MHz, DMSO-$d_6$): 1.54–1.86(br m, 4H), 2.57(br s, 2H), 2.75(m, 2H), 3.14–3.36(br m, part. submerged by $H_2O$, 8H), 3.75(m, 3H), 4.40(s, 1H), 4.61(s, 1H), 6.98(m, 3H), 7.30(m, 4H), 7.92(m, 1H).

[1]Obtained using a similar procedure as described in H. Scheibler and H.-J. Schmidt, *Berichte*, 1936, 69, 12, except starting from methyl dimethoxyacetate.

Analysis for $C_{25}H_{29}ClN_2O_3 \cdot C_2H_2O_4 \cdot 0.25\ H_2O$: Calculated: C, 60.56; H, 5.93; N, 5.23. Found: C, 60.53; H, 5.93; N, 5.07.

EXAMPLE 17

N-(1-[2-Chloro-9,10-dihydro-9,10-methanoanthracen-9-ylmethyl]-4-piperidyl)-2,2-dimethoxyacetamide Using a procedure similar to that described in Example 6 except starting with 2,2-dimethoxyacetic acid[1], the title compound was obtained as a light tan solid (50%), mp 164.0°–5.0° C.; MS(CI): 441 (M+H); NMR (300 MHz, DMSO-$d_6$): 1.49–1.62(br m, 4H), 2.23(m, 2H), 2.95(m, 2H), 3.25(s, 6H), 3.33(d, submerged by $H_2O$, 1H), 3.38(d, 1H, J=14.1 Hz), 3.57(br s, 1H), 4.33(s, 1H), 4.58(s, 1H), 6.94(m, 3H), 7.22(m, 4H), 7.73(d, 1H, J=8.2 Hz).

[1]Obtained using a similar procedure as described in H. Scheibler and H.-J. Schmidt, *Berichte*, 1936, 69, 12, except starting from methyl dimethoxyacetate.

Analysis for $C_{25}H_{29}ClN_2O_3 \cdot 0.25\ H_2O$: Calculated: C, 67.41; H, 6.67; N, 6.29. Found: C, 67.34; H, 6.59; N, 6.01.

EXAMPLE 18

N-(1-[(9S,10S)-2-Chloro-9,10-dihydro-9,10-methanoanthracen-9-ylmethyl]-4-piperidyl)-2,2-diethoxyacetamide oxalate Using a procedure similar to that described in Example 1 except starting with 2,2-diethoxyacetic acid[2], and followed by oxalate salt formation as described in Example 2, the title compound was obtained as a white solid (60%), mp 141.0°–3.0° C.; MS(CI): 469 (M+H); NMR (300 MHz, DMSO-$d_6$): 1.14(t, 6H, J=7.0 Hz), 1.73(m, 4H), 2.57(br s, 2H), 2.69–2.76(br m, 2H), 3.18(m, 2H), 3.46–3.62(br m, 6H), 3.75(br s, 1H), 4.40(s, 1H), 4.69(s, 1H), 6.99(m, 3H), 7.29(m, 4H), 7.81(m, 1H).

[2]2,2-Diethoxyacetic acid was obtained using a similar procedure as described in H. Scheibler and H.-J. Schmidt, *Berichte*, 1936, 69, 12.

Analysis for $C_{27}H_{33}ClN_2O_3 \cdot C_2H_2O_4 \cdot 1.25\ H_2O$: Calculated: C, 59.89; H, 6.50; N, 4.82. Found: C, 59.85; H, 6.16; N, 4.81.

EXAMPLE 19

N-(1-[2-Chloro-9,10-dihydro-9,10-methanoanthracen-9-ylmethyl]-4-piperidyl)-2,2-diethoxyacetamide Using a procedure similar to that described in Example 6 except starting with 2,2-diethoxyacetic acid[2], the title compound was obtained as a white glassy solid (55%), mp 49.0°–51.0° C.; MS(CI): 469 (M+H); NMR (300 MHz, DMSO-$d_6$): 1.12(t, 6H, J=7.1 Hz), 1.47–1.60(br m, 4H), 2.26(m, 2H), 2.45(m, 2H), 2.95(br m, 2H), 3.29(d, 2H, J=14 Hz), 3.38(d, 1H, =14 Hz), 3.46–3.60(br m, 5H), 4.33(s, 1H), 4.66(s, 1H), 6.94(m, 3H), 7.20(m, 2H), 7.26(m, 2H), 7.64(d, 1H, J=8.3 Hz).

[2]2,2-Diethoxyacetic acid was obtained using a similar procedure as described in H. Scheibler and H.-J. Schmidt, *Berichte*, 1936, 69, 12.

Analysis for $C_{27}H_{33}ClN_2O_3$: Calculated: C, 69.14; H, 7.09; N, 5.97. Found: C, 69.15; H, 7.17; N, 5.90.

EXAMPLE 20

N-(1-[9,10-Dihydro-9,10-methanoanthracen-9-ylmethyl]-4-piperidyl)-2,2-diethoxyacetamide Using a procedure similar to that described in Example 8 except starting with 2,2-diethoxyacetic acid[2], the title compound was obtained as a white solid (20%), mp 109.5°–110.0° C.; MS(CI): 435 (M+H); NMR (300 MHz, DMSO-$d_6$): 1.12(t, 6H, J=7.0 Hz), 1.48–163(br m, 4H), 2.26(m, 2H), 2.45(s, 2H), 2.95(m, 2H), 3.34(s, submerged, 2H), 3.46–3.60(br m, 5H), 4.31(s, 1H), 4.66(s, 1H), 6.91(m, 4H), 7.18(d, 2H, J=7.1 Hz), 7.26(d, 2H, J=6.4 Hz), 7.63(d, 1H, J=8.3 Hz).

[2]2,2-Diethoxyacetic acid was obtained using a similar procedure as described in H. Scheibler and H.-J. Schmidt, *Berichte*, 1936, 69, 12.

Analysis for $C_{27}H_{34}N_2O_3 \cdot 0.25\ H_2O$: Calculated: C, 73.86; H, 7.92; N, 6.38. Found: C, 73.99; H, 7.86; N, 6.33.

EXAMPLE 21

N-(1-[2-Chloro-9,10-dihydro-9,10-methanoanthracen-9-ylmethyl]-4-piperidyl)-2-(isopropoxy)acetamide To a cooled (ice bath) stirred suspension of 97% sodium hydride (180 mg, 7.5 mmol) in N,N-dimethylformamide (3 mL) was added isopropanol (0.58 mL, 7.5 mmol). After stirring for 0.5 h at 0° C., the reaction was added 2-chloro-9-[4-(bromoacetamido)piperidinomethyl]methanoanthracene (575 mg, 1.25 mmol) and silver tetrafluoroborate (243 mg, 1.25 mmol). The reaction was allowed to warm to ambient temperature and stirred for an additional 18 h. The mixture was treated with water (50 mL) and methylene chloride (100 mL) and filtered through celite with methylene chloride (3×50 mL) washes. After separating the aqueous layer from the filtrate, the organic layer was washed with brine (50 mL), dried (sodium sulfate), filtered, and concentrated to give a yellow syrup. Chromatography of this material over silica gel (eluant: 9:1 methylene chloride/ether) gave the title compound as a light yellow glass (265 mg, 48%), mp 50.0°–3.0° C.; MS(CI): 439 (M+H); NMR (300 MHz,DMSO-$d_6$): 1.10(d, 6H, J=6.0 Hz), 1.51–1.61(br m, 4H), 2.26(br m, 2H), 2.47(m, 2H), 2.93(br m, 2H), 3.29(d, part. submerged by H2O, 1H), 3.38(d, 1H, J=14.1 Hz), 3.57(septet, 1H, J=6.2 Hz), 3.62(br m, 1H), 3.78(s, 1H), 4.34(s, 1H), 6.96(br m, 3H), 7.20(br d, 2H, J=8.9 Hz), 7.27(d, 2H, J=7.7 Hz), 7.34(d, 1H, J=8.0 Hz).

Analysis for $C_{26}H_{31}ClN_2O_2 \cdot 0.5\ H_2O$: Calculated: C, 69.71; H, 7.20; N, 6.25. Found: C, 69.85; H, 7.16; N, 6.11.

The starting 2-chloro-9,10-dihydro-9,10-methanoanthracen-9-ylmethyl]-4-piperidyl)-2-bromoacetamide was obtained as follows:

a. N-(1-[2-Chloro-9,10-dihydro-9,10-methanoanthracen-9-ylmethyl]-4-piperidyl)-2-bromoacetamide To a cold (ice bath) stirred solution of racemic 4-amino-1-[2-chloro-9,10-dihydro-9,10-methanoanthracen-9-ylmethyl]-piperidine (4.25 g, 12.54 mmol, described in Example 7b), diisopropyl ethylamine (4.37 mL, 25.08 mmol) in methylene chloride (75 mL) was added bromoacetyl bromide (1.36 mL, 15.68 mmol). After stirring the resulting mixture for 1 h at 0° C., the cooling bath was removed and the reaction was allowed to reach ambient temperature and stirred for an additional 18 h. The reaction mixture was treated with saturated sodium bicarbonate (2×150 mL) and brine (100 mL), dried (sodium sulfate), filtered, and concentrated to give the title compound as a brown foamy glass (5.74 g, quant.)

EXAMPLE 22

N-(1-[9,10-Dihydro-9,10-methanoanthracen-9-ylmethyl]-4-piperidyl)-3-phenylpropionamide Using a procedure similar to that described in Example 27 except starting with 4-amino-1-[9,10-dihydro-9,10-methanoanthracen-9-ylmethyl]piperidine (described in Example 8b) and 3-phenylpropionyl chloride, the title compound was obtained as a white solid (46%) by crystallization from ether-ethyl acetate, mp 149.0°–50.0° C.; MS(CI): 437 (M+H); NMR (300 Hz, DMSO-$d_6$): 1.20–1.40(m, 2H), 1.55–1.69(m, 2H), 2.17–2.40(m, 4H), 2.44(s, 2H), 2.79(t, 2H, J=8.1 Hz), 2.85–2.98(m, 2H), 3.33(m, 2H), 3.53(m, 1H), 4.30(s, 1H), 6.85–6.98(m, 4H), 7.10–7.32(m, 9H), 7.66(d, 1H, J=7.5 Hz).

Analysis for $C_{30}H_{32}N_2O$: Calculated: C, 82.53; H, 7.38; N, 6.41. Found: C, 82.32; H, 7.30; N, 6.34.

EXAMPLE 23

N-(1-[2-Chloro-9,10-dihydro-9,10-methanoanthracen-9-ylmethyl]-4-piperidyl)-3-phenylpropionamide Using a procedure similar to that described in Example 27 except starting with 3-phenylpropionyl chloride, the title compound was obtained as a white solid (74%), mp 73.0°–5.0° C.; MS(CI): 471 (M+H); NMR(300 MHz, DMSO-$d_6$): 1.20–1.40(m, 2H), 1.58–1.70(m, 2H), 2.18–2.38(m, 4H), 2.47(m, 2H), 2.79(t, 2H, J=7.8 Hz), 2.84–2.94(m, 2H), 3.32(m, 2H), 3.48–3.60(m, 1H), 4.33(s, 1H), 6.9–7.02(m, 3H), 7.12–7.32(m, 9H), 7.67(d, 1H, J=8.1 Hz).

Analysis for $C_{30}H_{31}ClN_2O \cdot 0.25\ H_2O$: Calculated: C, 75.77; H, 6.68; N, 5.89. Found: C, 75.71; H, 6.47; N, 5.86.

EXAMPLE 24

N-(1-[2-Chloro-9,10-dihydro-9,10-methanoanthracen-9-ylmethyl]-4-piperidyl)propionamide Using a procedure similar to that described in Example 27 except starting with propionyl chloride, the title compound was obtained as a white solid (53%), mp 147.0°–8.5° C.; MS(CI): 395 (M+H); NMR (300 MHz,DMSO-$d_6$): 0.96(t, 3H, J=7.5 Hz), 1.24–1.45(m, 2H), 1.58–1.75(m, 2H), 2.02(q, 2H, J=7.5 Hz), 2.16–2.35(m, 2H), 2.48(m, 2H), 2.85–3.00(m, 2H), 3.29(d, 1H, J=14.0 Hz), 3.37(d, 1H, J=14.0 Hz), 3.45–3.62(m, 1H), 4.33(s, 1H), 6.88–7.04(m, 3H), 7.15–7.34(m, 4H), 7.60(d, 1H, J=7.5 Hz).

Analysis for $C_{24}H_{27}ClN_2O$: Calculated: C, 72.99; H, 6.89; N, 7.09. Found: C, 72.63; H, 6.86; N, 7.01.

EXAMPLE 26

N-(1-[2-Chloro-9,10-dihydro-9,10-methanoanthracen-9-ylmethyl]-4-piperidyl)valeramide Using a procedure similar to that described in Example 6 except starting with valeric acid, the title compound was obtained as a white solid (71%) by crystallization from, mp 139.0°–40.0° C.; MS(CI): 423 (M+H): NMR (300 MHz, DMSO-$d_6$): 0.85(t, 3H, J=7.5 Hz), 1.24(sextuplet, 2H, J=6.0 Hz), 1.33(m, 2H), 1.45(q, 2H, J=6.0 Hz), 1.58–1.72(m, 2H), 2.02(t, 2H, J=6.0 Hz), 2.15–2.35(m, 2H), 2.48(m, 2H), 2.85–3.00(m, 2H), 3.29(d, 1H, J=14.0 Hz), 3.38(d, 1H, J=14.0 Hz), 3.53(m, 1H), 4.33(s, 1H), 6.88–7.00(m, 3H), 7.15–7.32(m, 4H), 7.62(d, 1H, J=7.5 Hz).

Analysis for $C_{26}H_{31}ClN_2O$: Calculated: C, 73.83; H, 7.39; N, 6.62. Found: C, 73.81; H, 7.35; N, 6.61.

EXAMPLE 27

N-(1-[2-Chloro-9,10-dihydro-9,10-methanoanthracen-9-ylmethyl]-4-piperidyl)-2-cyclopentylacetamide To a stirred cold (ice bath) solution of 4-amino-1-[2-chloro-9,10-dihydro-9,10-methanoanthracen-9-ylmethyl]piperidine (339 mg, 1 mmol, described in Example 7b) and pyridine (158 mg, 2 mmol) in methylene chloride (6.7 mL) was added cyclopentylacetyl chloride (161 mg, 1.1 mmol). After 15 min, the reaction was allowed to warm to ambient temperature and stirred for 18 h. The reaction was added methylene chloride (75 mL) and 1N sodium hydroxide (50 mL). The aqueous layer was extracted with methylene chloride (50 mL). The organic layers were combined and washed with 1N sodium hydroxide (2×50 mL), brine (35 mL) and dried (sodium sulfate). The solution was filtered and concentrated to give a foam. This material was chromatographed over silica gel (eluting in sequence with 1) methylene chloride; 2) 3:97 methanol:methylene chloride) and crystallized with ether to give the title compound as a white solid (323 mg, 72%), mp 149.5°–150.5° C.; MS(CI): 449 (M+H); NMR (300 MHz,DMSO-$d_6$): 1.02–1.17(m, 2H), 1.26–1.74(m, 10H), 2.01(d, 2H 2H, J=6.0 Hz), 2.09(m, 1H), 2.18–2.32(m, 2H), 2.47(m, 2H), 2.86–3.00(m, 2H), 3.28(d, 1H, J=14 Hz), 3.37(d, 1H, J=14 Hz), 3.54(m, 1H), 4.33(s, 1H), 6.89–7.00(m, 3H), 7.15–7.31(m, 4H), 7.61(d, 1H, J=7.7 Hz).

Analysis for $C_{28}H_{33}ClN_2O$: Calculated: C, 74.90; H, 7.41; N, 6.24. Found: C, 74.98; H, 7.47; N, 6.17.

EXAMPLE 28

N-(1-[2-Chloro-9,10-dihydro-9,10-methanoanthracen-9-ylmethyl]-4-piperidyl)-2-phenoxyacetamide Using a procedure similar to that described in Example 27 except starting with phenoxyacetyl chloride, the title compound was obtained as a white solid (66%), mp 80.0°–3.0° C.; MS(CI): 473 (M+H); NMR (300 MHz,DMSO-$d_6$): 1.40–1.60(m, 2H), 1.60–1.73(m, 2H), 2.20–2.38(m, 2H), 2.48(m, 2H), 2.87–3.03(m, 2H), 3.24–3.45(m, 2H), 3.60–3.75(m, 1H), 4.34(s, 1H), 4.30(s, 2H), 6.83–7.05(m, 6H), 7.74–7.40(m, 6H), 7.91(d, 1H, J=8.1 Hz).

Analysis for $C_{29}H_{29}ClN_2O_2 \cdot 0.25\ H_2O$: Calculated: C, 72.94; H, 6.23; N, 5.87. Found: C, 73.00; H, 6.13; N, 5.65.

EXAMPLE 29

N-(1-[2-Chloro-9,10-dihydro-9,10-methanoanthracen-9-ylmethyl]-4-piperidyl)-2-phenylacetamide Using a procedure similar to that described in Example 27 except starting with phenylacetyl chloride, the title compound was obtained as a light yellow solid (73%), mp 206.0°–8.5° C.; MS(CI): 457 (M+H); NMR (300 MHz, DMSO-$d_6$): 1.23–1.48(m, 2H), 1.62–1.75(m, 2H), 2.18–2.35(m, 2H), 2.42–2.55(m, 2H), 2.86–3.00(m, 2H), 3.25–3.44(m, 2H), 3.36(s, 2H), 3.46–3.612(m, 1H), 4.37(s, 1H), 6.88–7.02(m, 3H), 7.14–7.33(m, 9H), 7.95(d, 1H, J=7.5 Hz).

Analysis for $C_{29}H_{29}ClN_2O$: Calculated: C, 76.22; H, 6.40; N, 6.13. Found: C, 76.38; H, 6.32; N, 5.91.

EXAMPLE 30

N-(1-[9,10-Dihydro-9,10-methanoanthracen-9-ylmethyl]-4-piperidyl)-2-phenylacetamide Using a procedure similar to that described in Example 27 except starting with 4-amino-1-[9,10-dihydro-9,10-methanoanthracen-9-ylmethyl]piperidine (described in Example 8b) and phenylacetyl chloride, the title compound was obtained as a white solid (70%), mp 199.8°–202.1° C.; MS(CI): 423 (M+H); NMR (300 MHz,DMSO-$d_6$): 1.37(m, 2H), 1.67(m, 2H), 2.26(m, 2H), 2.45(s, 2H), 2.93(m, 2H), 3.36(s, 2H), 3.53(m, 1H), 4.30(s, 1H), 6.91(m, 4H), 7.17–7.28(m, 9H), 7.95(d, 1H, J=8.4 Hz).

Analysis for $C_{29}H_{30}N_2O \cdot 0.25\ H_2O$: Calculated: C, 81.55; H, 7.19; N, 6.56. Found: C, 81.61; H, 7.15; N, 6.43.

EXAMPLE 31

N-(1-[2-Chloro-9,10-dihydro-9,10-methanoanthracen-9-ylmethyl]-4-piperidyl)-2-(2-methoxyphenyl)acetamide Using a procedure similar to that described in Example 6 except starting with 2-methoxyphenylacetic acid, the title compound was obtained as a white solid (82%), mp 171.0°–2.0° C.; MS(CI): 487 (M+H); NMR (300 MHz, DMSO-$d_6$): 1.30–1.48(m, 2H), 1.62–1.76(m, 2H), 2.2–2.35(m, 2H), 2.48(m, 2H), 2.85–2.98(m, 2H), 3.25–3.42(m, 4H), 3.48–3.65(m, 1H), 3.74(s, 3H), 4.34(s, 1H), 6.80–7.00(m, 5H), 7.05(d, 1H, J=7.7 Hz), 7.10–7.32(m, 6H).

Analysis for $C_{30}H_{31}ClN_2O_2 \cdot 0.25\ H_2O$: Calculated: C, 73.31; H, 6.46; N, 5.70. Found: C, 73.40; H, 6.42; N, 5.53.

EXAMPLE 32

N-(1-[2-Chloro-9,10-dihydro-9,10-methanoanthracen-9-ylmethyl]-4-piperidyl)-2-(2-pyridyl)acetamide Using a procedure similar to that described in Example 6 except starting with 2-pyridylacetic acid hydrochloride, the title compound was obtained as a white solid (77%), mp 166.5°–7.5° C.; MS(CI): 458 (M+H); NMR (300 MHz, DMSO-$d_6$): 1.30–1.47(m, 2H), 1.63–1.73(m, 2H), 2.20–2.36(m, 2H), 2.47(m, 2H), 2.85–3.00(m, 2H), 3.24–3.42(m, 2H), 3.48–3.64(m, 1H), 3.57(s, 2H), 4.34(s, 1H), 6.88–7.00(m, 3H), 7.14–7.33(m, 6H), 7.71(t of t, 1H, J=7.5 Hz, J=1.9 Hz), 8.03(d, 1H, J=7.5 Hz), 8.46(d of d, 1H, J=4.8 Hz, J=0.8 Hz).

Analysis for $C_{28}H_{28}ClN_3O \cdot 0.25\ H_2O$: Calculated: C, 72.71; H, 6.21; N, 9.09. Found: C, 73.06; H, 6.17; N, 9.13.

EXAMPLE 33

N-(1-[2-Chloro-9,10-dihydro-9,10-methanoanthracen-9-ylmethyl]-4-piperidyl)-trans-3-(3-pyridyl)propenamide Using a procedure similar to that described in Example 6 except starting with trans-3-(3-pyridyl)propenic acid, the title compound was added obtained as a white solid (80%), mp 154.5°–6.5° C.; MS(CI): 470 (M+H); NMR (300 MHz, DMSO-$d_6$): 1.32–1.52(m, 2H), 1.68–1.85(m, 2H), 2.24–2.42(m, 2H), 2.43–2.57(m, 2H), 2.86–3.02(m, 2H), 3.28–3.46(m, 2H), 3.60–3.80(m, 1H), 4.34(s, 1H), 6.70(d, 1H, J=15.9 Hz), 6.88–7.04(m, 3H), 7.16–7.34(m, 4H), 7.44(d, 1H, J=16 Hz), 7.45(d of d, 1H, J=8.5 Hz, J=3.0 Hz), 7.96(d, 1H, J=7.9 Hz), 8.08(d, 1H, J=7.5 Hz), 8.54(d, 1H, J=4.6 Hz), 8.74(s, 1H).

Analysis for $C_{29}H_{28}ClN_3O$: Calculated: C, 74.11; H, 6.00; N, 8.94. Found: C, 74.23; H, 5.99; N, 8.82.

EXAMPLE 34

N-(1-[2-Chloro-9,10-dihydro-9,10-methanoanthracen-9-ylmethyl]-4-piperidyl)-3-(3-pyridyl)propionamide dihydrochloride To a stirred solution of N-(1-[2-chloro-9,10-dihydro-9,10-methanoanthracen-9-ylmethyl]-4-piperidyl)-trans-3-(3-pyridyl)propenamide (170 mg, 0.36 mmol) in ethanol (5 mL) was added 10% palladium on carbon (17 mg). This mixture was hydrogenated at 1 atmospheric pressure for 18 h. The reaction was filtered through diatomaceous earth. The filtrate as concentrated and the resulting residue was chromatographed over silica gel (eluant: 95:5 methylene chloride:methanol) to give a white foam. This material was dissolved in a cold (ice bath) solution of ether:chloroform (3:1, v/v, 15 mL) and treated with gaseous hydrochloric acid to afford the title compound as a white solid (100 mg, 52%), mp 220.0°–3.0° C.; (MS(CI): 472 (M+H); NNR (300 MHz, DMSO-$d_6$): 1.65–2.06(m, 4H), 2.46(t, 1.70H, J=7.5 Hz), 2.59(t, 0.3H, J=7.5 Hz), 2.73(m, 2H), 2.87–3.03(m, 2H), 3.17–3.66(m, 3H), 3.78(br m, 0.85H), 3.96(m, 0.15H), 4.18–4.40(m, 2H), 4.48(s, 1H), 6.95–7.10(m, 3H), 7.27–7.42(m, 3H), 7.48(s, 1H), 7.59–7.71(m, 1H), 8.02(d, 1H, J=7.5 Hz), 8.11(d, 1H, J=7.2 Hz), 8.35(br s, ~0.15H), 8.54–8.65(m, 2H), 8.68(br s, ~0.85H), 9.70(br s, 0.15H), 9.96–10.08(br s, 0.85H).

Analysis for $C_{29}H_{30}ClN_3O \cdot 2.0HCl$: Calculated: C, 63.92; H, 5.92; N, 7.71. Found: C, 63.67; H, 5.85; N, 7.51.

EXAMPLE 35

N-(1-[2-Chloro-9,10-dihydro-9,10-methanoanthracen-9-ylmethyl]-4-piperidyl)-3-(4-methoxyphenyl)propionamide hydrochloride Using a procedure similar to that described in Example 6 except starting with 3-(4-methoxyphenyl)propionic acid, the title compound was obtained as a white solid (82%), mp 270.0°–2.0° C.; MS(CI): 501 (M+H); NMR (300 MHz, DMSO-$d_6$): 1.68–2.08(m, 4H), 2.32(t, 1.6H, J=7.4 Hz), 2.45(t, 0.4H, J=7.1 Hz), 2.68–2.85(m, 4H), 3.34(m, submerged, 2H), 3.42–3.57(m, 2H), 3.70(s, 3H), 3.72–3.88(m, 0.8H), 3.88–4.00(m, 0.2H), 4.20–4.40(m, 2H), 4.48(s, 1H), 6.80–6.88(m, 2H), 6.95–7.20(m, 5H), 7.28–7.42(m, 3H), 7.49(m, 1H), 8.01(d, 0.8H, J=7.3 Hz), 8.19(d, 0.2H, J=6.2 Hz), 9.76(br s, 0.2H), 10.07(br s, 0.8H).

Analysis for $C_{31}H_{33}ClN_2O_2 \cdot 0.75\ H_2O$: Calculated: C, 67.57; H, 6.49; N, 5.08. Found: C, 67.56; H, 6.25; N, 5.09.

EXAMPLE 36

N-(1-[2-Chloro-9,10-dihydro-9,10-methanoanthracen-9-ylmethyl]-4-piperidyl)-2-(4-pyridylthio)acetamide Using a procedure similar to that described in Example 6 except starting with 4-(pyridylthio)acetic acid, the title compound was obtained as a white solid (76%), mp 160.0°–1.5° C.; MS(CI): 490 (M+H); NMR (300 MHz, DMSO-$d_6$): 1.30–1.46(m, 2H), 1.60–1.75(m, 2H), 2.20–2.36(m, 2H), 2.48(m, 2H), 2.83–2.98(m, 2H), 3.25–3.44(m, 2H), 3.50–3.65(m, 1H), 3.75(s, 2H), 4.34(s, 1H), 6.90–7.02(m, 3H), 7.14–7.33(m, 6H), 8.14(d, 1H, J=7.3 Hz), 8.36(d of d, 2H, J=4.6 Hz, J=1.5 Hz).

Analysis for $C_{28}H_{28}ClN_3OS$: Calculated: C, 68.62; H, 5.76; N, 8.58. Found: C, 68.65; H, 5.73; N, 8.62.

EXAMPLE 37

N-(1-[2-Chloro-9,10-dihydro-9,10-methanoanthracen-9-ylmethyl]-4-piperidyl)-2-methoxyacetamide Using a procedure similar to that described in Example 27 except starting with methoxyacetal chloride, the title compound was obtained as a white glassy solid (81%), mp 80.0°–4.0° C.; MS(CI): 411 (M+H); NMR (300 MHz, DMSO-$d_6$): 1.40–1.60(m, 4H), 2.18–2.36(m, 2H), 2.48(m, 2H), 2.88–3.02(m, 2H), 3.27(s, 3H), 3.29–3.42(m, submerged, 2H), 3.55–3.62(m, 1H), 3.75(s, 2H), 4.33(s, 1H), 6.88–7.03(m, 3H), 7.17–7.33(m, 4H), 7.57(d, 1H, J=8 Hz).

Analysis for $C_{24}H_{27}ClN_2O_2 \cdot 0.25\ H_2O$: Calculated: C, 69.39; H, 6.67; N, 6.74. Found: C, 69.16; H, 6.59; N, 6.45.

EXAMPLE 38

N-(1-[9,10-Dihydro-9,10-methanoanthracen-9-ylmethyl]-4-piperidyl)-2-isopropoxyacetamide Using a procedure similar to that described in Example 21 except starting with N-(1-[9,10-dihydro-9,10-methanoanthracen-9-ylmethyl]-4-piperidyl)-2-bromoacetamide and isopropanol, the title compound was obtained as a white solid (39%), mp 134.5°–5.5° C.; MS(CI): 405 (M+H); NMR (300 MHz, DMSO-$d_6$): 1.10(d, 6H, J=6.0 Hz), 1.52–1.61(br m, 4H), 2.28(br m, 2H), 2.46(s, 2H), 2.95(br m, 2H), 3.35(s, 2H), 3.58(septet, 1H, J=5.7 Hz), 3.65(br s, 1H), 3.78(s, 2H), 4.31(s, 1H), 6.92(br m, 4H), 7.19(d, 2H, J=7.0 Hz), 7.27(d, 2H), J=6.5 Hz), 7.34(d, 1H, J=8.0 Hz).

Analysis for $C_{26}H_{32}N_2 \cdot 0.25 H_2O$: Calculated: C, 76.34; H, 8.01; N, 6.85. Found: C, 76.51; H, 7.91; N, 6.86.

The starting N-(1-[9,10-dihydro-9,10-methanoanthracen-9-yl-methyl]-4-piperidyl)-2-bromoacetamide was prepared using a procedure similar to that described in Example 21a except starting with 4-amino-1-[9,10-dihydro-9,10-methanoanthracen-9-ylmethyl]piperidine (described in Example 8b).

EXAMPLE 39

N-(1-[9,10-Dihydro-9,10-methanoanthracen-9-ylmethyl]-4-piperidyl)- 2-cyclopentoxyacetamide Using a procedure similar to that described in Example 21 except starting with N-(1-[9,10-dihydro-9,10-methanoanthracen-9-ylmethyl]- 4-piperidyl)-2-bromoacetamide (described in Example 38a) and cyclopentanol, the title compound was obtained as a white solid (63%) mp 127.0°–8.0° C.; MS(CI): 431 (M+H); NMR (300 MHz, DMSO-$d_6$): 1.48 (br m, 4H), 1.62(br m, 8H), 2.8(br m, 2H), 2.45(s, 2H), 2.94(br m, 2H), 3.34(s, submerged, 2H), 3.60(br m, 1H), 3,74(2, 2H), 3.89(sextet, 1H, J=3.9 Hz), 4.30(s, 1H), 6.91(br m, 4H), 7.18(d, 2H, J=6.2 Hz), 7.26(d, 2H, J=6.2 Hz), 7.33(d, 1H, J=8.3 Hz).

Analysis for $C_{28}H_{34}N_2O_2 \cdot 0.25H_2O$: Calculated: C, 77.30; H, 7.99; N, 6.44 Found: C, 77.45; H, 7.85; N, 6.43

EXAMPLE 40

N-(1-[2-Chloro-9,10-dihydro-9,10-methanoanthracen-9-ylmethyl]-4-piperidyl)-2-cyclopentoxyacetamide Using a procedure similar to that described in Example 21 except starting with cyclopentanol, the title compound was obtained as a light yellow glass (43%), mp 45.0°–48.0° C.; MS(CI): 465 (M+H); NMR (300 MHz,DMSO-$d_6$): 1.49(br m, 4H), 1.62(br m, 8H), 2.27(br m, 2H), 2.48(m, 2H), 2.93(br m, 2H), 3.30(d, part. submerged by H2O, 1H), 3.38(d, 1H, J=14.3 Hz), 3.65(br m, 1H), 3.74(s, 2H), 3.89(m, 1H), 4.33(s, 1H), 6.95(br m, 3H), 7.20(d, 2H, J=8.4 Hz), 7.27(d, 2H, J=7.7 Hz), 7.35(d, 1H, J=8.2 Hz).

Analysis for $C_{28}H_{33}ClN_2O_2 \cdot 0.75H_2O$: Calculated: C, 70.28; H, 7.27; N, 5.85 found: C, 70.23; H, 7.23; N, 5.45

EXAMPLE 41

N-(1-[2-Chloro-9,10-dihydro-9,10-methanoanthracen-9-ylmethyl]-4-piperidyl)-2-(2-pyridyloxy)acetamide Using a procedure similar to that described in Example 21 except starting with 2-hydroxypyridine, the title compound was obtained as a white solid (48%), mp 225.0°–7.5° C.; MS(CI); 474 (M+H); NMR (300 MHz,DMSO-$d_6$): 1.38(br m, 2H), 1.67(br m, 2H), 2.28(m, 2H), 2.50(s, 2H), 2.92(br m, 2H), 3.30(d, part. submerged by H2O, 1H), 3.38(d, 1H, J=13.9 Hz), 3.55(br m, 1H), 4.34(s, 1H), 4.48(s, 2H), 6.18(t, 1H, J=6.7 Hz), 6.34(d, 1H, J=9.1 Hz), 6.94(br m, 3H), 7.19–7.29(br m, 4H), 7.41(t, 1H, J=8.6 Hz,), 7.56(d, 1H, J=6.3 Hz), 8.08(d, 1H, J=7.3 Hz).

Analysis for $C_{28}H_{28}ClN_3O_2 \cdot 0.25H_2O$: Calculated: C, 70.28; H, 6.00; N, 8.78 Found: C, 70.30; H, 5.91; N, 8.73

EXAMPLE 42

N-(1-[2-Chloro-9,10-dihydro-9,10-methanoanthracen-9-ylmethyl]-4-piperidyl)-2-(3-(2,3,4,5-tetrahydrofuran)oxy)acetamide oxalate Using a procedure similar to that described in Example 21 except starting with 3-hydroxytetrahydrofuran, the title compound was obtained as a white solid (39%), mp 2080°–210.0° C.; MS(CI): 467 (M+H); NMR (300 MHz, DMSO-$d_6$): 1.75(br m, 4H), 1.92(m, 2H), 2.58(s, 2H), 2.79(br m, 2H), 3.20(br m, 2H), 3.59–3.79(br m, 7H), 3.84(s, 2H), 4.16(br s, 1H), 4.40(s, 1H), 6.98(m, 3H), 7.30(m, 4H), 7.61(br d, 1H, J=7.7 Hz).

Analysis for $C_{27}H_{31}ClN_2O_3 \cdot C_2H_2O_2 \cdot 0.75H_2O$: Calculated: C, 61.05; H, 6.09; N, 4.91 Found: C, 60.88; H, 5.80; N, 4.84

EXAMPLE 43

N-[1-(2-Chloro-9,10-dihydro-9,10-methanoanthracen-9-ylmethyl)-4-piperidyl]-2-(2,3,4,5-tetrahydrofurfuryloxy)acetamide oxalate Using a procedure similar to that described in Example 21 except starting with 2-(hydroxymethyl)tetrahydrofuran, the title compound was obtained as a white solid (45%), mp 153.0–5.0(D) °C.; MS(CI): 481 (M+H); NMR (300 MHz, DMSO-$d_6$): 1.48–1.64(br m, 4H), 1.78– 1.90(br m, 4H), 2.57(s, 2H), 2.77(m, 2H), 3.20(m, 2H), 3.37(d of d, 1H, J=6.6 Hz, J=6.5 Hz), 3.48(d of d, 1H, J=3.6 Hz, J=3.7 Hz), 3.63–3.77(br m, 5H), 3.88(s, 2H), 3.97(m, 1H), 4.40(s, 1H), 6.97(m, 3H), 7.30(m, 4H), 7.66(d, 1H, J=7.9 Hz).

analysis for $C_{28}H_{33}ClN_2O_3 \cdot C_2H_2O_4 \cdot 0.75H_2O$: Calculated: C, 61.64; H, 6.29; N, 4.79 Found: C, 61.76; H, 6.08; N, 4.74

EXAMPLE 44

N-(1-[2-Chloro-9,10-dihydro-9,10-methanoanthracen-9-ylmethyl]-4-piperidyl)-2-t-butoxyacetamide oxalate Using a procedure similar to that described in Example 21 except starting with t-butanol, the title compound was obtained as a white solid (8%), mp 250.5°–8.0° C.;p MS(CI): 453 (M+H); NMR (300 MHz,DMSO-$d_6$): 1.15(s, 9H), 1.74(m, 4H), 2.57(s, 2H), 2.73(m, 2H), 3.18(m, 2H), 3.75(m, 5H), 4.04(s, 1H), 6.98(m, 3H), 7.24–7.38(br m, 5H).

Analysis for $C_{27}H_{33}ClN_2O_2 \cdot C_2H_2O_4 \cdot 1.5H_2O$: Calculated: C, 61.10; H, 6.72; N, 4.91 Found: C, 61.22; H, 6.83; N, 4.94

EXAMPLE 45

(2S)-N-(1-[2-Chloro-9,10-dihydro-9,10-methanoanthracen-9-ylmethyl]-4-piperidyl)-2-methoxy-2-phenylacetamide Using a procedure similar to that described in Example 6 except starting with (2S)-(+)-O-methylmandelic acid, the title compound was obtained as a white solid (56%), mp 125.5°–51.0° C.; MS(CI): 487 (M+H), NMR (300 MHz, DMSO-$d_6$): 1.75(m, 4H), 2.59(m, 2H), 2.85(m, 2H), 3.23(m, 2H), 3.80–4.97(m, 3H), 4.41(s, 1H), 4.63(s, 1H), 6.98(m, 3H), 7.26–7.37(m, 9H), 8.11(d, 1H, J=8.0 Hz).

Analysis for $C_{30}H_{31}ClN_2O_2 \cdot C_2H_2O_4 \cdot 2.0H_2O$: Calculated: C, 62.68; H, 6.08; N, 4.56 Found: C, 62.17; H, 5.45; N, 4.43

EXAMPLE 46

(2R)-N-(1-[2-Chloro-9,10-dihydro-9,10-methanoanthracen-9-ylmethyl]-4-piperidyl)-2-methoxy-2-phenylacetamide Using a procedure similar to that described in Example 6 except starting with (2R)-(−)-O-methylmandelic acid, the title compound was obtained as a white solid (37%), mp 141.0°–7.5° C.; MS(CI): 487 (M+H); NMR (300 MHz, DMSO-$d_6$): 1.55(m, 4H), 2.25(m, 2H), 2.45(m, 2H), 2.93(m, 2H), 3.25(br s, 3H), 3.3(m, 2H), 3.57(m, 1H), 4.33(s, 1H) 4.59(s, 1H), 6.90–6.96(m, 3H), 7.18–7.38(m, 9H), 7.90(d, 1H, J=8.1 Hz).

Analysis for $C_{30}H_{31}ClN_2O_2 \cdot HCl \cdot 1.25H_2O$: Calculated: C, 65.99; H, 6.37; N; 513 Found: C, 66.15; H, 6.09; N, 5.11

EXAMPLE 47

N-(1-[9,10-Dihydro-9,10-methanoanthracen-9-ylmethyl]-4-piperidyl)-2-( 2-chlorophenyl)acetamide Using a procedure similar to that described in Example 6 except starting with 4-amino-1-[9,10-dihydro-9,10-methanoanthracen- 9-ylmethyl]piperidine and 2-chlorophenylacetic acid, the title compound was obtained as a pink solid (71%), mp 212.0°–14.0° C.; MS(CI): 457 (M+H); NMR (300 MHz,DMSO-$d_6$): 1.38(m, 2H), 1.70(m, 2H), 2.28(m, 2H), 2.46(s, 2H), 2.93(m, 2H), 3.30(m, submerged, 2H), 3.54(m, 3H), 4.31(s, 1H), 6.87–6.96(m, 4H), 7.17–7.41(m, 8H), 7.96(d, 1H, J=7.7 Hz).

Analysis for $C_{29}H_{29}ClN_2O \cdot 0.25H_2O$: Calculated: C, 75.47; H, 6.44; N, 6.07 Found: C, 75.77; H, 6.35; N, 6.07

EXAMPLE 48

N-(1-[2-Chloro-9,10-dihydro-9,10-methanoanthracen-9-ylmethyl]-4-piperidyl)-2-(4-pyridyl)acetamide Using a procedure similar to that described in Example 6 except starting with 4-pyridylacetic acid hydrochloride, the title compound was obtained as a pink solid (13%), mp 190.5°–3.5° C.; MS(CI): 458 (M+H); NMR (300 MHz, DMSO-$d_6$): 1.37(m, 2H), 1.68(m, 2H), 2.27(m, 2H), 2.48(m, 2H), 2.92(m, 2H), 3.31(m, 2H), 3.42(br s, 2H), 3.54(m, 1H), 4.34(s, 1H), 6.94(m, 3H), 7.18–7.29(m, 6H), 8.06(d, 1H, J=7.6 Hz), 8.46(d, 2H), J=4.8 Hz).

Analysis for $C_{28}H_{28}ClN_3O \cdot 0.25H_2O$: Calculated: C, 72.71; H, 6.21; N, 9.09 Found: C, 72.48; H, 6.09; N, 9.09

EXAMPLE 49

N-(1-[2-Chloro-9,10-dihydro-9,10-methanoanthracen-9-ylmethyl]-4-piperidyl)-2-(1-methylimidazol-4-yl)acetamide Using a procedure similar to that described in Example 6 except starting with 3-methylimidazol-5-ylacetic acid hydrochloride, the title compound was obtained as a white solid (62%), mp 145.5°–51.5° C.; MS(CI): 461 (M+H); NMR (300 MHz,DMSO-$d_6$): 1.56(m, 2H), 1.80(m, 2H), 2.57(m, 2H), 2.78(m, 2H), 3.18(m, 2H), 3.42(m, submerged, 2H), 3.65–3.88(m, 6H), 4.41(s, 1H), 6.99(m, 3H), 7.16(s, 1H), 7.30(m, 4H) 8.10(d, 1H, J=6.9 Hz), 8.16 (s, 1H).

Analysis for $C_{27}H_{29}ClN_4O \cdot 2C_2H_2O_4 \cdot 1.25H_2O$, Calculated: C, 56.11; H, 5.39; N, 8.44 Found: C, 55.90; H, 5.11; N, 8.21

EXAMPLE 50

N-(1-[2-Chloro-9,10-dihydro-9,10-methanoanthracen-9-ylmethyl]-4-piperidyl)-2-ethoxypropionamide Using a procedure similar to that described in Example 6 except starting with 2-ethoxypropionic acid, the title compound was obtained as a white solid (49%), mp 135.5°–42.0° C.; MS(CI): 439 (M+H); NMR (400 MHz, DMSO-$d_6$): 1.12(t, 3H, J=5.3 Hz), 1.19(d, 3H, J=5.0 Hz), 1.70(m, 4H), 2.59(m, 2H), 2.83(m, 2H), 3.23(m, submerged by H2O, 2H), 3.40(m, 2H), 3.73(m, 3H), 3.86(m, 1H), 4.41(s, 1H), 6.98(m, 3H), 7.23–7.35(m, 4H), 7.73(d, 1H, J=4.6 Hz).

Analysis for $C_{26}H_{31}ClN_2O_2 \cdot C_2H_2O_4 \cdot H_2O$: Calculated: C, 61.48; H, 6.45; N, 5.12 Found: C, 61.54; H, 6.15; N, 4.99

EXAMPLE 51

N-(1-[9,10-Dihydro-9,10-methanoanthracen-9-ylmethyl)-4-piperidyl)-2-(2,2,2-trifluoroethoxy)acetamide Using a procedure similar to that described in Example 38a except starting with 2,2,2-trifluoroethanol, the title compound was obtained as a white solid (33%), mp 136.5°–9.0° C.; MS(CI): 445 (M+H); NMR (300 MHz, DMSO-$d_6$): 1.43(m, 2H), 1.64(m, 2H), 1.64 (m, 2H); 2.27(m, 2H), 2.45(s, 2H), 2.94(m, 2H), 3.33(m, 2H), 3.61(m, 1H), 4.03(s, 2H), 4.13(q, 2H, J=9.5 Hz), 4.31(s, 1H), 6.91(m, 4H), 7.17–7.28(m, 4H), 7.68(d, 1H, J=7.9 Hz).

Analysis for $C_{25}H_{27}F_3N_2O_2$: Calculated: C, 67.55; H, 6.12; N, 6.30 Found: C, 67.39; H, 6.22; N, 6.28

EXAMPLE 52

N-(1-[2-Chloro-9,10-dihydro-9,10-methanoanthracen-9-ylmethyl]-4-piperidyl)-2-(2,2,2-trifluoroethoxy)acetamide Using a procedure similar to that described in Example 21 except starting with 2,2,2-trifluoroethanol, the title compound was obtained as a light tan solid (41%), mp 119.0°–23.0° C.; MS(CI): 479 (M+H); NMR (300 MHz, DMSO-$d_6$): 1.45(m, 2H), 1.66(m, 2H), 2.27(m, 2H), 2.93(m, 2H), 3.33(m, 2N), 3.62(m, 1H), 4.04(s, 2H), 4.14(q, 2H, J=9.3 Hz), 4.34(s, 1H), 6.95(m, 3H), 7.18–7.28(m, 4H), 7.69(d, 1H, J=8.0 Hz).

Analysis for $C_{25}H_{26}ClF_3N_2O_2$: Calculated: C, 62.70; H, 5.47; N, 5.85 Found: C, 62.80; H, 5.60; N, 5.63

EXAMPLE 53

N-(1-[2-Chloro-9,10-dihydro-9,10-methanoanthracen-9-ylmethyl]-4-piperidyl)-2-(2-fluoroethoxy)acetamide Using a procedure similar to that described in Example 21 except starting with 2-fluoroethanol, the title compound was obtained as a white solid (37%), mp 179.5°80.5° C.; MS(CI): 443 (M+H); NMR (300 MHz,DMSO-$d_6$): 1.55–1.87(m, 4H), 2.59(m, 2H), 3.24(m, 2H), 3.65(m, 1H), 3.74(m, 1H), 3.91(s, 2H), 4.41(s, 1H), 4.49(m, 1H), 4.65(m, 1H), 6.99(m, 3H), 7.25–7.35(m, 4H), 7.70(m, 1H).

Analysis for $C_{25}H_{28}ClFN_2O_2 \cdot C_2H_2O_4 \cdot 1.25H_2O$: Calculated: C, 58.38; H, 5.89; N, 5.04 Found: C, 58.34; H, 5.44; N, 4.84

EXAMPLE 54

N-(1-[9,10-Dihydro-9,10-methanoanthracen-9-ylmethyl]-4-piperidyl)-2-(2-pyridyl)acetamide Using a procedure similar to that described in Example 6 except starting with 4-amino-1-[9,10-dihydro-9,10-methanoanthracen-9-ylmethyl]piperidine and 2-(2-pyridyl)acetic acid hydrochloride, the title compound was obtained as a white solid (72%), mp 176.0°14 7.5° C.; MS(CI): 424 (M+H); NMR (300 MHz,DMSO-$d_6$): 1.37(m, 2H), 1.69(m, 2H), 2.27(m, 2H), 2.45(s, 2H), 2.93(m, 2H), 3.34(m, 2H), 3.57 (m, 3H), 4.31(s, 1H), 6.92(m, 4H), 7.17–7.31(m, 6H), 7.71(t, 1H, J=7.7 Hz), 8.02(d, 1H, J=7.7 Hz), 8.45(m, 1H).

Analysis for $C_{28}H_{29}H_3O$: Calculated: C, 79.40; H, 6.90; H, 9.92 Found: C, 79.49; H, 6.94; N, 9.95

EXAMPLE 55

N-(1-[9,10-Dihydro-9,10-methanoanthracen-9-ylmethyl]-4-piperidyl)- 2,2-dimethylpropionamide Using a procedure similar to that described in Example 27 except starting with 4-amino-1-[9,10-dihydro-9,10-methanoanthracen- 9-ylmethyl]piperidine and pivaloyl chloride, the title compound was obtained as a white solid (87%), mp 181.5°–2.5° C.; MS(CI): 389 (M+H); NMR (300 MHz, DMSO-$d_6$): 1.05(s, 9H), 1.37–1.66(m, 4H), 2.24(m, 2H), 2.45(s, 2H), 2.97(m, 2H), 3.31(s, 2H), 3.56(m, 1H), 4.30(s, 1H), 6.91(m, 4H), 7.06(d, 1H, J=8.1 Hz), 7.17–7.27(m, 4H).

Analysis for $C_{26}H_{32}N_2O$: Calculated: C, 80.37; H, 8.30; N, 7.26 Found: C, 80.34; H, 8.19; N, 7.36

EXAMPLE 56

N-(1-[2-Chloro-9,10-dihydro-9,10-methanoanthracen-9-ylmethyl]-4-piperidyl)-2,2-dimethylpropionamide Using a procedure similar to that described in Example 27 except starting with pivaloyl chloride, the title compound was obtained as a white solid (60%), mp 191.5°–3.0° C.; MS(CI): 423 (M+H): NMR (300 MHz,DMSO-$d_6$): 1.17(s, 9H), 1.41(m, 2H), 1.86(m, 2H), 2.37(m, 2H), 2.57(m, 2H), 2.94(m, 2H), 3.34(m, 2H), 3.79(m, 1H), 4.24(s, 1H), 5.42(d, 1H, J=7.3 Hz), 6.86–6.99(m, 3H), 7.10–7.27(m, 4H).

Analysis for $C_{26}H_{31}ClN_2O \cdot 0.1H_2O$ Calculated: C, 73.51; H, 7.40; N, 6.59 Found: C, 73.33; H, 7.40; N, 6.48

EXAMPLE 57

N-(1-[9,10-Dihydro-9,10-methanoanthracen-9-ylmethyl]-4-piperidyl)-2-(2-methoxyethoxy)acetamide Using a procedure similar to that described in Example 38 except starting with 2-methoxyethanol, the title compound was obtained as a white solid (15%), mp 119.0°–22.0° C.; MS(CI): 421 (M+H); NMR (300 MHz,DMSO-$d_6$): 1.43(m, 2H), 1.65(m, 2H), 2.29(m, 2H), 2.46(s, 2H), 2.94(m, 2H), 3.25(s, 3H), 3.34(m, submerged by H$_2$O, 2H), 3.47(m, 2H), 3.55(m, 2H), 3.83(s, 2H), 4.31(s, 2H), 6.91(m, 4H), 7.17–7.28(m, 4H), 7.48(d, 1H, J=8.3 Hz).

Analysis for $C_{26}H_{32}N_2O_3 \cdot 0.25H_2O$: Calculated: C, 73.47; H, 7.71; N, 6.59 Found: C, 73.60; H, 7.54; N, 6.59

EXAMPLE 58

N-(1-[2-Chloro-9,10-dihydro-9,10-methanoanthracen-9-ylmethyl]- 4-piperidyl)-picolinamide Using a procedure similar to that described in Example 6 except starting with picolinic acid, the title compound was obtained as a white solid (75%), mp 151.0°–2.0° C.; MS(CI): 444 (M+H); NMR (300 MHz,DMSO-$d_6$): 1.55–1.84(m, 4H), 2.24–2.44(m, 2H), 2.50(m, submerged by DMSO, 2H), 2.90–3.10(m, 2H), 3.34–3.48(m, part, submerged by H$_2$O, 2H), 3.74–3.91(m, 1H), 4.35(s, 1H), 6.88–7.06(m, 3H), 7.15–7.36(m, 4H), 7.59(m, 1H), 7.94–8.08(m, 2H), 8.54(d, 1H, J=8.2 Hz), 8.62(d, 1H, J=4.5 Hz).

Analysis for $C_{27}H_{26}ClN_3O$: Calculated: C, 73.04; H, 5.90; N, 9.47 Found: C, 73.00; H, 5.90; N, 9.59

EXAMPLE 59

N-(1-[2Chloro-9,10-dihydro-9,10-methanoanthracen-9-ylmethyl]- 4-piperidyl)isonicotinamide Using a procedure similar to that described in Example 6 except starting with isonicotinic acid, the title compound was obtained as a white solid (72%), mp 205.5°–7.5° C.; MS(CI): 444 (M+H); NMR (300 MHz,DMSO-$d_6$): 1.48–1.66(m, 2H), 1.70–1.84(m, 2H), 2.20– 2.40(m, 2H), 2.50(m, 2H), 2.94–3.10(m, 2H), 3.33(d, part. submerged by H$_2$O, J=14.0 Hz), 3.42(d, 1H, J=14.0 Hz), 3.73–3.90(m, 1H), 4.34(s, 1H), 6.88–7.02(m, 3H), 7.18–7.32(m, 4H), 7.73(d, 2H, J=6.0 Hz), 8.49(d, 1H, J=7.8 Hz), 8.69(d, 2H, J=6.0 Hz).

Analysis for $C_{27}H_{26}ClN_3O$: Calculated: C, 73.04; H, 5.90; N, 9.47 Found: C, 72.67; H, 5.87; N, 9.34

EXAMPLE 60

N-(1-[9,10-Dihydro-9,10-methanoanthracen-9-ylmethyl]-4-piperidyl)-2-(4-tetrahydropyranyloxy)acetamide Using a procedure similar to that described in Example 38a except starting with 4-hydroxytetrahydropyran, the title compound was obtained as a white solid (13%), mp 130.5°–134.5° C.; MS(CI): 447 (M+H); NMR (300 MHz, DMSO-$d_6$): 1.37–1.64(m, 6H), 1.83(m, 2H), 2.27(m, 2H), 2.45(s, 2H), 2.95(m, 2H), 3.25–3.34(m, submerged by H2O, 4H), 3.50(m, 1H), 3.63(m, 1H), 3.76–3.84(m, 4H), 4.31(s, 1H), 6.91(m, 4H), 7.17–7.28(m, 4H).

Analysis for $C_{28}H_{34}N_2O_3 \cdot 0.25H_2O$: Calculated: C, 74.55;

H, 7.71; N, 6.21 Found: C, 74.73; H, 7.65; N, 6.10

EXAMPLE 61

1-[1-(9,10-Dihydro-9,10-methanoanthracen-9-ylmethyl)-4-piperidyl]- 3-(cyclopentylmethyl)urea To a cold (ice bath) stirred solution of cyclopentylmethylamine (664 mg, 6.70 mmol) in methylene chloride (5 mL) was added [(9,10-dihydro-9,10-methanoanthracen-9-ylmethyl)-4-piperidyl]isocyanate hydrochloride (221 mg, 0.67 mmol). After stirring the resulting mixture for 0.5 h, at 0° C., the cooling bath was removed and the reaction was allowed to reach ambient temperature. After stirring for 18 h, the reaction mixture was treated with 1N sodium hydroxide and extracted with methylene chloride (2×50 mL). The combined extracts was washed with 1N sodium hydroxide (2×50 mL) and brine (50 mL), dried (sodium sulfate), and concentrated to give a tan syrup. Chromatography of this material over silica gel (eluant: 98:2 methylene chloride:methanol) affords a white foam. This was triturated with hot ether to provide the title compound as a white solid (101 mg, 35%), mp 197.0°–8.0° C.; MS(CI): 430 (M+H); NMR (300 MHz,DMSO-$d_6$): 1.05–1.35(m, 4H), 1.38–1.78(m, 8H), 1.89(quinlet, 1H, J=7.3 Hz), 2.20–2.36(m, 2H), 2.45(s, 2H), 2.78–2.95(m, 4H), 3.26– 3.42(m, submerged, 3H), 4.30(s, 1H), 5.66(d, 1H, J=7.5 Hz), 5.73(t, 1H, J=5.5 Hz), 6.84–6.99(m, 4H), 71.8(d, 2H, J=6.4 Hz), 7.26(d, 2H, J=6.9 Hz).

Analysis for $C_{28}H_{35}N_3O$: Calculated: C, 78.28; H, 8.21; N, 9.78 Found: C, 78.02; H, 8.14; N, 9.50

The starting material isocyanate was prepared as follows:

a)
[(9,10-Dihydro-9,10-methanoanthracen-9-ylmethyl)-4-piperidyl]-isocyanate hydrochloride To a stirred suspension of triphosgene (9.74 g, 32.82 mmol) in methylene chloride (75 mL) was slowly added Example 8b in methylene chloride (30 mL). After heating to reflux for 18 h, the reaction was cooled. The resulting suspension was filtered off. Hexane (500 mL) was added to the filtrate and filtration of the resulting suspension afforded the title compound as a white solid (8.59 g, 71%), mp 245.0–50.0 C (D); MS(CI): 331 (M+H); NMR (300 MHz, DMSO-$d_6$): 1.97 (m, 2H), 2.17(m, 2H), 2.70(s, 2H), 3.38–3.59(br m, 4H), 3.86(br s, 1H), 4.37– 4.44(br m, 2H), 4.46(s, 1H), 6.98(m, 4H), 7.34(m, 4H), 9.80(br s, 1H).

EXAMPLE 62

1-[1-(2-Chloro-9,10-dihydro-9,10-methanoanthracen-9-ylmethyl)- 4-piperidyl]-3-(propyl)urea Using a procedure similar to that described in Example 76 except starting with 7b and propylisocyanate, the title compound was obtained as a white solid (80%) by crystallization from, mp 178.0°– 181.0° C.; MS(CI): 424 (M+H); NMR (300 MHz,DMSO-$d_6$): 0.82(t, 3H, J=7.4 Hz), 1.18–1.42(m, 4H), 1.60–1.78(m, 2H), 2.18–2.36(m, 2H), 2.47(m, 2H), 2.76–2.98(m, 4H), 3.20–3.44(m, 3H), 4.33(s, 1H), 5.60–5.78(m, 2H), 6.85–7.04(m, 3H), 7.15–7.35(m, 4H).

Analysis for $C_{25}H_{30}ClN_3O$: Calculated: C, 70.82; H, 7.13; N, 9.91 Found: C, 70.85; H, 7.16; N, 9.91

EXAMPLE 63

1-[1-(9,10-Dihydro-9,10-methanoanthracen-9-ylmethyl)-4-piperidyl]-3-( 2-pyridylmethyl)urea Using a procedure similar to that described in Example 61 except starting with 2-pyridylmethylamine, the title compound was obtained as a white solid (20%), mp 189.0°–190.0° C.; MS(CI): 439 (M+H); NMR (300 MHz, DMSO-$d_6$): 1.22–1.40(m, 2H), 1.65–1.78(m, 2H), 2.22–2.36(m, 2H), 2.46(s, 2H), 2.82–2.94(m, 2H), 3.33(s, submerged, 2H), 3.30–3.48(m, 1H), 4.27(s, 1H), 4.30(d, 2H, J=3.5 Hz), 6.06(d, 1H, J=7.9 Hz), 6.36(d, 1H, J=5.5 Hz), 6.85–6.98(m, 4H), 7.13–7.30(m, 6H), 7.75(d of t, 1H, J=7.7 Hz, J=1.7 Hz), 8.48(d, 1H, J=4.8 Hz).

Analysis for $C_{28}H_{30}N_4O$: Calculated: C, 76.68; H, 6.89; N, 12.78 Found: C, 76.67; H, 6.90; N, 12.73

EXAMPLE 64

1-[1-(9,10-Dihydro-9,10-methanoanthracen-9-ylmethyl)-4-piperidyl]-3-( 4-pyridylmethyl)urea Using a procedure similar to that described in Example 61 except starting with 4-pyridylmethylamine, the title compound was obtained as a white solid (20%), mp 191.0°2.5° C.; MS(CI): 439 (M+H); NMR (300MHz,DMSO-$d_6$): 1.24–1.45(m, 2H), 1.66–1.82(m, 2H), 2.20– 2.38(m, 2H), 2.46(s, 2H), 2.82–3.00(m, 2H), 3.26–3.48(m, submerged, 3H), 4.21(d, 2H, J=5.8 Hz), 4.31(s, 1H), 5.97(br d, 1H, J=8.0 Hz), 6.36(br t, 1H, J=6 Hz), 6.85–7.03(m, 4H), 7.13–7.35(m, 6H), 8.47(d, 2H, J=6 Hz).

Analysis for $C_{28}H_{30}N_4O$: Calculated: C, 76.68; H, 6.89; N, 12.78 Found: C, 76.34; H, 6.83; N, 12.71

EXAMPLE 65

1-[1-(9,10-Dihydro-9,10-methanoanthracen-9-ylmethyl)-4-piperidyl]-3-( 2-phenylethyl)urea Using a procedure similar to that described in Example 76 except starting with 2-phenylethyl isocyanate, the title compound was obtained as a white solid (77%), mp 168.0°–70.5° C.; MS(CI): 452 (M+H); NMR (300 MHz, DMSO-$d_6$): 1.26(m, 2H), 1.68(m, 2H), 2.28(m, 2H), 2.45(s, 2H), 2.66(t, 2H, J=7.4 Hz), 2.87(m, 2H), 3.20(q, 2H, J=6.8Hz), 3.33(m, 3H), 4.30(s, 1H), 5.72(t, 1H, J=5.79), 5.78(d, 1H, J=7.9Hz), 6.87–6.95(m, 4), 7.17–7.31(m, 9H).

Analysis for $C_{30}H_{33}N_3O \cdot 0.6H_2O$: Calculated: C, 77.92; H, 7.45; N, 9.09 Found: C, 77.87; H, 7.41; N, 9.06

EXAMPLE 66

1-[1-(2-Chloro-9,10-dihydro-9,10-methanoanthracen-9-ylmethyl)-4-piperidyl]- 3-(benzyl)urea Using a procedure similar to that described in Example 76 except starting with 7b and benzyl isocyanate, the title compound was obtained as a white solid (66%), mp 185.0°–7.5° C.; MS(CI); 472 (M+H); NMR (300 MHz, DMSO-$d_6$): 1.30(m, 2H), 1.70(m, 2H), 2.29(m, 2H), 2.47(m, 2H), 2.87(m, 2H), 3.35(m, submerged by $H_2O$, 3H), 4.18(d, 2H, J=6.0 Hz), 4.33(s, 1H), 5.85(d, 1H, J=8.0 Hz), 6.21(t, 1H, J=6.0 Hz), 6.90– 6.98(m, 3H), 7.19–7.33(m, 9H).

Analysis for $C_{29}H_{30}ClN_3O \cdot 0.4H_2O$: Calculated: C, 72.68; H, 6.48; N, 8.77 Found: C, 72.79; H, 6.26; N, 8.47

EXAMPLE 67

1-[1-(2-Chloro-9,10-dihydro-9,10-methanoanthracen-9-ylmethyl)-4-piperidyl]-3-(4-pyridylmethyl)urea Using a procedure similar to that described in Example 78 except starting with 7b and 4-pyridylmethyl amine, the title compound was obtained as a white solid (13%), mp 165.5°–74.0° C.; MS(CI): 473 (M+H); NMR (300 MHz, DMSO-$d_6$): 1.32(m, 2H), 1.70(m, 2H), 2.29(m, 2H), 2.48(m, 2H), 2.88(m, 2H), 3.37(m, submerged, 3H), 4.21(d, 2H, J=6.0 Hz), 4.33(s, 1H), 5.98(d, 1H, J=7.8 Hz), 6.36(t, 1H, J=6.0 Hz), 6.92– 6.97(m, 3H), 7.17–7.29(m, 6H), 8.47(d, 2H, J=5.8 Hz).

Analysis for $C_{28}H_{29}ClN_4O.0.5H_2O$: Calculated: C, 69.77; H, 6.27; N, 11.62 Found: C, 69.90; H, 6.28; N, 11.23

EXAMPLE 68

1-[1-(2-Chloro-9,10-dihydro-9,10-methanoanthracen-9-ylmethyl)-4-piperidyl]-3-(2-tetrahydrofuranylmethyl)urea Using a procedure similar to that described in Example 78 except the reaction was performed at ambient temperature and starting with 7b and 2-tetrahydrofuranylmethyl amine (5.0 equiv), the title compound was obtained as a white solid (27%), mp 156.5°–9.5° C.; MS(CI): 466 (M+H); NMR (300 MHz, DMSO-$d_6$): 1.25(m, 2H), 1.44(m, 1H), 1.66– 1.84(m, 5H), 2.30(m, 2H), 2.47(m, 2H), 2.84–3.00(m, 3H), 3.08(m, 1H), 3.30(m, submerged 3H), 3.60(m, 1H), 3.72(m, 2H), 4.33(s, 1H), 5.75(t, 1H, J=5.9 Hz), 5.85(d, 1H, J=7.4 Hz), 6.91–6.98(m, 3H), 7.18–7.28(m, 4H).

Analysis for $C_{27}H_{32}ClN_3O_2.0.25H_2O$: Calculated: C, 68.92; H, 6.96; N, 8.93 Found: C, 68.73; H, 6.92; N, 8.71

EXAMPLE 69

1-[1-(9,10-methanoanthracen-9-ylmethyl)-4-piperidyl]-3-(cyclopentyl)urea

Using a procedure similar to that described in Example 61 except starting with cyclopentylamine, the title compound was obtained as a white solid (8%), mp 117.8°–21.6° C.; MS(CI): 416 (M+H); NMR (300 MHz, DMSO-$d_6$): 1.15–1.30(m, 4H), 1.40–1.85(m, 8H), 2.27(m, 2H), 2.44(m, 2H), 2.85(m, 2H), 3.30(m, submerged, 3H), 3.80(m, 1H), 4.30(s, 1H), 5.55(d, 1H, J=8.7 Hz), 5.71(d, 1H, J=8.9 Hz), 6.91(m, 4H), 7.18– 7.28(m, 4H).

Analysis for $C_{27}H_{33}N_3O.0.25H_2O$: Calculated: C, 77.19; H, 8.04; N, 10.00 Found: C, 76.97; H, 7.83; N, 9.77

EXAMPLE 70

1-[1-(9,10-Dihydro-9,10-methanoanthracen-9-ylmethyl)-4-piperidyl]-3-(cyclohexylmethyl)urea Using a procedure similar to that described in Example 61 except starting with cyclohexylmethlamine, the title compound was obtained as a white solid (12%), mp 198.5°–202.1° C.; MS(CI): 444 (M+H); NMR (300 MHz, DMSO-$d_6$): 0.83(m, 2H), 1.06–1.31(m, 6H), 1.06–1.31 (m, 6H), 1.58–1.73(m, 7H), 2.28(m, 2H), 2.45(s, 2H), 2.78–2.89(m, 4H), 3.32(m, submerged, 3H), 4.30(s, 1H), 5.13(d, 1H), J=7.8 Hz), 5.73(t, 1H, J=5.9 Hz), 6.86– 6.96(m, 4H), 7.16–7.27(m, 4H).

Analysis for $C_{29}H_{37}N_3O.0.3H_2O$: Calculated: C, 77.57; H, 8.44; N, 9.36 Found: C, 77.53; H, 8.38; N, 9.23

EXAMPLE 71

1-[1-(9,10-Dihydro-9,10-methanoanthracen-9-ylmethyl)-4-piperidyl]-3-(cyclohexyl)urea Using a procedure similar to that described in Example 76 except starting with cyclohexylisocyanate, the title compound was obtained as a white solid (64%), mp 228.3°30.5° C.; MS(CI): 430 (M+H); NMR (300 MHz,DMSO-$d_6$): 1.02–1.30(m, 7H), 1.49(m, 1H), 1.54–1.72(m, 7H), 2.28(m, 2h), 2.45(s, 2H), 2.87(m, 2H), 3.30–3.37(m, submerged by H2O, 4H), 4.30(s, 1H), 5.61(t, 2H, J=7.6 Hz), 6.36–6.86(m, 4H), 7.16– 7.27(m, 4H).

Analysis for $C_{28}H_{35}N_3O.0.25H_2O$ Calculated: C, 77.47; H, 8.24; N, 9.68 Found: C, 77.53; H, 7.92; N, 9.65

EXAMPLE 72

1-[1-(9,10-Dihydro-9,10-methanoanthracen-9-ylmethyl)-4-piperidyl]-3-(benzyl)urea Using a procedure similar to that described in Example 76 except starting with benzylisocyanate, the title compound was obtained as a white solid (87%), mp 200.5°–4.1° C.; MS(CI): 438 (M+H); NMR (300 MHz,DMSO-$d_6$): 1.29(m, 2H), 1.71(m, 2H), 2.29(t, 2H, J–11 Hz), 2.45(s, 2H), 2.87(m, 2H), 3.31(s, 2H), 3.40(m, 1H), 4.18(d, 2H, J=6.0 Hz), 4.30(s, 1H), 5.84(d, 1H, J=7.7 Hz), 6.21(t, 1H, J=6.0 Hz), 6.87– 6.95(m, 4H), 7.17–7.33(m, 9H).

Analysis for $C_{29}H_{31}N_3O.0.25H_2O$: Calculated: C, 78.78; H, 7.18; N, 9.50 Found: C, 78.78; H, 7.24; N, 9.46

EXAMPLE 73

1-[1-(9,10-Dihydro-9,10-methanoanthracen-9-ylmethyl)-4-piperidyl]-3-(phenyl)urea Using a procedure similar to that described in Example 76 except starting with phenylisocyanate, the title compound was obtained as a white solid (84%), mp 243.0°–5.0° C.; MS(CI): 424 (M+H); NMR (300 MHz,DMSO-$d_6$): 1.36(m, 2H), 1.76(m, 2H), 2.34(m, 2H), 2.47(s, 2H), 2.90(m, 2H), 3.36(s, 2H), 3.50(m, 1H), 4.31(s, 1H), 6.06(d, 1H, J=7.5 Hz), 6.85–6.96(m, 6H), 7.18–7.28(m, 6H), 7.36(d, 1H, J=7.7 Hz), 8.33(s, 1H).

Analysis for $C_{28}H_{29}N_3O$: Calculated: C, 78.56; H, 6.95; N, 9.82 Found: C, 78.86; H, 7.03; N, 9.74

EXAMPLE 74

1-[1-(9,10-Dihydro-9,10-methanoanthracen-9-ylmethyl)-4-piperidyl]-3-(2-tetrahydrofuranylmethyl)urea Using a procedure similar to that described in Example 61 except starting with 2-tetrahydrofuranylmethylamine, the title compound was obtained as a white solid (7%), mp 202.5°–4.5° C.; MS(CI): 432 (M+H); NMR (250 MHz, DMSO-$d_6$): 1.25(m, 2H), 1.45(m, 1H), 1.60– 1.90(m, 5H), 2.30(m, 2H), 2.45(s, 2H), 2.83–3.17(m, 4H), 3.30(m, 3H), 3.60(m, 1H), 3.75(m, 2H), 4.30(s, 1H), 5.66–5.85(m, 2H), 6.91(m, 4H), 7.16–7.27(m, 4H).

Analysis for $C_{26}H_{33}N_3O_2.0.5H_2O$: Calculated: C, 73.61; H, 7.78; N, 9.54 Found: C, 73.50; H, 7.84; N, 9.30

EXAMPLE 75

1-[1-(2-Chloro-9,10-dihydro-9,10-dihydro-9,10-methanoanthracen-9-ylmethyl)-4-piperidyl]-3-(2-tetrahydropyranyl)urea Using a procedure similar to that described in Example 76 except starting with 7b and 2-tetrahydropyranylisocyanate, the title compound was obtained as a white solid (60%), mp 189.05°–91.5° C.; MS(CI): 466 (M+H); NMR (300 MHz, DMSO-$d_6$): 1.20–1.82(m, 11H), 2.29(m, 2H), 2.47(s, 2H), 2.83(m, 2H), 3.32(m, submerged, 3H), 3.74(m, 1H), 4.33(s, 1H), 4.71(t, 1H, J=9.5 Hz), 5.83(d, 1H, J=6.0 Hz), 6.39(d, 1H, J=9.4 Hz), 6.94(m, 3H), 7.18–7.28(m, 4H).

Analysis for $C_{27}H_{32}ClN_3O_2$: Calculated: C, 69.59; H, 6.92; N, 9.02 Found: C, 69.40; H, 6.85; N, 8.83

EXAMPLE 76

1-[1-(9,10-Dihydro-9,10-methanoanthracen-9-ylmethyl]-4-piperidyl]- 3-(2-tetrahydropyranyl)urea To a cold (ice bath) stirred solution of Example 8b (565 mg, 1.85 mmol) in methylene chloride (9.3 mL) was added 2-tetrahydropyranylisocyanate (0.24 mL, 2.04 mmol). After stirring for 18 h, the mixture was filtered to give a small amount of the product. The filtrate was added methylene chloride (75 mL). The solution was washed with saturated solution bicarbonate (2×7 mL), water (3×20 mL), brine (20 mL) and dried (sodium sulfate). This solution was concentrated and triturated with ether (20 mL) to give more of the product. This sample was combined with the material from above to give the title compound as a white solid (696 mg, 86%), mp 211.0°1.5° C.; MS(CI): 432 (M+H); NMR (300 MHz,DMSO-$d_6$): 1.20–1.81(m, 11H), 2.30(m, 2H), 2.45(s, 2H), 2.86(m, 2H), 3.36(m, 3H), 3.73(m, 1H), 4.30(s, 1H), 4.70(m, 1H), 5.83(d, 1H, J=7.6 Hz), 6.38(d, 1H, J=9.6 Hz), 6.91(m, 4H), 7.16–7.28(m, 4H).

Analysis for $C_{27}H_{33}N_3O_2.0.25H_2O$: Calculated: C, 74.37; H, 7.74; N, 9.64 Found: C, 74.54; H, 7.57; N, 9.48

EXAMPLE 77

Ethyl N-(1-[2-chloro-9,10-dihydro-9,10-methanoanthracen-9-yl-methyl]- 4-piperidyl)carbamate Using a procedure similar to that described in Example 27 except starting with ethyl chloroformate, the title compound was obtained as a light yellow solid (66%), mp 151°–0.2° C.; MS(CI): 411 (M+H); NMR (300 MHz,DMSO-$d_6$): 1.14(t, 3H, J=7.0 Hz), 1.27–1.44(m, 2H), 1.60–1.94(m, 2H), 2.14–2.31(m, 2H), 2.46(m, 2H), 2.91(m, 2H), 3.20–3.40(m, 3H), 3.95(q, 2H, J=7 Hz), 4.33(s, 1H), 6.88–7.06(m, 4H), 7.14–7.30(m, 4H).

Analysis for $C_{24}H_{27}ClN_2O_2$: Calculated: C, 70.14; H, 6.62; N, 6.82 Found: C, 70.06; H, 6.61; N, 6.71

EXAMPLE 78

2-Pyridylmethyl N-(1-[9,10-dihydro-9,10-methanoanthracen-9-yl-methyl]- 4-piperidyl)carbamate To a stirred solution of Example 8b (866 mg, 2.84 mmol) in tetrahydrofuran (12 mL), was added 1,1'-carbonyldiimidazole (576 mg, 3.55 mmol). After stirring for 18 h, the mixture was added 4-dimethylaminopyridine (347 mg, 2.84 mmol) and 2-pyridylcarbinol (1.37 mL, 14.20 mmol). After refluxing for 48 h, the mixture was treated with water (50 mL) and extracted with methylene chloride (2×75 mL). The combined extracts was washed with water (2×50 mL) and brine (50 mL), dried (sodium sulfate), filtered, and concentrated to give an amber syrup. Chromatography of this material over silica gel (eluant: 99:1 ethyl acetate:acetonitrile) and trituration with hot ether afforded the title compound as a white solid (838 mg, 67%), mp 179.0°– 180.0° C.; MS(CI): 440 (M+H); NMR (300 MHz,DMSO-$d_6$): 1.37(m, 2H), 1.69(m, 2H), 2.25(m, 2H), 2.45(s, 2H), 2.94(m, 2H), 3.34(br s, submerged, 3H), 4.30(s, 1H), 5.05(s, 2H), 6.91(m, 4h), 7.16–7.36(m, 7H), 7.81(d of d, 1H, J=6.8 Hz), 8.52(d, 1H, J=5.0 Hz).

Analysis for $C_{28}H_{29}N_3O_2.0.75H_2O$: Calculated: C, 74.23; H, 6.79; H, 9.27 Found: C, 9.18; H, 6.53; N, 9.18

EXAMPLE 79

2-Pyridylmethyl N-(1-[2-chloro-9,10-dihydro-9,10-methanoanthracen-9-ylmethyl]-4-piperidyl)carbamate Using a procedure similar to that described in Example 78 except starting with Example 7b and 2-pyridylcarbinol, the title compound was obtained as a white solid (67%), mp 133.5°–5.2° C.; MS(CI): 474 (M+H); NMR (300 MHz, DMSO-$d_6$): 1.38(m, 2H), 1.70(m, 2H), 2.24(m, 2H), 2.47(m, 2H), 2.95(m, 2H), 3.28(m, submerged, 3H), 4.33(s, 1H), 5.50(s, 2H), 6.94(m, 3H), 7.10–7.38(m, 7H), 7.81(t, 1H, J=7.9 Hz), 8.53(d, 1H, J=4.1 Hz).

Analysis for $C_{28}H_{28}ClN_3O_2$: Calculated: C, 70.95; H, 5.95; N, 8.87 Found: C, 70.69; H, 5.95; N, 8.65

EXAMPLE 80

Benzyl N-(1-[9,10-dihydro-9,10-methanoanthracen-9-ylmethyl]- 4-piperidyl)carbamate Using a procedure similar to that described in Example 78 except starting with benzyl alcohol, the title compound was obtained as a white solid (13%), mp 137.0°–41.0° C.; MS(CI): 439 (M+H); NMR (300 MHz,DMSO-$d_6$): 1.36(m, 2H), 1.68(m, 2H), 2.24(m, 2h), 2.44(s, 2H), 2.93(m, 2H), 3.33(m, 3H), 4.30(s, 1H), 4.99(s, 2H), 6.91(m, 4H), 7.16–7.34(m, 10H).

Analysis for $C_{29}H_{30}N_2O_2.0.4H_2O$: Calculated: C, 78.14; H, 6.96; N, 6.28 Found: C, 78.39; H, 6.70; N, 6.19

EXAMPLE 81

4Tetrahydropyranyl N-(1-[9,10-dihydro-9,10-methanoanthracen-9-ylmethyl]- 4-piperidyl)carbamate Using a procedure similar to that described in Example 78 except starting with 4-hydroxytetrahydropyran, the title compound was obtained as a white solid (40%), mp 176.5°–9.5° C.; MS(CI): 433 (M+H); NMR (300 MHz, DMSO-$d_6$): 1.21–1.58(m, 4H), 1.65(m, 2H), 1.83(m, 2H), 2.23(m, 2H), 2.44(m, 2H), 2.93(m, 2H), 3.33(m, submerged by H2O, 3H), 3.41(m, 2H), 3.79(m, 2H), 4.30(s, 1H), 4.66(m, 1H), 6.90(m, 4H), 7.07(d, 1H, J=7.8 Hz), 7.15–7.27(m, 4H).

Analysis for $C_{27}H_{32}N_2O_3$: Calculated: C, 74.97; H, 7.46; N, 6.48 Found: C, 74.92; H, 7.54; N, 6.43

EXAMPLE 82

1(2-Chloro-9,10-dihydro-9,10-methanoanthracen-9-ylmethyl)-4-(trans-2,6-dimethyl-4-morpholinyl)piperidine To a solution of 1-(2-chloro-9,10-dihydro-9,10-methanoanthracen- 9-ylmethyl)-4-piperidinone (380 mg, 1.12 mmol) in toluene (10 mL) under nitrogen was added trans 2,6-dimethylmorpholine (155 mg, 1.34 mmol, 1.23 eq). The trans 2,6-dimethylmorpholine isomer was obtained by spinning band distillation of the commercially available mixture of 2,6-dimethylmorpholines. The solution was heated to reflux passing the solvent through 3 A molecular sieves in a modified Dean Stark arrangement. After 2 h, the solvent was removed, replaced with tetrahydrofuran (1.0 mL), and cooled to 0° C. Excess hydrogen chloride gas was bubbled into the solution and then purged with nitrogen. The reaction was warmed to room temperature and a solution of sodium cyanoborohydride (210 mg, 3.35 mmol, 9 eq) in methanol (0.50 mL) was added. A significant amount of gas was evolved. The reaction was stirred for 18 h and quenched with 2.5 N NaOH (10 mL). The aqueous phase was extracted with ethyl acetate (3×10 mL). Combined organic extracts were dried over anhydrous magnesium sulfate, filtered and concentrated to an oil. The reaction product was purified by flash chromatography over silica gel (40 mL, eluent: 30% ethyl acetate in hexane) to yield the title compound as a white solid (371 mg, 76%), mp 237° C. (dec); NMR (CDCl$_3$, 300 MHz) 7.23 (dd, J=5.9, 1.6 Hz, 1H), 7.12 (m, 4H), 6.92 (m, 3H), 4.22 (s, 1H), 3.97 (m, 2H), 3.67 (t, J=6.3 Hz, 1H), 3.58 (t, J=6.2 Hz, 1H), 3.32 (s, 2H), 2.52 (dd, J=11.0, 3.1 Hz, 2H), 2.19 (m, 4H), 1.71 (m, 3H), 1.20 (d, J=6.4 Hz, 6H) MS (CI, CH4) m/z 437 (M+1,100), 439 (34), 465 (M+29,15) The free base was dissolved in diethyl ether and acidified with ethereal HCl. The hydrochloride salt was filtered, rinsed with fresh ether and dried in vacuo (50° C., 13 pascal, 18 h) to yield a white solid, mp 237°–240° C. (dec).

Analysis for C$_{27}$H$_{33}$ClN$_2$0.2HCl.H$_2$O Calculated: C, 61.42; H, 7.06; N, 5.31 Found: C, 61.64; H, 6.99; N, 5.04 The starting piperidinone was made as follows:

a.
1-(2-Chloro-9,10-dihydro-9,10-methanoanthracen-9-ylcarbonyl)-piperidin- 4-ol To a solution of 2-chloro-9,10-dihydro-9,10-methano-9-anthracenecarboxylic acid (described in Example 108) (6.51 g, 24.1 mmol) in toluene (70 mL) was added thionyl chloride (2.28 mL, 31.3 mmol, 1.3 eq). The reaction was heated to reflux monitoring gas evolution with a mineral oil bubbler. The system reached a steady state within 40 min at which time it was slightly cooled and 4-hydroxypiperidine (6.08 g, 60.3 mmol, 2.5 eq) was added portionwise. A significant amount of heat is evolved and the reaction becomes dark. The suspension was heated to reflux for 2 h, cooled to room temperature and stirred for 18 h. The reaction was diluted with ethyl acetate (200 mL) and washed with 3 N HCl (2×100 mL), 2.5 N NaOH (2× 100 mL) and saturated brine (200 mL). The organic phase was dried over anhydrous magnesium sulfate, filtered, and reduced to an oil. The procedure yielded 6.95 g (82%) of the title compound as a viscous oil. No additional purification was required. NOR (d$_6$-DMSO, 250 MHz) 7.63 (m, 1H), 7.21 (m, 6H), 4.41 (s, 1H), 4.18 (m, 1H), 3.65 (m, 2H), 3.25 (m, 2H), 2.76 (m, 2H), 1.90 (m, 2H), 1.38 (m, 2H), MS (CI, CH4) m/z 354 (M+1,100), 356 (36), 382 (M+29,19), 336 (27), 318 (9).

b.
1-(2-Chloro-9,10-dihydro-9,10-methanoanthracen-9-ylmethyl)-piperidin- 4-ol To a cooled suspension (0° C.) of 1-(2-chloro-9,10-dihydro- 9,10-methanoanthracen-9-ylcarbonyl)piperidin-4-ol (described in Example 82a) (6.95 g, 19.6 mmol) in diethyl ether (200 mL) under nitrogen was added lithium aluminum hydride (1.49 g, 39.2 mmol, 8 eq of hydride) in portions. The suspension was stirred at 0° C. for 30 min and warmed to room temperature. After 18 h at room temperature, the excess reagent was carefully quenched with the following in sequence: water (1.5 mL), 2.5 N NaOH (1.5 mL) and additional water (4.5 mL). The suspension was stirred vigorously until the aluminum salts became a granular white solid. The suspension was diluted with ethyl acetate (100 mL), dried with a small amount of anhydrous magnesium sulfate and filtered. The filter cake was rinsed thoroughly with ethyl acetate. The solvent was removed to yield 6.16 g (92%) of the title compound as a white solid. No additional purification was required. TLC analysis (R$_f$0.15, 50% ethyl acetate in hexane). NMR (CDCl$_3$, 300 MHz) 7.20 (m, 4H), 6.95 (m, 3H), 4.60 (s, 1H), 4.24 (s, 1H), 3.70 (m, 1H), 3.34 (s, 2H), 2.88 (m, 2H), 2.58 (s, 2H), 2.37 (m, 2H), 1.57 (m, 2H) MS (CI, CH$_4$) m/z 340 (M+1.98), 342 (33), 322 (100), 368 c(M+29,22), 114 (26)

c.
1-(2-Chloro-9,10-dihydro-9,10-methanoanthracen-9-ylmethyl)- 4-piperidinone To a cooled solution (−78° C.) of oxalyl chloride (3.06 mL, 35.1 mmol, 2 eq) in methylene chloride (100 mL) under nitrogen was added distilled dimethylsulfoxide (5.00 mL, 70.2 mmol, 4 eq). After 10 min 1-(2-chloro-9,10-dihydro-9,10-methanoanthracen-9-ylmethyl) piperidin-4-ol (described in example 82b) (5.96 g, 17.5 mmol) was added as a methylene chloride solution (10 mL). The reaction was stirred at −78° C. for 30 min prior to the addition of triethylamine (19.6 mL, 140 mmol, 8 eq). The cooling bath was removed and the reaction warmed to room temperature over 1.5 h. The reaction was poured into 2.5 N NaOH (100 mL) and the aqueous phase extracted with methylene chloride (3×100 mL). Combined organic extracts were dried over anhydrous magnesium sulfate, filtered, and reduced to an oil. The crude reaction mixture was purified by flash chromatography over silica gel (400 mL, eluent, 20% ethyl acetate in hexane) to yield 5.53 g (93%) of the title compound. TLC analysis (R$_f$0.21, 20% ethyl acetate in hexane). NMR (CDCl$_3$, 250 MHz) 7.26 (m, 1H), 7.13 (m, 3H), 6.95 (m, 3H), 4.28 (s, 1H), 3.49 (s, 2H), 2.94 (t, J=6.1 Hz, 4H), 2.62 (s, 2H), 2.43 (t, J=6.0 Hz, 4H) MS (CI, CH$_4$) m/z 338 (M+1,100), 340 (35), 366 (M+29,31)

EXAMPLE 83

1-(9,10-dihydro-9,10-methanoanthracen-9-ylmethyl)-4-(cis-2,6-dimethyl-4-morpholinyl)piperidine Using a procedure similar to that described in Example 82, except starting with 1-(9,10-dihydro-9,10-methanoanthracen-9-ylmethyl)- 4-piperidinone and employing cis 2,6-dimethylmorpholine, the title compound was formed in 59% yield as a white solid, mp >300° C. (dec). free base: NMR (CDCl$_3$, 250 MHz) 7.22 (m, 2H), 7.14 (m, 2H), 6.92 (m, 4H), 4.24 (s, 1H), 3.63 (m, 2H), 3.36 (s, 2H), 3.05 (br d, J=11.7 Hz, 2H), 2.71 (d, J=10.5 Hz, 2H), 2.56 (d, J=1.2 Hz, 2H), 2.18 (m, 3H), 1.87 (t, J=10.8 Hz, 2H), 1.73 (m, 2H), 1.52 (dt, J=3.6, 11.9 Hz, 2H), 1.14 (d, J=6.3 Hz, 6H) MS (CI, CH4) m/z 403 (M+1,100), 431 (M+29,21), 287 (45) hydrochloride salt:

Analysis for $C_{27}H_{34}N_2O.2HCl.1.3H_2O$ Calculated: C, 65.00; H, 7.80; N, 5.61 Found: C, 64.99; H, 7.51; N, 5.44
The starting piperidinone was prepared as follows:

a. 9,10-Dihydro-9,10-methano-9-anthracenecarboxylic acid

Using a procedure similar to that described in Example 107 except starting with 9,10-dihydro-9,10-methano-9-anthracenecarboxyaldehyde (literature preparation: M. Sunagawa, et al; Chem. Pharm. Bull. Vol. 27 (1979) pp 1806–1812; U.S. Pat. No. 4,224,344 Sunagawa et al., Sumitomo, Ltd.; Sep. 23, 1980; U.S. Pat. No. 4,358,620 Sunagawa et al., Sumitomo, Ltd.; Nov. 9, 1982), the title compound was formed in 80% yield as a white solid. MS (CI, $CH_4$) m/z 237 (M+1,100), 265 (M+29,10), 219 (22), 209 (15), 193 (20).

b. 1-(9,10-Dihydro-9,10-methanoanthracen-9-ylcarbonyl)piperidin-4-ol

Using a procedure similar to that described in Example 82a except starting with 9,10-dihydro-9,10-methano-9-anthracenecarboxylic acid (described in Example 82a), the title compound was formed in quantitative yield as a viscous oil. TLC analysis ($R_f$ 0.54, 10% methanol in chloroform). MS (CI, $CH_4$) m/z 320 (M+1,100), 348 (M+29,22(, 302 (16)

c. 1-(9,10-Dihydro-9,10-methanoanthracen-9-ylmethyl)piperidin-4-ol

Using a procedure similar to that described in Example 82b except starting with 1-(9,10-dihydro-9,10-methanoanthracen-9-ylcarbonyl)piperidin- 4-ol (described in Example 83b), the title compound was formed in 88% yield as a white solid TLC analysis ($R_f$ 0.59, 10% methanol in chloroform). MS (CI, $CH_4$) m/z 306 (M+1,100), 334 (M+29,14), 288 (62), 114(8)

d. 1-(9,10-Dihydro-9,10-methanoathracen-9-ylmethyl)-4-piperidinone

Using a procedure similar to that described in Example 82c except starting with 1-(9,10-dihydro-9,10-methanoanthracen-9-ylmethyl)piperidin- 4-ol (described in Examples 83c), the title compound was formed in 80% yield as a white solid. TLC analysis ($R_f$ 0.31 2% methanol in methylene chloride). MS (CI, $CH_4$) m/z 304 (M+1,100), 332 (M+29, 21)

EXAMPLE 84

1-(9,10-dihydro-9,10-methanoanthracen-9-ylmethyl)-4-(4-morpholinyl)piperidine dihydrochloride To an ice cooled solution of 1-(9,10-dihydro-9,10-methanoanthracen- 9-ylcarbonyl)-4-(4-morpholinyl)piperidine (2.29 g, 5.89 mmol) in tetrahydrofuran (35 mL) was added 1M borane-tetrahydrofuran in tetrahydrofuran (17,7 mL, 17.7 mmol). The reaction was refluxed for 5 h and then was cooled with an ice bath. This mixture was added dropwise a solution of methanolic hydrochloride (25 mL). The ice bath was removed and the solution was refluxed for 0.5 h. The resulting precipitate was filtered with hexane wash (50 mL). The solid was recrystallized from acetonitrile to give the title compound as a white solid (1.62 g, 68%), mp 257.0°–259.0° C.; MS(CI): 375 (M+H); NMR (250 MHz,DMSO-$d_6$): 2.27(m, 6H), 2.75(s, 2H), 3.11(br s, 2H), 3.40(br s, 2H), 3.66(m, 2H), 3.94(m, 4H), 4.38(m, 3H), 4.47(s, 1H), 7.00(m, 4H), 7.34(m, 4H), 10.46(br s, 1H), 11.91(br s, 1H).

Analysis for $C_{25}H_{30}N_2O.2HCl.0.5H_2O$: Calculated: C, 65.78; H, 7.29; N, 6.14 Found: C, 65.56; H, 7.09; N, 6.23
The starting 1-(9,10-dihydro-9,10-methanoanthracen-9-ylcarbonyl)- 4-(4-morpholinyl)piperidine was obtained as follows:

1-(9,10-Dihydro-9,10-methanoanthracen-9-ylcarbonyl)-4-(4-morpholinyl)piperidine A stirred solution of 9,10-dihydro-9,10-methano-9-anthracenecarboxylic acid (1.57 g, 6.7 mmol) and N,N'-carbonyldiimidazole (1.08 g, 6.7 mmol) in tetrahydrofuran (50 mL) was heated at reflux for 1.5 h. The reaction was cooled and a solution of 4-morpholinopiperidine[1] (1.36 g, 8.0 mmol) in tetrahydrofuran was added. The reaction was heated at reflux for 3 h, then stirred overnight at room temperature. The solvent was removed in-vacuo and the resulting brown solid purified by flash chromatography (eluant: 3.97 v/v of methanol in chloroform) to yield the title compound as a tan solid (2.29 g, 89%), mp 179.0°–80.0° C.; MS(CI): 389 (M+H); NMR (300 MHz,DMSO-$d_6$): 1.52 (m, 2H), 2.01 (br m, 3H), 2.41 (br s, 1H), 2.57 (br s, 4H), 2.85 (br s, 4H), 3.74 (m, 4H), 4.00 (m, 1H), 4.91 (br s, 1H), 6.96 (m, 4H), 7.26 (m, 2H), 7.50 (m, 2H).
[1] M. Freifelder and G. R. Stone, *J. Org. Chem.*, 19.61, 26, 3805.

EXAMPLE 85

1-(2-Chloro-9,10-dihydro-9,10-methanoanthracen-9-ylmethyl)-4( 4-morpholinyl)piperidine dihydrochloride Using a procedure similar to that described in Example 82 except starting with morpholine, the title compound was obtained as a white solid (13%), MS(CI): 409 (M+H); NMR (300 MHz,DMSO-$d_6$): 2.06– 2.50(m, 4H), 2.77(s, 2H), 2.97–3.19(m, 2H), 3.20–3.50(m, submerged by $H_2O$, 2H), 3.60–3.78(m, 2H), 3.80–4.11(m, 4H), 4.21–4.54(m, 3H), 4.52(s, 1H), 7.05(m, 3H), 7.38(m, 3H), 7.53(s, 1H), 10.28(br s, 1H).

Analysis for $C_{25}H_{29}ClN_2O.2.0HCl.2.0H_2O$: Calculated: C, 58.00; H, 6.81; N, 5.41 Found: C, 58.53; H, 6.60; N, 5.30

EXAMPLE 86

2-[1-(2-chloro-9,10-dihydro-9,10-methanoanthracen-9-ylmethyl)-4-piperidylamino] pyrimidine 4-amino-1-(2-chloro-9,10-dihydro-9,10-methanoanthracen-9-ylmethyl)piperidine (0.500 g, 1.48 mmol, prepared as described in Example 7b) was heated to 100° C. for 5 hours in 1.5 mL N-methylpyrrolidinone with 2-chloropyrimidine (0.212 g, 1.85 mmol, commercial grade purified by extraction into petroleum ether) and triethylamine (0.300 g, 29.6 mmol) under a nitrogen atmosphere. Aqueous method (3 mL, 50% v/v) was added to the warm (50° C.) reaction mixture to give a white precipitate. The solid was collected by filtration and washed with fresh aqueous methanol (5 mL, 50% v/v) to give the title compound as a white solid. The solid was dissolved in methanolic hydrogen chloride, evaporated to dryness on a rotary evaporator, redissolved in a minimum volume of fresh methanol (2 mL) and added at a slow dropwise rate to rapidly stirring ethyl ether (80 mL) to precipitate the hydrochloride salt as a white solid (0.414 g, 0.99 mmol, 67%), mp 212°–214° C.; MS(CI) 417 (M+H); NMR (250 MHz, DMSO-$d_6$): 10.17(br s, 1H), 8.38–8.33(m, 2H), 7.67(br m, 1H), 7.52–7.49(m, 1H, 7.38–7.31(m, 3H), 7.05–6.96(m, 3H), 6.70–6.63(m, 1H), 4.47(s, 1H), 4.35–4.29(m, 2H), 4.16(br m, 1H), 3.57–3.36(m, 4H), 2.76(m, 2H), 2.12–1.90 (m, 4H).

Analysis for $C_{25}H_{25}ClN_4 \cdot 2.9HCl$: Calculated: C, 57.40; H, 5.38; N, 10.70 Found: C, 57.86; H, 5.27; N, 10.60

EXAMPLE 87

2-[1-(9,10-Dihydro-9,10-methanoanthracen-9-ylmethyl)-4-piperidylamino]pyrimidine 9-Formyl-9,10-dihydro-9,10-methanoanthracene (0.683 g, 3.1 mmol) was stirred for 1 hour at room temperature in methanol (7.0 mL) with 2-(4-piperidylamino)pyridimine hydrochloride (1.000 g, 4.7 mmol, prepared as described below) and activated, powdered, 3 angstrom molecular sieves (0.820 g). The pH was initially adjusted to 6.5 with methanolic hydrogen chloride. Sodium cyanoborohydride (0.137 g, 2.2 mmol) was added and the tan suspension stirred for 23 hours. The suspension was poured into strongly basic (NaOH) brine solution (pH>11) and extracted with methylene chloride. The combined extracts were dried (sodium sulfate) and concentrated to give the crude product. Flash chromatography on silica gel using 15% acetone/hexanes provided the title compound as a white solid (0.225 g, 0.6 mmol, 20%). Using a procedure similar to that described in Example 87, the hydrochloride salt was obtained, mp 290° C. (dec); MS(CI): 456 (M+H); NMR (250MHz, DMSO-$d_6$): 9.87(br m, 1H), 8.38–8.32(m, 2H), 7.64(br m, 1H), 7.37–7.31(m, 4H), 7.03–6.94(m, 4H), 6.70–6.63(m, 1H), 4.46(s, 1H), 4.34–4.32(m, 2H), 4.16(br m, 1H), 3.60–3.34(m, 4H), 2.73(s, 2H), 2.11–1.88(m, 4H).

Analysis for $C_{25}H_{26}N_4 \cdot 2HCl \cdot 1.3H_2O$: Calculated: C, 62.71; H, 6.44; N, 11.70 Found: C, 62.34; H, 6.22; N, 11.47 The starting 2-(4-piperidylamino)pyrimidine was obtained as follows:

a. 2-[4-(1-Benzylpiperidyl)amino]pyrimidine

4-Amino-1-benzylpiperidine (41.5 g, 218.0 mmol) was refluxed for 72 hours in 170 mL 1-butanol with 2-chloropyrimidine (10.0 g, 87 mmol), sodium bicarbonate (14.7 g, 175 mmol) and potassium iodide (14.5 g, 87 mmol). The butanol was removed under reduced pressure and the residue was coated onto silica gel with methylene chloride. Flash chromatography on silica gel using 5% methanol/methylene chloride afforded the title compound as a white solid (18.3 g, 68 mmol, 78%), MS(CI): 269 (M+H), NMR (300 MHz, DMSO-$d_6$): 8.25–8.23(d, J=4.5Hz, 2H), 7.35–7.22(m, 5H), 7.04–7.01(m, 1H), 6.53–6.50(t, J=4.8Hz, 1H), 3.70(br m, 1H), 3.45(s, 2H), 2.81–2.77(m, 2H), 2.04–1.97(m, 2H), 1.83–1.80(m, 2H), 1.55–1.47(m, 2H).

2-[4-(1-Benzylpiperidyl)amino]pyrimidine (4.030 g, 15.0 mmol, prepared as described in Example 87a) was refluxed for 1 hour with 1-chloroethylchloroformate (2.140 g, 15 mmol) in 40 mL 1,2-dichloroethane. The solution was concentrated under reduced pressure and the resulting residue was refluxed in 40 mL methanol for 1 hour. The cooled methanol solution was added dropwise to rapidly stirring ethyl ether to produce a while precipitate. The while solid was collected to give a quantitative recovery of material which was 80% debenzylated. This hydrochloride salt mixture was used without further purification, MS(CI): 179(M+H).

EXAMPLE 88

4-Amino-2-[1-(9,10-dihydro-9,10-methanoanthracen-9-ylmethyl)-4-piperidylamino]-5-fluoropyrimidine Using a procedure similar to that described in Example 86 except starting with 4-amino-1-(9,10-dihydro-9,10-methanoanthracen-9-ylmethyl)piperidine (prepared as described in Example 8b) and 4-amino- 2-chloro-5-fluoropyrimidine, the hydrochloride salt of the title compound was obtained as a white solid (8%), mp 250°–254° C.; MS(CI): 416 (M+H); NMR (300 MHz, DMSO-$d_6$): 10.25(br s, 1H), 8.60(br m, 1H), 8.10(m, 1H), 7.39–7.32(m, 4H), 7.03–6.95(m, 4H), 4.46(s, 1H), 4.36(s, 2H), 4.18–3.80(br m, 1H), 3.60–3.38(m, 4H), 2.75(s, 2H), 2.14–1.96(m, 4H).

Analysis for $C_{25}H_{26}FN_5 \cdot 2.9HCl$: Calculated: C, 57.60; H, 5.59; N, 13.40 Found: C, 57.73; H, 5.84; N, 13.33

EXAMPLE 89

2-[1-(9,10-Dihydro-9,10-methanoanthracen-9-ylmethyl)-4-piperidyl amino]-5-iodopyrimidine Using a procedure similar to that described in Example 86 except starting with 4-amino-1-(9,10-dihydro-9,10-methanoanthracen-9-ylmethyl)piperidine (prepared as described in Example 8b) and 2-chloro- 5-iodopyrimidine, the title compound was obtained as a white solid (100%), mp 240° C. (dec); MS(CI): 509 (M+H); NMR (300MHz, DMSO-$d_6$): 9.95(br s, 1H), 8.50–8.45(m, 2H), 7.68(b, 1H), 7.37–7.32(m, 4H), 7.03–6.95(m, 4H), 4.45(s, 1H), 4.35–4.31(m, 2H), 4.18–3.80(br m, 1H), 3.58–3.38(m, 4H), 2.73(s, 2H), 2.08–1.87(m, 4H).

Analysis for $C_{25}H_{25}IN_4 \cdot 2HCl$: Calculated: C, 51.70; H, 4.68; N, 9.64 Found: C, 51.55; H, 4.56; N, 9.48

EXAMPLE 90

2-[1-(2-Chloro-9,10-dihydro-9,10-methanoanthracen-9-ylmethyl)-4-piperidylamino]-5-phenylpyrimidine Using a procedure similar to that described in Example 86 except starting with 2-chloro-5-phenylpyrimidine the hydrochloride salt of the title compound was obtained as a white solid (87%), mp 290°–292° C.; MS(CI): 493 (M+H); NMR (300MHz, DMSO-$d_6$): 10.15(br s, 1H), 8.73–8.69(m, 2H), 7.70(br m, 1H), 7.67–7.63(m, 2H), 7.53–7.33(m, 7H), 7.05–7.01(m, 3H), 4.49(s, 1H), 4.37–4.31(m, 2H), 4.25–4.00(br m, 1H), 3.60–3.42(m, 4H), 2.77(m, 2H), 2.15–1.95(m, 4H).

Analysis for $C_{31}H_{29}ClN_4 \cdot 2HCl \cdot 0.6H_2O$: Calculated: C, 64.60; H, 5.63; N, 9.71 Found: C, 64.59; H, 5.58; N, 9.68

EXAMPLE 91

4-Amino-2-[1-(2-chloro-9,10-dihydro-9,10-methanoanthracen-9-ylmethyl)-4-piperidylamino]-5-fluoropyrimidine Using a procedure similar to that described in Example 68 except starting with 4-amino-2-chloro-5-fluoropyrimidine the hydrochloride salt of the title compound was obtained as a white solid (18%), mp 260° C. (dec: MS(CI): 450 (M+H); NMR (300MHz, DMSO-$d_6$): 10.15(br s, 1H), 8.60(br m, 1H), 8.09(m, 1H), 7.51(s, 1H), 7.35–7.33(m, 3H), 7.05–

7.01(m, 3H), 4.49(s, 1H), 4.40–4.30(m, 2H), 4.18–3.80(br m, 1H), 3.60–3.37(m, 4H), 2.77(s, 2H), 2.15–1.95(m, 4H).

EXAMPLE 92

2-[1-(9,10-Dihydro-9,10-methanoanthracen-9-ylmethyl)-4-piperidylamino]- 5-phenylpyrimidine Using a procedure similar to that described in Example 86 except starting with 4-amino-1-(9,10-dihydro-9,10-methanoanthracene-9-ylmethyl)piperidine (prepared as described in Example 8b) and 2-chloro- 5-phenylpyrimidine the hydrochloride salt of the title compound was obtained as a white solid (60%), mp 292°–294° C.; MS(CI): 459 (M+H); NMR (300MHz, DMSO-$d_6$): 9.95(br s, 1H), 8.70–8.66(m, 2H), 7.66–7.62(m, 3H), 7.47–7.33(m, 7H), 7.04–6.96(m, 4H), 4.46(s, 1H), 4.35–4.33(m, 2H), 4.25–4.00(br m, 1H), 3.0–3.35(m, 4H), 2.74(s, 2H), 2.15–1.91(m, 4H).

Analysis for $C_{31}H_{30}N_4 \cdot 1.5HCl$: Calculated: C, 72.50; H, 6.19; N, 10.90 Found: C, 72.77; H, 6.27; N, 10.49

EXAMPLE 93

2-[1-(2-chloro-9,10-dihydro-9,10-methanoanthracen-9-ylmethyl)- 4-piperidylamino]-5-iodopyrimidine Using a procedure similar to that described in Example 86 except starting with 2-chloro-5-iodopyrimidine the hydrochloride salt of the title compound was obtained as a white solid (100%), mp 208° C. (dec); MS(CI): 543 (M+H); NMR (300MHz, DMSO-$d_6$): 9.79(br s, 1H), 8.50– 8.45(m, 2H), 7.70–7.68(m, 1H), 7.50–7.48(m, 1H), 7.35–7.33(m, 3H), 7.05–7.02(m, 3H), 4.49(s, 1H), 4.35–4.29(m, 2H), 4.15–3.85(br m, 1H), 3.60–3.40(m, 4H), 2.74(m, 2H), 2.10–1.83(m, 4H).

Analysis for $C_{25}H_{24}ClIN_4 \cdot 1.3HCl$: Calculated: C, 50.90; H, 4.23; N, 9.49 Found: C, 50.70; H, 4.35; N, 9.37

EXAMPLE 94

2-[1-(2-Chloro-9,10-dihydro-9,10-methanoanthracen-9-ylmethyl)- 4-piperidylamino]pyrimidin-4-ol 2-[1-(2-Chloro-9,10-dihydro-9,10-methanoanthracene-9-ylmethyl)- 4-piperidylamino]-4-methoxypyrimidine (0.400 g, 0.9 mmol, prepared as described in Example 95) was treated with methanolic hydrogen chloride to give the hydrochloride salt (as described in Example 86). This white solid was dried at 100° C. for 20 hours under high vacuum (20 mTorr) which produced a small amount (20%) of the title compound. This mixture of 4-methoxy and 4-hydroxy pyrimidines was dissolved in aqueous base (NaOH)/brine and extracted with methylene chloride. The combined extracts were dried (sodium sulfate) and concentrated on a rotary evaporator to give the mixture of free bases. Flash chromatography on silica using 2.5% methanol/methylene chloride gave the title compound as a white solid (0.090 g, 0.2 mmol, 23%). Using a procedure similar to that described in example 86, the hydrochloride salt of title compound was obtained as a white solid, mp 210°–212° C.; MS(CI): 433 (M+H); NMR (300MHz, DMSO-$d_6$): 9.98(br s, 1H), 7.66–7.63(d, J=6.8Hz, 1H), 7.49(s, 1H), 7.35–7.32(m, 3H), 7.04–7.00(m, 3H), 5.71–5.69(br m, 1H), 4.48(s, 1H), 4.40–4.32(m, 2H), 4.15–3.85(br m, 1H), 3.60–3.35(m, 4H), 2.74(m, 2H), 2.10–1.88(m, 4H).

Analysis for $C_{25}H_{25}ClN_4O \cdot 1.7HCl$. Calculated: C, 60.70; H, 5.44; N, 11.30 Found: C, 60.67; H, 5.52; N, 11.23

EXAMPLE 95

2-[2-Chloro-9,10-dihydro-9,10-methanoanthracen-9-ylmethyl)- 4-piperidylamino]-4-methoxypyrimidine Using a procedure similar to that described in Example 86 except starting with 2-chloro-4-methoxypyrimidine, the title compound was obtained as a white solid (75%), mp 140°–141° C.; MS(CI): 447 (M+H); NMR (300MHz, DMSO-$d_6$): 7.99–7.98(d, J=5.4Hz, 1H) 7.29–7.20 (m, 4H), 6.99–6.91(m, 4H), 5.99–5.97(d, J=5.4Hz, 1H), 4.34(s, 1H), 3.79(s, 3H), 3.75(br m, 1H), 3.36–3.32(m, 4H), 2.97(br m, 2H), 2.29–2.26(m, 2H), 1.79(br m, 2H), 1.46(br m, 2H).

Analysis for $C_{26}H_{27}ClN_4O \cdot 0.25H_2O$: Calculated: C, 69.20; H, 6.14; N, 12.40 Found: C, 69.16; H, 6.00; N, 12.43

EXAMPLE 96

2-[1-(2-Chloro-9,10-dihydro-9,10-methanoanthracen-9-ylmethyl)- 4-piperidylamino]-5-fluoropyrimidine Using a procedure similar to that described in Example 86 except starting with 2-chloro-5-fluoropyrimidine, the hydrochloride salt of the title compound was obtained as a white solid (95%), mp 200° C. (dec); MS(CI): 435 (M+H); NMR (250MHz, DMSO-$d_6$): 9.88(br s, 1H), 8.44–8.39(m, 2H), 7.52–7.50(m, 2H), 7.36–7.33(m, 3H), 7.05–6.97(m, 3H), 4.49(s, 1H), 4.35–4.30(m, 2H), 4.15–3.85(br m, 1H), 3.60–3.33(m, 4H), 2.75(s, 2H), 2.11–1.84(m, 4H).

Analysis for $C_{25}H_{24}ClFN_4 \cdot 0.75HCl \cdot 0.75H_2O$: Calculated: C, 63.10; H, 5.56; N, 11.80 Found: C, 63.10; H, 5.40; N, 11.32

EXAMPLE 97

2-[1-(9,10-dihydro-9,10-methanoanthracen-9-ylmethyl)-4-piperidyl amino]-4-amino-5-nitropyrimidine Using a procedure similar to that described in Example 86 except starting with Example 8b and 2-chloro-4-amino-5-nitropyrimidine (General Intermediates of Canada), the hydrochloride salt of the title compound was obtained as a white solid (100%), mp 240° C. (dec); MS(CI): 443 (M+H; NMR (250MHz, DMSO-$d_6$): 9.80(br s, 1H), 8.92–8.85(m, 1H), 8.38–7.91(m, 3H), 7.38–7.30(br m, 4H), 7.00–6.94(br m, 4H), 4.45(s, 1H), 4.36–4.32(br m, 2H), 4.20–3.80(br m, 1H), 3.60–3.25(m, 4H), 2.71(s, 2H), 2.16–1.88(m, 4H).

Analysis for $C_{25}H_{26}N_6O_2 \cdot 1.4HCl$: Calculated: C, 60.89; H, 5.60; N, 17.00 Found: C, 60.99; H, 5.60; N, 16.98

EXAMPLE 98

2-[1-(9,10-Dihydro-9,10-methanoanthracen-9-ylmethyl)-4-piperidyl amino]-4,5-diaminopyrimidine 2-[1-(9,10-Dihydro-9,10-methanoanthracen-9-ylmethyl)-4-piperidyl amino]-4-amino-5-nitropyrimidine (1.000 g, 2.3 mmol, prepared as described in Example 97), 0.2 weight equivalents of 10% Pd/C, and ammonium formate (1.000 g, 15.9 mmol) were combined in 20 mL 50% ethyl acetate/methanol and stirred under a nitrogen atmosphere at room temperature for 28 hours. The reaction mixture was filtered through celite and concentrated on a rotary evaporator to give the title compound as a tan glassy solid (0.643 g, 1.6 mmol, 69%), mp 138°–140°C.; MS(CI): 413 (M+H); NMR (250MHz, DMSO-$d_6$): 7.29–7.18(m, 5H), 6.98– 6.87(m, 4H), 6.33(s, 2H), 5.75–5.72(br m, 1H), 4.32(s, 1H), 3.56(br m, 1H), 3.36(br, m, 2H), 2.99–2.94(d, J=11.3Hz, 2H), 2.47(s, 2H), 2.32– 2.23(m, 2H), 1.80–1.75(m, 2H), 1.41–1.37(m, 2H).

Analysis for $C_{25}H_{28}N_6 \cdot H_2O$: Calculated: C, 69.70; H, 7.02; N, 19.52 Found: C, 69.73; H, 6.70; N, 19.33

EXAMPLE 99

2-[1-(9,10-Dihydro-9,10-methanoanthracen-9-ylmethyl)-4-piperidylamino]purine

2-[1-(9,10-Dihydro-9,10-methanoanthracen-9-ylmethyl)-4-piperidyl amino]-4,5-diaminopyrimidine (0.420 g, 1.0 mmol, prepared as described in Example 98) was dissolved in 2 mL formic acid. The yellow solution was heated for 15 minutes at 100° C. and for 3 hours at 210° C. The solution was cooled and concentrated to dryness several times from methanol on a rotary evaporator to give the formate salt of the title compound as a tan foamy solid (0.400 g, 0.9 mmol, 93%), mp 118°–120° C.; MS(CI): 423 (M+H) NMR (250MHz, DMSO-$d_6$): 9.08–7.62(m, 4H), 7.29– 7.20(m, 4H), 6.98–6.88(m, 4H), 6.40–6.32(br m, 2H), 4.33(s, 1H), 3.69(br m, 1H), 3.47–3.43(m, 2H), 3.07–3.02(m, 2H), 2.50(s, 2H), 2.44– 2.38(m, 2H), 1.82–1.77(m, 2H), 1.54–1.46(m, 2H).

Analysis for $C_{26}H_{26}N_6 \cdot 3HCO_2H \cdot H_2O$: Calculated: C, 60.20; H, 5.92; N, 14.50 Found: C, 59.43; H, 5.71; H,m 14.81

EXAMPLE 100

2-[1-(9,10-Dihydro-9,10-methanoanthracen-9-ylmethyl)-4-piperidyl amino]-4,6-dimethylpyrimidine Using a procedure similar to that described in Example 86 except starting with 4-amino-1-(9,10-dihydro-9,10-methanoanthracen-9-ylmethyl)piperidine (prepared as described in Example 8b) and 2-chloro- 4,6-dimethylpyrimidine the hydrochloride salt of the title compound was obtained as a white solid (55%), mp 205°–207° C.; MS(CI): 411 (M+H); NMR (250 MHz, DMSO-$d_6$): 10.07(br s, 1H), 8.40(br m, 1H), 7.38–7.31(m, 4H), 7.03–6.94(m, 4H), 6.72(s, 1H), 4.46(s, 1H), 4.35–4.33(m, 2H), 4.21–3.97(br m, 1H), 3.60–3.48(m, 4H), 2.74(s, 2H), 2.37(s, 6H), 2.13– 1.94(m, 4H).

Analysis for $C_{27}H_{30}N_4 \cdot 3HCl \cdot 0.5H_2O$ Calculated: C, 61.50; H, 6.46; N, 10.60 Found: C, 61.91; H, 6.57; N, 10.50

EXAMPLE 101 AND EXAMPLE 102

2-[1-(9,10-Dihydro-9,10-methanoanthracen-9-ylmethyl)-4-piperidyl amino]-4,6-dichloropyrimidine and 6-[1-(9,10-dihydro-9,10-methanonthracen-9-ylmethyl)-4-piperidylamino]-2,4-dichloropyrimidine.

Using a procedure similar to that described in Example 86 except starting with 4-amino-1-(9,10-dihydro-9,10-methanoanthracen-9-ylmethyl)piperidine (prepared as described in Example 8b) and 2,4,6-trichloropyrimidine, the free bases of the two title compounds were purified by chromatography using 1:10 v/v ethyl acetate:hexane as eluting solvent. Treatment with hydrochloric acid as described in Example 86 provided the title compounds.

2-[1-(9,10-Dihydro-9,10-methanoanthracen-9-ylmethyl)-4-piperidylamino]- 4,6-dichloropyrimidine was obtained as a while solid (29%), mp 167°–168° C.; TLC Rf: 0.3(1:10 v/v ethyl acetate:hexane); MS(CI): 451 (M+H); NMR (250MHz, DMSO-$d_6$): 8.13–8.09(m, 4H), 6.98–6.87(m, 4H), 6.84(s, 1H), 4.31(s, 1H), 3.65(br m, 1H), 3.36– 3.30(m, 2H), 3.01–2.96(m, 2H), 2.46(s, 2H), 2.34–2.25(m, 2H), 1.80– 1.75(m, 2H), 1.52–1.44(m, 2H).

Analysis for $C_{25}H_{24}Cl_2N_4$: Calculated: C, 66.50; H, 5.36; N, 12.40 Found: C, 66.69; H, 5.52; N, 12.27

6-[1-(9,10-Dihydro-9,10-methanoanthracen-9-ylmethyl)-4-piperidylamino]- 2,4-dichloropyrimidine was obtained as a white solid (43%), mp 108°–110° C.; TLC Rf: 0.5(1:10 v/v ethyl acetate:hexane); MS(CI): 451 (M+H); NMR (250MHz, DMSO-$d_6$): 8.30–8.12(m, 1H), 7.20–7.19(m, 4H), 6.97–6.88(m, 4H), 6.48(s, 1H), 4.32(s, 1H), 3.79(br m, 1H), 3.38– 3.31(m, 2H), 2.99–2.95(m, 2H), 2.47(s, 2H), 2.40–2.35(m, 2H), 1.85– 1.80(br m, 2H), 1.44–1.40(r m, 2H).

Analysis for $C_{25}H_{24}Cl_4N_4$: Calculated: C, 66.50; H, 5.36; N, 12.40 Found: C, 66.49; H, 5.46; N, 12.16

EXAMPLE 103

1-(9,10-Dihydro-9,10-methanoanthracen-9-ylmethyl)-4-(2-pyridylamino) piperidine 4-amino-1-(9,10-dihydro-9,10-methanoanthracen-9-ylmethyl)-piperidine (0.305 g, 1.0 mmol, prepared as described in Example 8b), 2-fluoropyridine (0.117 g, 1.2 mmol), and anhydrous potassium fluoride (0.174 g, 3.0 mmol) were heated to 150° C. in 3 mL N-methylpyrrolidinone for 52 hours. The warm reaction mixture was added slowly to a rapidly stirring mixture of aqueous NaOH/ice/methanol to give a tan precipitate. The solid was collected and washed with water. The solid was dissolved in methanolic hydrogen chloride and concentrated to dryness several times from methanol to give the hydrochloride salt of the title compound as a white solid (0.239 g, 0.5 mmol, 50%), mp 270° C. (decomp); MS(CI): 382 (M+H); NMR (300MHz, DMSO-$d_6$): 10.27(br s, 1H), 7.95–7.85(m, 2H), 7.39–7.33(m, 5H), 7.04–6.96(m, 5H), 6.85(br m, 1H), 4.47(s, 1H), 4.41(s, 2H), 4.20–4.00(br m, 1H), 3.66–3.30(m, 4H), 2.76(s, 2H), 2.20–2.04(m, 4H).

Analysis for $C_{26}H_{27}N_3 \cdot 2.8HCl$: Calculated: C, 64.60; H, 6.21; N, 8.69 Found: C, 64.61; H, 6.46; N, 8.60

EXAMPLE 104

1-(2-Chloro-9,10-dihydro-9,10-methanoanthracen-9-ylmethyl)-4-( 2-pyridylamino)piperidine Using a procedure similar to that described in Example 103 except starting with 4-amino-1-(2-chloro-9,10-dihydro-9,10-methanoanthracen- 9-ylmethyl)piperidine (prepared as described in Example 7b) the title compound was obtained as a white solid (73%), mp 152°–155° C.; MS(CI): 416 (M+H); NMR (300MHz, DMSO-$d_6$): 7.94–.792(m, 1H), 7.34–7.21(m, 4H), 6.99–6.91(m, 3H), 6.43–6.40(m, 2H), 6.32–6.30(d, J=7.8Hz, 1H), 4.34(s, 1H), 3.71–3.68(br m, 1H), 3.42–3.34(m, 2H), 2.98–2.95(m, 2H), 2.50(m, 2H), 2.34–2.27(m, 2H), 1.87–1.83(br m, 2H), 1.41–1.37(br m, 2H).

Analysis for $C_{26}H_{26}ClN_3 \cdot H_2O$: Calculated: C, 71.95; H, 6.50; N, 9.68 Found: C, 71.96; H, 6.06; N, 9.55

EXAMPLE 105

2-[1-(9S,10S-2-Chloro-9,10-dihydro-9,10-methanoanthracen-9-ylmethyl)-4-piperidylamino]pyrimidine Using a procedure similar to that described in Example 86 except starting with 4-amino-1-(9S,10S-2-chloro-9,10-dihydro-9,10-methanoanthracen- 9-ylmethyl)piperidine (prepared as described in Example 1e) the title compound was obtained as a white solid (46%), mp 278°–281° C.; MS(CI): 417 (M+H); NMR (300MHz, DMSO-d$_6$): 10.19(br s, 1H), 8.38– 8.33(m, 2H), 7.70–7.64(br m, 1H), 7.53–7.50(m, 1H), 7.38–7.32(m, 3H), 7.60–6.98(m, 3H), 6.70–6.64(m, 1H), 4.48(s, 1H), 4.40–4.25(m, 2H), 4.15(br m, 1H), 3.57–3.33(m, 4H), 2.80–2.74(m, 2H), 2.17–1.89(m, 4H).

Analysis for C$_{25}$H$_{25}$ClN$_4$.1.6HCl: Calculated: C, 63.20; H, 5.64; N, 11.80 Found: C, 63.08; H, 5.72; N, 11.55

EXAMPLE 106

2-[1-((9R,10R)-2-Chloro-9,10-dihydro-9,10-methanoanthracen-9-ylmethyl-4-piperidylamino]pyrimidine Using a procedure similar to that described in Example 86 except starting with 4-amino-1-[(9R,10R)-2-chloro-9,10-dihydro-9,10-methanoanthracen- 9-ylmethyl)piperidine the title compound was obtained as a white solid (77%), mp 260°–263° C.; MS(CI): 417 (M+H); NMR (300MHz, DMSO-d$_6$): 10.19(br s, 1H), 8.40–8.35(m, 2H), 7.78(br m, 1H) 7.53– 7.51(m, 1H), 7.39–7.33(m, 3H), 7.05–6.98(m, 3H), 6.72–6.66(m, 1H), 4.48(s, 1H), 4.36–4.30(m, 2H), 4.16( br m, 1H), 3.58–3.39(m, 4H), 2.77(m, 2H), 2.17–1.92(m, 4H).

Analysis for C$_{25}$H$_{25}$ClN$_4$.1.9HCl: Calculated: C, 61.80; H, 5.58; N, 11.50 Found: C, 62.09; H, 5.77; N, 11.05
The starting material 4-amino-1-[(9R,10R)-2-chloro-9,10-dihydro- 9,10-methanoanthracen-9-ylmethyl)piperidine was obtained as follows:

a. 1-[(9R,10R)-2-Chloro-9,10-dihydro-9,10-methanoanthracen-9-ylcarbonyl]-4-(t-butyoxycarbonylamino)piperidine Using a procedure similar to that described in Example 1a, except starting with 1-(9R,10R)-2-chloro-9-carboxy-9,10-dihydro-9,10-methanoanthracene (prepared as described in Example 109b), 1-(9R,10R)-2-chloro- 9-chlorocarbonyl-9,10-dihydro-9,10-methanoanthracene was obtained as a yellow solid. Using a procedure similar to that described in Example 1b except starting with 1-(9R,10R)-2-chloro-9-chlorocarbonyl- 9,10-dihydro-9,10-dihydro-9,10-methanoanthracene, (prepared as described above) the title compound was obtained as a colorless glass (93%), MS(CI): 453 (M+H); NMR (300MHz, DMSO-d$_6$): 7.66(br m, 1H), 7.36–7.30(m, 3H), 7.02–6.91(m, 4H), 4.48(br m, 1H), 4.43(s, 1H), 3.56–3.62 (m, 2H), 3.35–3.28(m, 2H), 3.02–2.73(m, 4H), 1.82–1.74(m, 2H), 1.37(m, 11H).

b. 4-Amino-1-[(9R,10R)-2-chloro-9,10-methanoanthracen-9-ylcarbonyl]piperidine Using a procedure similar to that described in Example 1c, except starting with 1-[(9R,10R)-2-chloro-9,10-methanoanthracen- 9-ylcarbonyl]-4-(-butoxycarbonylamino)piperidine (prepared as described in example 106a), the title compound was obtained as a white foamy glass (98%), MS(CI): 353 (M+H); NMR (300MHz, DMSO-d$_6$): 7.70–7.31(m, 4H), 7.02–6.99(m, 3H), 4.47(br m, 1H), 4.42(s, 1H), 3.75–3.55(br m, 1H), 3.50–3.25(br m, 2H), 3.03–2.74(m, 5H), 1.80–1.70(br m, 2H), 1.40–1.11(br m, 2H).

c. 4-Amino-1[(9R,10R)-2-chloro-9,10-dihydro-9,10-methanoanthracen- 9-ylmethyl]piperidine Using a procedure similar to that described in Example 1d, except starting with 4-amino-1-[(9R,10R)-2-chloro-9,10-dihydro-9,10-methanoanthracen- 9-ylcarbonyl]piperidine (prepared as described in example 106b), the title compound was obtained as a colorless syrup (83%); MS(CI): 339 (M+H); NMR (300MHz, DMSO-d$_6$): 7.29–7.18(m, 4H), 6.98– 6.90(m, 3H), 4.33(s, 1H), 3.36–3.25(m, 2H), 2.91–2.87(m, 2H), 2.51– 2.43(m, 2H), 2.24–2.13(m, 2H), 1.64–1.61(m, 2H), 1.25–1.13(m, 2H).

EXAMPLE 107

This example illustrates the synthesis of an intermediate aldehyde designated as compound 22 i Scheme I, 2-Chloro-9-formyl-9,10-dihydro- 9,10-methanoanthracene a. 2-Chloroanthracene

A stirred suspension of 2-chloroanthraquinone (1260 g, 5.19 mol) in concentrated ammonium hydroxide (7.5 L) and water (2.5 L) was warmed to 40° C. Zinc dust (845 g, 12.93 mol) was added in one portion, changing the color to deep red. The mixture was stirred for 45 min at 50° C., then cautiously treated with a second portion of zinc dust (845 g). After the addition, the stirred mixture was heated gradually over 3 h to 90° C., then maintained at 90°–95° C. for 2 h (red color dissipated). TLC analysis (silica gel; hexane;methylene chloride (3:1) showed complete conversion of the anthraquinone (R$_f$ 0.35) to the desired anthracene (R$_f$ 0.80). The reaction mixture was stirred overnight as it cooled to room temperature. The cooled mixture was treated with methylene chloride (4 L), stirred for 2 h, then filtered through Celite to remove the excess zinc. The filter cake was washed with methylene chloride (6×1 L). The methylene chloride layer was separated from the aqueous, then treated with 6 N hydrochloric acid (3 L) and stirred for 2 h. A first crop of 2-chloroanthracene was collected by filtration and washed with water (4× 1 L). Vacuum drying afforded a light yellow crystalline product weighting 804.6 g (mp 220°–221° C.). The methylene chloride portion of the filtrate was concentrated in vacuo to 10% of its original volume. This produced an additional 158.5 g of the desired compound for a total yield of 963.1 g (87.2%). NMR (CDCl$_3$) 8.39 (s, 1H), 8.30 (s, 1H), 7.96 (s, 4H), 7.49 (s, 2H), 7.36 (d, J=8.7 Hz, 1H).

b. 2-Chloro-9-formylanthracene

N-methylformanilide (2.45 kg, 18.12 mol) was treated with phosphorus oxychloride (2.66 kg, 17.35 mol) over a 40 min period at ambient temperature. The intermediate Vilsmeier complex was stirred for 2 h at room temperature, then treated with 2-chloroanthracene (described in Example 1a) (963 g, 4.53 mol), and o-dichlorobenzene (1.0 L). The resulting bright yellow mixture was heated gradually over 1.5 h to 9° C. at which point an exotherm ensued raising the reaction temperature to 115° C. The heat was removed until the exotherm subsided (45 min)., after which time the mixture was heated for 9 h at 90° C., then cooled. TLC analysis (silica gel; ethyl acetate:hexane 1:4) showed a small amount of unreacted anthracene (R$_f$ 0.90), a small amount of the 3-chloro isomer ($R_f$ 0.65), and the 2-chloro isomer ($R_f$ 0.58) as the major component. The cooled reaction mixture was poured into ice/water (27 L) precipitating a dark brown tar. The aqueous layer was decanted away from the tar and extracted with methylene chloride (5×2 L). The combined extracts were used to redissolve the tar. The methylene chloride solution was washed with 3 N hydrochloric acid (4×1.5 L), followed by water (2 L), then dried over magnesium sulfate. The extracts were filtered, then pressure-filtered through a bed of silica gel, eluting with methylene chloride until all of the desired compound had been recovered. The eluent was concentrated on the rotary evaporator to give a slurry of bright yellow crystals (in o-dichlorobenzene). The crystals were collected by filtration, washed with diethyl ether (2×500 ml), then vacuum dried to afford 619.7 g (56.9%) of the desired 2-chloro-9-formylanthracene (mp 148°150° C.). NMR (CDCl$_3$) 11.35 (s, 1H), 9.02 (d, J=0.9 Hz, 1H), 8.81 (d, J=8.9 Hz, 1H), 8.56 (s, 1H), 7.98 (m, 1H), 7.90 (d, J=8.9 Hz, 1H), 7.66 (m, 1H), 7.53 (m, 1H), 7.42 (m, 1H)

c. 12-Acetoxy-2-chloro-9-formyl-9,10-dihydro-9,10-ethanoanthracene (E and Z isomers)

A mixture of 2-chloro-9-formylanthracene (described in Example 1b) (100.0 g, 0.415 mol) and vinyl acetate (400 ml 374 g, 4.34 mol) was placed in a stainless steel bomb (PARR) and heated at 200° C. (sand bath temp.) for 24 h, then cooled. The reaction mixture was concentrated on the rotary evaporator to remove the excess vinyl acetate, leaving the crude product as a tan crystalline solid. The crude product from several batches, which consumed 670.0 g (2.78 mol) of the 2-chloro-9-formylanthracene, was pooled. Trituration with diethyl ether (1.0 L) gave an off-white crystalline solid which was collected by filtration, washed with diethyl ether (2×300 ml), then vacuum dried to afford 629.0 g (69.1%) of the title compound (mp 145°–153° C.). NMR (CDCl$_3$) 10.58 (s) and 10.64 (s, 1H), 7.63 (m) and 7.76 (d, J=1.5 Hz, 1H), 7.15–7.36 (m, 6H), 5.46 (m, 1H), 4.29 (s, 1H) 2.55 (m, 1H), 1.88 (s) and 1.91 (s, 1H), 1.55 (m, 1H)

Evaporation of the filtrates and washes gave a thick brown oil, which was purified by column chromatography over silica gel eluting with a solvent mixture of methylene chloride:hexane (1:1). The recovered solid was recrystallized from diethyl ether:hexane (1:1; 400 mL) to afford an additional 175.5 g (19.3%) of the desired compound.

d. 12-Acetoxy-2-chloro-9,10-dihydro-9,10-ethano-9-anthracenecarboxylic acid (E and Z isomers)

A stirred solution of 12-acetoxy-2-chloro-9-formyl-9,10-dihydro- 9,10-ethanoanthracene (described in Example 1c) (629.0 g. 1.925 mol) dissolved in acetone (8.0 L) was treated with Jones Reagent (1.50 L. approx. 1.93 mol, prepared as described in Fieser & Fieser Vol. 1: pp 142) over a period of 1 h at 10°–20° C. After the addition of the Jones Reagent, the reaction mixture was stirred for 4 h at room temperature. TLC analysis (silica gel, methylene chloride) showed complete consumption of the aldehyde ($R_f$ 0.73). Isopropanol (100 mL) was added and the reaction stirred for 18 h to quench any excess Jones Reagent, resulting in a white suspension over a green-black sludge (chromium salts). The white supernatant was drawn off, and the sludge washed with acetone (5×500 mL). The acetone washes were combined with the supernatant and concentrated on the rotary evaporator to a final volume of 2 L. The residue was poured into ice/water (10 L) and stirred vigorously for 5 h yielding an off-white solid. The material was collected by filtration, washed with water (3×1 L), than vacuum dried to give 665.3 g (quantitative) of the desired carboxylic acid (mp 270°–273° C. (dec)) NMR (d$_6$-DMSO) 13.95 (s, 1H), 7.79 (m) and 7.87 (s, 1H), 7.12–7.45 (m, 6H), 5.27 (d, J=6.4 Hz, 1H), 4.48 (s, 1H), 2.35 (m, 1H), 1.81 (s) and 1.84 (s, 3H), 1.38 (m, 1H) IR max (KBr) 1690 cm$^{-1}$, C=O, —COOH; 1740 cm$^{-1}$, C=O, —COCH$_3$.

e. 12-Acetoxy-2-chloro-9,10-dihydro-9,10-ethano-9-anthracen-9-ylcarbonyl chloride (E and Z isomers)

12-Acetoxy-2-chloro-9,10-dihydro-9,10-ethano-9-anthracenecarboxylic acid (described in Example 1d) (665.0 g, 1.94 mol) was suspended in toluene (8.0 L). Thionyl chloride (400 g, 3.36 mol) was added in one portion at room temperature followed by a catalytic amount (2 mL) of N,N-dimethylformamide. The mixture was heated gradually to reflux (80° C.) over 1 h, then maintained at reflux for 8 h, yielding a clear amber solution. The cooled reaction mixture was concentrated on the rotary evaporator under pump vacuum to remove the toluene. The crude acid chloride was isolated as a waxy brown solid (804, g, 115% of theoretical), and was used crude in the next reaction. A small sample of the material was dried under high vacuum to provide a sample for spectral characterization. NMR (CDCl$_3$) 7.87 (m, 1H), 7.18–7.40 (m, 6H), 5.57 (m, 1H), 4.29 (s, 1H) 2.58 (m, 1H), 1.91 (s) and 1.94 (s, 3H), 1.50 (m, 1H) IR max (neat film): 1750 cm–1, C=O, —COCH$_3$; 1790 cm$^{-1}$, C=O —COCl f. 12-Acetoxy-2-chloro-9,10-dihydro-9,10-ethanoanthracen-9-ylcarboxyl azide (E and Z isomers)

The crude 12-acetoxy-2-chloro-9,10-dihydro-9,10-ethano-9-anthracen- 9-ylcarbonyl chloride (described in Example 1e) (804 g, approx 1.94 mol) was dissolved in acetone (8.0 L) and the resulting solution cooled by an ice/methanol bath to −5° C. The stirred mixture was treated with an aqueous solution of sodium azide (380 g, 5.84 mol in 1.0 L of water) added over a period of 30 min. The resulting tan suspension was stirred for 3 h at 0° C., then allowed to warm to room temperature. The mixture was concentrated on the rotary evaporator at 15°–20° C. using pump vacuum to remove the acetone. The residue was partitioned between water (5 L) and toluene (5 L), stirred for 1 h, then filtered. The two-phase filtrate was separated and the aqueous portion extracted with toluene (5×1 L). The toluene extracts were used to redissolve the filter cake isolated earlier. The combined toluene solutions were washed with brine solution (2 L), then dried over magnesium sulfate. The toluene was filtered, then concentrated to ½ volume on the rotary evaporation at 15°–20° C. under pump vacuum. This gave a toluene solution of the acyl azide (yield assumed to be quantitative), which was used in the next reaction. A small sample of the solution was evaporated under high vacuum to isolate a sample of the acyl azide as an off-white sticky solid for spectral characterization. NMR (CDCl$_3$) 7.80 (m, 1H), 7.16–7.33 (m, 6H), 5.39 (m, 1H), 4.27 (t, J=2.6 Hz, 1H), 2.50 (m, 1H), 1.89 (s) and 1.92 (s, 3H), 1.47 (m, 1H) IR max (Nujol): 1720 cm$^{-1}$, C=O, —CON$_3$; 1750 cm$^{-1}$, C=O, —COCH$_3$: 2160 cm$^{-1}$, —N=N=N g. 12-Acetoxy-2-chloro-9-isocyanato-9,10-dihydro-9,10-ethanoanthracene (E and Z isomers).

The toluene solution of the crude acyl azide isolated in the previous reaction (approx 713.5 g, 1,94 mol in 6.0 L of toluene) was heated gradually over a 30 min period to 65° C. At this point, rapid evolution of nitrogen ensued, accompanied by an exotherm which raised the temperature of the reaction mixture to 95° C. The heating mantle was removed until the exotherm subsided (30 min), after which time the reaction was heated at reflux for 3 h, then allowed to cool. The toluene was removed on the rotary evaporation using pump vacuum, isolating the crude isocyanate as a thick amber oil (738.5 g, 112% of theoretical). This material was used in the next reaction without further purification. A sample of the oil was dried under high vacuum to provide a sample for spectral characterization. NMR (CDCl$_3$) 7.54 (m, 2H), 7.15–7.30 (m, 5H), 5.03 (m, 1H), 4.26 (t, J=2.6 Hz, 1H), 2.55 (m, 1H), 1.98 (s) and 2.00 (s, 3H), 1.56 (m, 1H) IR max (neat film): 1750 cm$^{-1}$, C=O, —COCH$_3$; 2260 cm$^{-1}$, —N=C=O h. 9-Amino-2-chloro-12-hydroxy-9,10-dihydro-9,10-ethanoanthracene (E and Z isomers).

The crude isocyanate from the previous reaction (738.5 g, 1.94 mol) was dissolved in absolute ethanol (7.0 L) giving a light amber solution. The stirred solution was treated with 20% aqueous sodium hydroxide solution (800 g, 20.0 mol in 4.0 L of water) added in one portion at room temperature. The reaction mixture turned red-brown immediately upon addition of the base. The mixture was heated at reflux for 8 h, then cooled. TLC analysis (silica gel, methylene chloride) showed complete consumption of the isocyanate (R$_f$ 0.80). The reaction mixture was concentrated on the rotary evaporator to remove the ethanol, leaving an aqueous suspension of the product which was extracted with methylene chloride (3×5 L). The combined extracts were washed with water (2 L) and brine solution (1 L), then dried over magnesium sulfate. Filtration, followed by removal of the solvent in vacuo, yielded the crude amino alcohol as a sticky yellow-brown solid. Trituration with diethyl ether (1.0 L) afforded the pure compound as a cream colored powder weighing 445.8 g (84.5%) (mp 164°–167° C.). NMR (CDCl$_3$) 7.09–7.43 (m, 7H), 4.21 (t, J=2.6 Hz, 1H), 3.77 (m, 1H), 2.35 (m, 1H), 2.25 (br s, 3H), 1.48 (m, 1H)

i. 2-Chloro-9-formyl-9,10-dihydro-9,10-methanoanthracene.

The 9-amino-2-chloro-12-hydroxy-9,10-dihydro-9,10-ethanoanthracene (described in Example 1h) (445.5 g, 1.64 mol) was dissolved in glacial acetic acid (4.0 L), and the resulting solution cooled to 10° C. A solution of sodium nitrite (340.0 g, 4.93 mol) in water (1.4 L) was added to the reaction mixture over a period of 1.75 h. The temperature of the mixture was maintained at 10° C. during the addition of the nitrite, and for 4 h thereafter. The mixture was then stirred overnight and allowed to warm to room temperature. TLC analysis (silica gel, toluene:ethyl acetate (4:1)) showed complete conversion of the amino alcohol (R$_f$ 0.12) to 2-chloro-9-formyl-9,10-dihydro-9,10-methanoanthracene (R$_f$ 0.80). The reaction mixture was diluted with water (4 L) which caused precipitation of a reddish-brown tar. The aqueous supernatant was decanted away from the tar, diluted with an equal volume of crushed ice, then adjusted to pH 5–6 with solid sodium hydroxide. The resulting aqueous mixture was extracted with ethyl acetate (3×1.5 L). The combined ethyl acetate extracts were used to redissolve the tar, and the resulting solution washed with brine (2×1 L) then dried over magnesium sulfate. Filtration, followed by removal of the solvent in vacuo, gave the crude product as a thick brown oil. Purification of this material by column chromatography over silica gel, eluting with a solvent mixture of methylene chloride:hexane (1:1), afforded a thick yellow oil which crystallized on standing (311.7 g, 74.6%). Trituration with diethyl ether:hexane (1:6, 700 mL) gave a first crop of pure title compound as an off-white crystalline solid weighing 224.1 g (53.6%, mp 91°–92° C.). NMR (CDCl$_3$) 10.39 (s, 1H), 7.50 (d, J=1.9 Hz, 1H), 7.39 (m, 1H), 7.31 (m, 1H), 7.20 (d, J=7.8 Hz, 1H), 7.01 (m, 3H), 4.37 (s, 1H), 2.80 (m, 2H).

Material recovered from the mother liquors and washes was repurified by column chromatography as previously described to give an additional 65.0 (15.5%) of the title compound.

Example 108

This example illustrates the synthesis of an intermediate aldehyde designated as compound 24 in Scheme I, 2-chloro-9,10-dihydro-9,10-methano-9-anthracenecarboxylic acid.

To a cooled solution (0° C.) of 2-chloro-9-formyl-9,10-dihydro-9,10-methanoanthracene (described in Example 106 above) 20.0 g, 78.5 mmol) in acetone (260 mL) was added Jones reagent (24 mL; 27 g chromium trioxide, 23 mL water diluted up to 100 mL of reagent solution) in portions. The reagent was added until an orange color persists. The reaction, containing a significant amount of reduced chromium salts, was warmed to room temperature. The solvents were removed in vacuo and replaced with water (300 mL) saturated with sodium chloride. The aqueous phase was extracted with ethyl acetate (3×300 mL). Combined organic extracts were extracted with 2.5N NaOH (3×400 mL). The basic aqueous extracts were acidified with 3N HCl, saturated with sodium chloride, and extracted with ethyl acetate (4×300 mL). Combined organic extracts were dried over anhydrous magnesium sulfate, filtered, and reduced to a off-white solid. The procedure yielded 26.66 g (quantitative) of the title compound. No additional purification was required. NMR (d$_6$-DMSO, 300 MHz) 13.2 (downfield) 7.46 (br s, 1H), 7.36 (m, 3H), 7.02 (m, 3H), 4.45 (s, 1H), 2.67 (s, 2H) MS (CI, CH$_4$) m/z 271 (M+1,100), 273 (34), 299 (M+29,17), 253 (33), 243 (22), 227 (20)

Example 109 a. This Example illustrates the optical resolution of a racemic acid using (+)-pseudoephedrine.

To a solution of racemic 2-chloro-9,10-dihydro-9,10-methano-9-anthracenecarboxylic acid (described in Example 107) (100 g, 0.37 mol) in ethyl acetate (1.5 L) and methanol (75 mL) was added solid (1S,2S)-(+)-pseudoephedrine (61.1 g, 0.37 mol). With efficient agitation the mixture was warmed to reflux, held at reflux for 30 min and slowly cooled to 25° C. After a minimum of 2 h the slurry was filtered and washed with ethyl acetate to yield enriched diastereomeric salt (88.6 g, 0.20 mol, 55%; diastereomeric ratio 80:20 as determined by HPLC). The enriched salt was slurried in 3% methanolic ethyl acetate (2.74 L), warmed to reflux, and held at reflux for 30 min. The slurry was cooled to 25° C. slowly, stirred for 2 h, filtered, and washed with ethyl acetate to provide additional enriched salt (70 g, 0.16 mol, 79%, diastereomeric ratio 95:5 as determined by HPLC) Treatment of the enriched salt with 5% methanolic ethyl acetate using the same procedure yielded highly enriched salt (60.0 g, 0.14 mol, 85%, diastereomeric ratio 99:1 as determined by HPLC) This salt (60 g, 0.14 mol) was added to water (1 L) and the resulting suspension acidified to pH 2–3 with concentrated hydrochloric acid (15 mL) and then extracted with diethyl ether (3×500 mL). The combined organic extracts were washed with brine, dried over anhydrous magnesium sulfate and evaporated to an oil. Hexane was added and reduced in vacuo to afford enantiomerically enriched acid (36 g, 0.13 mol, 98% recovery, enantiomeric ratio 99:1 as determined by HPLC) as a white solid. Crystallisation from a mixture of hexane (360 mL) and cyclohexane (720 mL) afforded enantiomerically pure (9S,10S)-2-chloro-9,10-dihydro-9,10-methano-9-anthracenecarboxylic acid as a white solid (30 g, 0.11 mol, 81%) mp 172°–173° C. $[\alpha]_D=+101°$ (c=2, CHCl$_3$)

Analysis for $C_{16}H_{11}ClO_2$: Calculated: C, 70.99; H, 4.10 Found C, 70.81; H, 4.21

NMR 7.48–7.62 (m, 2H), 7.27–7.35 (m, 1H), 7.22 (d, J=7.8 Hz, 1H), 6.90–7.10 (m, 3H), 4.35 (s, 1H), 2.80–2.95 (m, 2H)

HPLC analysis: Column: Ultron Ovomucoid (ES-OVM) 15 cm×6 mm Eluent: 15% acetonitrile/85% aqueous KH$_2$PO$_4$ buffer (10 mM) adjusted to pH 5.5 with 1M potassium hydroxide. Flow: 1 mL/min Wavelength: 230 nm Retention times: (+) enantiomer 15.4 min /(−) enantiomer 19.6 min. The (9R,10R) 2-Chloro-9,10-dihydro-9,10-methano-9-anthracenecarboxylic acid was resolved as follows:

b. Using a procedure similar to that described in Example 109a, except employing (1R,2R)-(−)-pseudoephedrine as the resolving agent, the (9R,10R)-(−)-2-chloro-9,10-dihydro-9,10-methano-9-anthracene-carbox-ylic acid was obtained, mp 169°–170° C. $[\alpha]_D=+100.8°$ (c=2.0, CHCl3)

Analysis for $C_{16}H_{11}ClO_2$: Calculated: C, 70.99; H, 4.10 Found: C, 70.75; H, 4.18

NMR 7.48–7.64 (m, 2H), 7.27–7.36 (m, 1H), 7.23 (d, J=7.8 Hz, 1H), 6.90–7.12 (m, 3H), 4.36 (s, 1H), 2.80–2.95 (m, 2H)

Example 110

N-(1-[(9S,10S)-2-Chloro-9,10-dihydro-9,10-methanoanthracen-9-yl-methyl]-4-(piperidyl)-2,2-diethoxyacetamide hydrochloride Using a procedure similar to that described in Example 5 except starting with the free base of Example 18 and reacting for 5 minutes with ethereal hydrogen chloride, the title compound was obtained as a white solid (71%), mp 215°–7° C.; MS(CI): 469 (M+H); H-NMR (300 MHz, DMSO-d$_6$): 1.34 (t, J=7.0 Hz, 4.6H), 1.18(t, J=7.0 Hz, 1.4H), 1.91(br m, 4H), 2.74(m, 2H), 3.47–3.67(m, 8H), 3.83(m, 0.8H), 4.01(m, 0.2H), 4.20–4.42(m, 2H), 4.78(s, 1H), 4.70(s, 0.8H), 4.80(s, 0.2H), 6.96–7.09(m, 3H), 7.30–7.39(m, 3H), 7.46(d, J=1.6 Hz, 0.2H), 7.49(d, J=1.6 Hz, 0.8H), 7.98(d, J=7.5 Hz, 0.2H), 8.08(d, J=7.5 Hz, 0.8H), 9.79(br s, 0.2H), 10.00(br s, 0.8H).

Analysis for $C_{27}H_{33}ClN_2O_3 \cdot 1.0HCl \cdot 0.5H_2O$ Calculated: C, 63.03; H, 6.86; N, 5.44 Found: C, 63.22; H, 6.79; N, 5.38

Example 111

N-(1-[(9S,10S)-2-Chloro-9,10-dihydro-9,10-methanoanthracen-9-yl-methyl]-4-(piperidyl)-2-(2,2,2-trifluoroethoxy)acetamide hydrochloride Using a similar procedure to that described in Example 1 except starting with 2-(2,2,2-trifluoroacetic acid), the free base of the title compound was obtained. This material was treated with ethereal hydrogen chloride using a similar procedure as describe in Example 5, the title compound was obtained as a colorless solid, mp 106°–110.5° C.; MS(CI): 479(M+H); H-NMR (300 MHz, DMSO-d$_6$): 1.48(m, 2H), 1.65(m, 2H), 2.27(m, 2H), 2.30(m, 2H), 2.46(m, 2H), 2.93(m, 2H), 3.63(m, 1H), 4.03(s, 2H), 4.13(q, J=9.3 Hz, 2H), 4.33(s, 1H), 6.94(m, 3H), 7.23(m, 4H), 7.69(d, J=8.3 Hz, 1H).

Analysis for $C_{25}H_{26}ClF_3N_2O_2 \cdot 1.0HCl \cdot 1.75H_2O$ Calculated: c, 54.90; H, 5.62; N, 5.12 Found: C, 54.80; H, 5.47; N, 5.06

The starting 2-(2,2,2-trifluoroethoxyacetic acid was obtained as follows:

a) Methyl 2-(2,2,2-trifluoroethoxy)acetate.

To a mixture of sodium hydride (1.648 g, 68.66 mmol) in tetrahydrofuran (220 mL) at 0° C. was added 2,2,2-trifluoroethanol (5.0 mL, 68.66 mmol). After 5 minutes, the reaction was allowed to warm to room temperature and methyl 2-bromoacetate (6.2 mL, 65.39 mmol) was added. After stirring for 72 hours, the mixture was filtered through diatomaceous earth with ether washes. The filtrate was concentrated and distilled to afford the title compound as a colorless oil (8.26 g, 73%), bp 155°–60° C., MS(CI): 173(M+H); H-NMR (300 MHz, DMSO-d$_6$): 3.68(s, 3H), 4.16(q, J=9.2 Hz, 2H), 4.33(s, 2H).

b) 2-(2,2,2-Trifluoroethoxy)acetic acid.

To a solution of methyl 2-(2,2,2-trifluoroethoxy)acetate (8.26 g, 47.98 mmol) and methanol (16 mL) was added sodium hydroxide (1.92 g, 47.98 mmol) in methanol (16 mL). After stirring for 18 hours, the reaction was concentrated and ether (170 mL) was added. The mixture was cooled to 0° C. and concentrated sulfuric acid (2.15 g, 43.9 mmol) in ether (7.5 mL) was slowly added. The resulting mixture was stirred for 18 hours, filtered and concentrated to give the title compound as a colorless oil (7.15 g, 94%), MS(CI): 159(M+H); H-NMR (300 MHz, DMSO-d$_6$): 4.14(q, J=9.3 Hz, 2H), 4.21(s, 2H), 12.92(s, 1H).

Example 112

N-(1-[(9S,10S)-2-Chloro-9,10-dihydro-9,10-methanoanthracen-9-yl-methyl]-4-(piperidyl)-2-methoxy-2-methylpropionamide hydrochloride Using a procedure to that described in Example 1 except starting with 2-methoxy-2-methylpropionic acid, the free base of the title compound was obtained. This was treated with ethereal hydrogen chloride (described in Example 5) to give the title compound was obtained as a yellow solid (68%), mp 167.5°–180.0° C.; MS(CI): 439(M+H);

H-NMR (300 MHz, DMSO-d$_6$): 1.22(s, 6H), 1.42–1.66(m, 4H), 2.25(m, 2H), 2.48(m, 2H), 2.94(m, 2H), 3.10(s, 3H), 3.31(s, 2H), 3.57(m, 1H), 4.33(s, 1H), 6.94(m, 3H), 7.18–7.28(m, 4H), 7.45(d, J=8.2 Hz, 1H).

Analysis for $C_{26}H_{31}ClN_2O_2 \cdot 1.0HCl \cdot 1.0H_2O$ Calculated: C, 63.28; H, 6.94; N, 5.68 Found: C, 63.33; H, 6.61; N, 5.58

The starting 2-methoxy-2-methylpropionic acid was obtained as follows:

a. 2-Methoxy-2-methylpropionic acid.

To a mixture of sodium hydride (3.13 g, 130.5 mmol) in tetrahydrofuran at 0° C. was added methanol (5.3 mL, 130.5 mmol) and allowed to warm to room temperature. The reaction was cooled to 0° C. and 2-bromo-2-methylpropionyl bromide (5.4 mL, 43.5 mmol) was added. After warming to room temperature, the reaction was heated to 45° C. for 42 hours and then cooled to room temperature. The resulting mixture was filtered through diatomaceous earth with ether wash and the solvent was distilled off. The pot residue was partitioned between ether and 1N hydrochloric acid. The organic layer was dried (magnesium sulfate), filtered and concentrated to give methyl 2-methoxy-2-methylpropionate and 2-methoxy-2-methylpropionic acid (2.47 g). This mixture of products was treated with methanolic sodium hydroxide, using a similar procedure to that described in Example 111b and distillation, the title compound was obtained as a colorless oil (650 mg, 12.6%), bp 85°–95° C./20 mm; MS(CI): 119(M+H); H-NMR (300 MHz, DMSO-$d_6$): 1.29(s, 6H), 3.14(s, 3H), 12.52(s, 1H).

Example 113

N-(1-[(9S,10S)-2-Chloro-9,10-dihydro-9,10-methanoanthracen-9-yl-methyl]-4-(piperidyl)-2-(2-fluoroethoxy)acetamide Using a similar procedure to that described in Example 1 except starting with 2-(2-fluoroethoxy)acetic acid, the title compound was obtained as a white foam (75%), mp 50.0°–5.5° C.; MS(CI): 443(M+H);

H-NMR (300 MHz, DMSO-$d_6$): 1.46(m, 2H), 1.64(m, 2H), 2.28(m, 2H), 2.47(m, 2H), 2.94(,m, 2H), 3.30(m, 2H, submerged by $H_2O$), 3.63(m, 2H), 3.37(t, J=4.0 Hz, 1H), 3.88(s, 2H), 4.34(s, 1H), 4.47(t, J=4.0 Hz, 1H), 4.63(t, J=3.8 Hz, 1H), 6.94(m, 3H), 7.26(m, 4H), 7.52(d, J=8.2 Hz, 1H).

Analysis for $C_{25}H_{28}ClFN_2O_2.0.25H_2O$ Calculated: C, 67.10; H, 6.42; N, 6.26 Found: C, 66.91; H, 6.44; N, 6.13

The starting 2-(2-fluoroethoxy)acetic acid was obtained as follows:
a. Methyl 2-(2-fluoroethoxy)acetate.

Using a similar procedure to that described in Example 111a except starting with 2-fluoroethanol, the title compound was obtained as colorless oil (45%), bp 160°–77° C.; MS(CI): 137(M+H); H-NMR (300 MHz, DMSO-$d_6$): 3.66(s, 3H), 3.68(m, 1H), 3.78(m, 1H), 4.18(s, 2H), 4.46(m, 1H), 4.62(m, 1H).
b. 2-(2-Fluoroethoxy)acetic acid.

Using a similar procedure to that described in Example 111b except starting with methyl 2-(2-fluoroethoxy)acetate, the title compound obtained as a colorless oil (94%), MS(CI): 123(M+H); H-NMR (300 MHz, DMSO-$d_6$): 3.67(m, 1H), 3.77(m, 1), 4.06(s, 2H), 4.45(m, 1H), 4.62(m, 1H), 12.65(s, 1H).

Example 114

N-(1-[(9S,10S)-2-Chloro-9,10-dihydro-9,10-methanoanthracen-9-yl-methyl]-4-(piperidyl)-2,2-dimethoxypropionamide hydrochloride Using a similar procedure to that described in Example 1 except starting with 2,2-dimethoxypropionic acid, the free base of the title compound was obtained. Treatment with ethereal hydrogen chloride, using a similar procedure to that described in Example 5, afforded the title compound as a colorless solid (44%), mp 246°–8° C.; MS(CI): 455(M+H); H-NMR (300 MHz, DMSO-$d_6$): 1.29(s, 3H), 1.60(m, 4H), 2.26(m, 2H), 2.47(m, 2H), 2.94(m, 2H), 3.09(s, 6H), 3.31(s, 2H), 3.61(m, 1H), 4.34(s, 1H), 6.94(m, 3H), 7.18–7.28(m, 4H), 7.57(d, J=8.2 Hz, 1H).

Analysis for $C_{26}H_{31}ClN_2O_3.1.0HCl$ Calculated: C, 63.54; H, 7.56; N, 5.70 Found: C, 63.18; H, 6.50; N, 5.59

The starting 2,2-dimethoxypropionic acid was obtained as follows:
a. Using a similar procedure to that described in Example 111b except starting with methyl 2,2-dimethoxypropionate, the title compound was obtained as a colorless oil (75%), MS(CI): 103(M+H); H-NMR (300 MHz, DMSO-$d_6$): 1.37(s, 3H), 3.13(s, 6H).

Example 115

N-(1-[2-Chloro-9,10-dihydro-9,10-methanoanthracen-9-yl-methyl]-4-(piperidyl)-2-(2-methoxyethoxy)acetamide Using a similar procedure to that described in Example 21 except starting with 2-(2-methoxyethoxy)acetic acid, the title compound was obtained as a colorless solid (22%), mp 106°–9.5° C.; MS(CI): 455(M+H); H-NMR (300 MHz, DMSO-$d_6$): 1.46(m, 2H), 1.67(m, 2H), 2.29(q, J=9.9 Hz, 2H), 2.47(br s, 2H), 2.92(m, 2H), 3.25(s, 2H), 3.32(m, 2H, submerged by $H_2O$), 3.47(m, 2H), 3.54(m, 2H), 3.62(m, 2H), 3.83(s, 2H), 4.34(s, 1H), 6.95(m, 3H), 7.23(br m, 4H), 7.49(d, J=7.8 Hz, 1H).

Analysis for $C_{26}H_{31}ClN_2O_3$ Calculated: C, 68.63; H, 6.87; N, 6.16 Found: C, 68.95; H, 6.75; N, 6.11

Example 116

N-(1-[2-Chloro-9,10-dihydro-9,10-methanoanthracen-9-yl-methyl]-4-(piperidyl)-2-(4-tetrahydropyranyloxy)acetamide Using a similar procedure to that described in Example 21 except starting with 2-(4-tetrahydropyranyloxy)acetic acid, the free base of the title compound was obtained. Treatment with ethereal hydrogen chloride using a similar procedure to that described in Example 5, the title compound was obtained as a colorless solid (27%), mp 168.5°–72.0° C.; MS(CI): 481(M+H); H-NMR (300 MHz, DMSO-$d_6$): 1.39–1.53(m, 6H), 1.61(m, 2H), 1.83(m, 2H), 2.29(m, 2H), 2.47(m, 2H), 2.94(m, 2H), 3.33(m, 3H), 3.50(m, 1H), 3.63(m, 1H), 3.78(t, J=4.1 Hz, 1H), 3.81(t, J=4.1 Hz, 1H), 3.85(s, 2H), 4.33(s, 1H), 6.94(m, 3H), 7.25(m, 4H), 7.43(d, J=8.4 Hz, 1H).

Analysis for $C_{28}H_{33}ClN_2O_3.1.0HCl.1.5H_2)$ Calculated: C, 61.76; H, 6.84; N, 5.14 Found: C, 61.70; H, 6.52; N, 4.81

Example 117

Epimer I of N-(1-[(9S,10S)-2-chloro-9,10-dihydro-9,10-methanoanthracen-9-ylmethyl]-4-(piperidyl)-2-cyclopentyl-2-methoxyacetamide hydrochloride Using a procedure similar to that described in Example 1, except starting with enantiomer I of 2-cyclopentyl-2-methoxyacetic acid and chromatography (eluant: 94:5:1 v/v/v methylene chloride:methanol:ammonium hydroxide), the free base of the title compound was obtained as a solid. Treatment of this material with ethereal hydrogen chloride, using a similar procedure described in Example 5, the title compound was obtained as a colorless solid (50%), mp 192°–3° C.; MS(CI): 479(M+H); H-NMR (300 MHz, DMSO-$d_6$): 1.35–1.65(m, 8H), 1.85–2.15(m, 5H), 2.72(s, 2H), 3.21(s,3H), 3.30–3.57(m, 5H), 3.87(br s, 1H), 4.22–4.40(m, 2H), 4.48(s, 1H), 7.02(m, 3H), 7.34(m, 3H), 7.48(s, 1H), 8.11(d, J=7.44 Hz, 1H), 9.75(br s, 1H).

Analysis for $C_{29}H_{35}ClN_2O_2.1.0HCl.0.75H_2O$ Calculated: C, 65.84; H, 7.14; N, 5.30 Found: C, 65.72; H, 7.09; N, 5.21

The starting enantiomer I of 2-cyclopentyl-2-methoxyacetic acid was obtained as follows:
a. 2-Cyclopentyl-2-methoxyacetyl chloride.

To a stirred cold (ice bath) solution of 2-cyclopentyl-2-methoxyacetic acid, methyl chloride and N,N-dimethylformamide at 0° C. was added oxalyl chloride. After 2 hours, the reaction was concentrated at room temperature to give the title compound as a light yellow oil (889 mg, 88%).

b. Epimer I of 3-[2-cyclopentyl-2-methoxyacetyl]-(4R,5S)-4-methyl-5-phenyl-2-oxazolidin-2-one and epimer II of 3-[2-cyclopentyl-2-methoxy-acetyl]-(4R,5S)-4-methyl-5-phenyl-2-oxazolidin-2-one.

To a mixture of (4R,5S)-(+)-4-methyl-5-phenyloxazolidin-2-one (874 mg, 4.93 mmol) and tetrahydrofuran (10 mL), at −70° C., was added 1.4M n-butyl lithium (3.7 mL, 5.18 mmol) and stirred for 15 minutes. The reaction was added 2-cyclopentyl-2-methoxyacetyl chloride (889 mg, 5.03 mmol) in tetrahydrofuran (1 mL), stirred for 15 minutes at −70° C. and then at 0° C. for 2 hours. The reaction was quenched with saturated ammonium chloride (10 mL) and extracted wtih methylene chloride (75 mL). The organic layer was washed with saturated sodium bicarbonate (2×50 mL) and brine (25 mL) and dried (sodium sulfate), filtered, and concentrated to give a yellow syrup. Chromatography of this material over silica gel (eluant: 8:2 v/v hexane/ethyl acetate) provided the title compounds.

Epimer I of 3-[2-cyclopentyl-2-methoxyacetyl]-(4R,5S)-4-methyl-5-phenyl-2-oxazolidin-2-one was obtained as a colorless syrup (553 mg, 35%), Rf: 0.3 (eluant: 8:2 v/v hexane:ethyl acetate); MS(CI): 318 (M+H); H-NMR (300 MHz, DMSO-$d_6$): 0.81(d, J=6.6 Hz, 3H), 1.45–1.60(br m, 8H), 2.27(m, 1H), 3.23(s, 3H), 4.83(t, J=6.8 Hz, 1H), 4.92(d, 4.74 Hz, 1H), 5.93(d, J=7.3 Hz, 1H), 7.41(br m, 5H).

Epimer II of 3-[2-cyclopentyl-2-methoxyacetyl]-(4R,5S)-4-methyl-5-phenyl-2-oxazolidin-2-one was obtained as a colorless semi-solid (345 mg, 22%), Rf: 0.5(eluant: 8:2 v/v hexane:ethyl acetate); MS(CI): 318 (M+H); H-NMR (300 MHz, DMSO-$d_6$): 0.73(d, J=6.6 Hz, 3H), 1.40–1.65(br m, 8H), 2.29(br m, 1H), 3.26(s, 3H), 4.90(m, 2H), 5.93(d, J=7.7 Hz, 1H), 7.40(br m, 5H).

c. Enantiomer I of 2-cyclopentyl-2-methoxyacetic acid.

To a mixture of epimer I of 3-[2-cyclopentyl-2-methoxy-acetyl]-(4R,5S)-4-methyl-5-phenyl-2-oxazolidin-2-one (425 mg, 1.34 mmol), distilled water (6.7 mL) and tetrahydrofuran (20.3 mL), at 0° C., was added sequentially 8.82M of 30% hydrogen peroxide (0.91 mL, 8.03 mmol) and lithium hydroxide (113 mg, 2.68 mmol). After stirring for 2 hours, the reaction was allowed to warm to room temperature and stirred for 18 hours. The mixture was cooled to 0° C. and quenched with 1.5N sodium sulfite (5.9 mL, 8.85 mmol) and basified to pH 8–9 with saturated sodium bicarbonate. The organic solvent was removed under aspirator pressure and the mixture was extracted with methylene chloride (2×25 mL). The resulting aqueous layer was acidified to pH 2 with 1N hydrochloride and extracted with methylene chloride (2×25 mL). These final organic extracts were combined, dried (sodium sulfate), filtered and concentrated to give the title compound as a colorless syrup (195 mg, 93%), MS(CI): 159(M+H); H-NMR (300 MHz, DMSO-$d_6$): 1.27–1.66(m, 8H), 2.04–2.18(m, 1H), 3.24(s, 3H), 3.50(d, J=6.6 Hz, 1H), 12.57(s, 1H).

Example 118

Epimer II of N-(1-N-(1-[(9S,10S)-2-chloro-9,10-dihydro-9,10-methanoanthracen-9-ylmethyl]-4-(piperidyl)-2-cyclopentyl-2-methoxyacetamide hydrochloride Using a procedure similar to that described in Example 1, except starting with enantiomer II of 2-cyclopentyl-2-methoxyacetic acid, the free base of the title compound was obtained as a solid. Treatment of this material with ethereal hydrogen chloride, using a similar procedure described in Example 5, the title compound was obtained as a colorless solid (65%), mp 238°–40° C.; MS(CI): 479(M+H); H-NMR (300 MHz, DMSO-$d_6$): 1.35–1.65(m, 8H), 1.85–2.15(m, 5H), 2.72(s, 2H), 3.21(s, 3H), 3.30–3.57(m, 5H), 3.87(br s, 1H), 4.22–4.40(m, 2H), 4.48(s, 1H), 7.02(m, 3H), 7.34(m, 3H), 7.48(s, 1H), 8.11(d, J=7.44 Hz, 1H), 9.75(br s, 1H).

Analysis for $C_{29}H_{35}ClN_2O_2 \cdot 1HCl \cdot 0.75H_2O$ Calculated: C, 65.84; H, 7.14; N, 5.30 Found: C, 65.93; H, 6.98; N, 5.23

The starting enantiomer II of 2-cyclopentyl-2-methoxyacetic acid was obtained as follows:

a. Enantiomer II of 2-cyclopentyl-2-methoxyacetic acid.

Using a procedure similar to that described in Example 117c except starting with epimer II of 3-[2-cyclopentyl-2-methoxyacetyl]-(4R,5S)-4-methyl-5-phenyl-2-oxazolidin-2-one (described in Example 117b), the title compound was obtained as a light yellow syrup (94%), MS(CI): 159(M+H); H-NMR (300 MHz, DMSO-$d_6$): 1.27–1.66(m, 8H), 2.04–2.18(m, 1H), 3.24(s, 3H), 3.50(d, J=6.6 Hz, 1H), 12.57(s, 1H).

Example 119

Epimer I of N-(1-[(9S,10S)-2-chloro-9,10-dihydro-9,10-methanoanthracen-9-ylmethyl]-4-(piperidyl)-2-ethoxypropionamide hydrochloride Using a procedure similar to that described in Example 1, except starting with enantiomer I of 2-ethoxypropionic acid and chromatography (eluant: 94:5:1 v/v/v methylene chloride:methanol:ammonium hydroxide), the free base of the title compound was obtained as a solid. Treatment of this material with ethereal hydrogen chloride, using a similar procedure described in Example 5, the title compound was obtained as a light yellow solid (13.5%), mp 180°–2° C.; MS(CI): 439(M+H); H-NMR (300 MHz, DMSO-$d_6$): 1.11(t, J=8.02 Hz, 3H), 1.19(d, J=6.65 Hz, 2H), 1.90(m, 4H), 2.73(s, 2H), 3.25–3.60(m, 6H), 3.76(q, J=6.62 Hz, 1H), 3.85(m, 1H), 4.22–4.42(br m, 2H), 4.48(s, 1H), 7.03(m, 3H), 7.33(m, 3H), 7.49(s, 1H), 7.97(d, J=7.48 Hz, 1H), 9.85(br s, 1H).

Analysis for $C_{25}H_{29}ClN_2O_2 \cdot 1.0HCl \cdot 1.0H_2O$ Calculated: C, 63.28; H, 6.94; N, 5.68 Found: C, 63.15; H, 6.61; N, 5.64

The starting enantiomer I of 2-ethoxypropionic acid was obtained as follows:

a. 2-Ethoxypropionyl chloride.

Using a procedure similar to that described in Example 117a except starting wtih 2-ethoxypropionic acid, the title compound was obtained as a light yellow oil (45%).

b. Epimer I of 3-[2-ethoxypropionyl]-(4R,5S)-4-methyl-5-phenyl-2-oxazolidin-2-one and epimer II of 3-[2-ethoxypropionyl]-(4R,5S)-4-methyl-5-phenyl-2-oxazolidin-2-one.

Using a procedure similar to that described in Example 117b except starting with 2-ethoxypropionyl chloride, the title compounds were obtained as a mixture. This material was high pressure liquid chromatographed (Chiracel OD, 50 cm×50 mm, 54 ml/minute, eluant: 6:4 v/v hexane:ethanol) to afford the title compounds.

Epimer I of 3-[2-ethoxypropionyl]-(4R,5S)-4-methyl-5-phenyl-2-oxazolidin-2-one was obtained as a (3%), Rt: 11.5 minutes; MS(CI): 278(M+H); H-NMR (300 MHz, DMSO-$d_6$): 0.74(d, J=6.5 Hz, 3H), 1.12(dd, J=6.9 Hz, 3H), 1.30(d, J=6.6 Hz, 3H), 3.43(m, 2H), 4.85(br t, J=7.4 Hz, 1H), 4.94(q, J=6.5 Hz, 1H), 5.95(d, J=7.47 Hz, 1H), 7.42(m, 5H).

Epimer II of 3-[2-ethoxypropionyl]-(4R,5S)-4-methyl-5-phenyl-2-oxazolidin-2-one was obtained as a (11%), Rt: 18 minutes; MS(CI): 278(M+H); H-NMR (300 MHz, DMSO-$d_6$): 0.79(d, J=6.6 Hz, 3H), 1.10(t, J=7.0 Hz, 3H), 1.31(d, J=6.6 Hz, 3H), 3.41(m, 2H), 4.81(quintet, J=6.8 Hz, 1H), 5.02(q, J=6.6 Hz, 1H), 5.91(d, J=7.4 Hz, 1H), 7.40(m, 5H).

c. Enantiomer I of 2-ethoxypropionic acid.

Using a procedure similar to that described in Example 117c except starting with epimer I of 3-[2-ethoxypropionyl]-(4R,5S)-4-methyl-5-phenyl-2 -oxazolidin-2-one, the title compound was obtained as a milky white oil (100%), MS(CI): 119(M+H); H-NMR (300 MHz, DMSO-$d_6$): 1.10(t, J=5.0 Hz, 3H), 1.22(d, J=5.4 Hz, 2H), 3.27–3.42(m, 1H), 3.45–3.56(m, 1H), 3.86(q, J=5.4 Hz, 1H), 12.55(s, 1H).

Example 120

Epimer II of
N-(1-[(9S,10S)-2-chloro-9,10-dihydro-9,10-methanoanthracen-9-ylmethyl]-4 -(piperidyl)-2-ethoxypropionamide hydrochloride Using a procedure similar to that described in Example 1, except starting with enantiomer II of 2-ethoxypropionic acid followed by chromatography (eluant: 94:5:1 v/v/v methylene chloride:methanol:ammonium hydroxide), the free base of the title compound was obtained as a solid. Treatment of this material with ethereal hydrogen chloride, using a similar procedure described in Example 5, the title compound was obtained as a light yellow solid (37%), mp 185°–6° C.; MS(CI): 439(M+H); H-NMR (300 MHz, DMSO-$d_6$): 1.11(t, J=7.02 Hz, 3H), 1.19(d, J=6.65 Hz, 2H), 1.90(m, 4H), 2.73(s, 2H), 3.25–3.60(m, 6H), 3.76(q, J=6.62 Hz, 1H), 3.85(m, 1H), 4.22–4.42(br m, 2H), 4.48(s, 1H), 7.03(m, 3H), 7.33(m, 3H), 7.49(s, 1H), 7.97(d, J=7.48 Hz, 1H), 9.85(br s, 1H).

Analysis for $C_{25}H_{29}ClN_2O_2 \cdot 1.0HCl \cdot 1.25H_2O$ Calculated: C, 62.71; H, 6.98; N, 5.63 Found: C, 62.49; H, 6.57; N, 5.44

The starting enantiomer II of 2-ethoxypropionic acid was obtained as follows:

Enantiomer II of 2-ethoxypropionic acid.

Using a procedure similar to that described in Example 117c except starting with epimer II of 3-[2-ethoxypropionyl]-(4R,5S)-4-methyl-5-phenyl-2 -oxazolidin-2-one, the title compound was obtained as a colorless oil (21%), MS(CI): 119(M+H); H-NMR (300 MHz, DMSO-$d_6$): 1.10(t, J=5.0 Hz, 3H), 1.22(d, J=5.4 Hz, 2H), 3.27–3.42(m, 1H), 3.45–3.56(m, 1H), 3.86(q, J=5.4 Hz, 1H), 12.55(s, 1H).

Example 121

N-(1-[9,10-Dihydro-9,10-methanoanthracen-9-ylmethyl]-4-(piperidyl)-2-hydroxy-2 -methylpropionamide To a −20° C. stirred solution of 2-hydroxyisobutyric acid (468 mg, 4.5 mmol) and N,N-diisopropylethylamine (0.84 mL, 4.8 mmol) in N,N-dimethylacetamide (30 mL was added thionyl chloride (0.35 mL, 4.8 mmol). After stirring the reaction for 1 hour, the mixture was allowed to warm to room temperature. The reaction was basified with 1N sodium hydroxide and extracted with methylene chloride (3×70 mL). The combined organic layers was dried (sodium sulfate), filtered, and concentrated to a yellow oil. Chromatography of this material over silica gel (eluant: 2:98 v/v methanol:methylene chloride) and hot trituration with ether provided the title compound as a colorless solid (260 mg, 22%), mp 224.5°–5° C.; MS(CI): 391(M+H); H-NMR (300 MHz, DMSO-$d_6$): 1.21(s, 6H), 1.46(m, 2H), 1.65(m, 2H), 2.28(m, 2H), 2.45(s, 2H), 2.94(br m, 2H), 3.33(s, 2H, submerged by H$_2$O), 3.54(br s, 1H), 4.31(s, 1H), 5.32(s, 1H), 6.91(m, 4H), 7.18(d, J=6.4 Hz, 2H), 7.26(d, J=5.8 Hz, 2H), 7.32(d, J=7.9 Hz, 1H).

Analysis for $C_{25}H_{30}N_2O_2 \cdot 0.25H_2O$ Calculated: C, 76.01; H, 7.78; N, 7.09 Found: C, 75.73; H, 7.75; N, 6.89

Example 122

N-(1-[2-(Chloro-9,10-dihydro-9,10-methanoanthracen-9-ylmethyl]-4-(piperidyl)-2 -(4-methylpyridyl)acetamide Using a similar procedure to that described in Example 6 except starting with 2-(4-methylpyridyl)acetic acid-hydrochloride-lithium chloride, the title compound was obtained as a light yellow solid (25%), mp 66°–71° C.; MS(CI): 473(M+H); H-NMR (250 MHz, DMSO-$d_6$): 1.30–1.48(m, 2H), 1.61–1.74(m, 2H), 2.20–2.35(m, 2H), 2.28(s, 3H), 2.44–2.54(m, 2H, submerged by DMSO), 2.85–3.00(m, 2H), 3.25–3.40(m, 2H, submerged by H$_2$O), 3.48–3.62(m, 1H), 3.52(s, 2H), 4.34(s, 1H), 6.90–7.30(m, 7H), 7.06(d, J=4.3 Hz, 1H), 7.13(s, 1H), 8.00(d, J=7.5 Hz, 1H), 8.30(d, J=4.3 Hz, 1H).

Analysis for $C_{29}H_{30}ClN_3O \cdot 0.5H_2O$ Calculated: C, 72.41; H, 6.49; N, 8.73 Found: C, 72.41; H, 6.27; N, 7.99

The starting 2-(4-methylpyridyl)acetic acid-hydrochloride-lithium chloride was obtained as follows:

a. 2-(4-Methylpyridyl)acetic acid-hydrochloride-lithium chloride.

To a 0° C. mixture of 2,4-dimethylpyridine (5.36 mL, 46.36 mmol) and ether (75 mL) was added 1.8M phenyl lithium in cyclohexane-ether (27.8 mL, 50.04 mmol). After 1 hour, the reaction was poured into powdered dry ice and allowed to warm to room temperature. The resulting solid was added ether and the solid was broken up. The solid was filtered off, suspended in methylene chloride (25 mL) and treated with gaseous hydrogen chloride until the solid turned into a fine powder. The resulting solid was filtered, vacuum dried (stored under nitrogen) to afford the title compound as a highly hydroscopic yellow solid (35%), H-NMR (250 MHz, DMSO-$d_6$): 2.55(s, 3H), 4.16(s, 2H), 7.72(br d, J=5.9 Hz, 1H), 7.78(br s, 1H), 8.68(d, J=5.9 Hz, 1H).

Example 123

1-[(9S,10S)-2-Chloro-9,10-Dihydro-9,10-methanoanthracen-9-ylmethyl)-4 -piperidyl]-3-(4-morpholinyl)urea Using a procedure similar to that described in Example 78 except starting with 4-amino-1-[(9S,10S)-2-chloro-9,10-dihydro-9,10 -methanoanthracen-9-ylmethyl)-4-piperidine and morpholine and reacting at refluxing temperature, the title compound was obtained as a colorless solid (41%), mp 149.5°–155.0° C.; MS(CI): 452(M+H); H-NMR (300 MHz, DMSO-$d_6$): 1.41(m, 2H), 1.65(m, 2H), 2.23(q, J=10.8 Hz, 2H), 2.47(m, 2H), 2.95(m, 2H), 3.22(t, J=4.8 Hz, 4H), 3.33(m, 3H, submerged by H$_2$O), 3.50(m, 4H), 4.33(s, 1H), 6.18(d, J=7.6 Hz, 1H), 6.95(m, 3H), 7.24(m, 4H).

Analysis for $C_{26}H_{30}ClN_3O_2 \cdot 1.0C_2H_2O_4 \cdot 1.25H_2O$ Calculated: C, 59.57; H, 6.16; N, 7.44 Found: C, 59.60; H, 4.84; N, 7.28

Example 124

2-(1-Oxypyridyl)methyl N-(1-[9,10-Dihydro-9,10-methanoanthracen-9-ylmethyl]-4-piperidyl)carbamate Using a procedure similar to that described in Example 78 except starting with and 2-(N-oxypyridyl)methanol[1] and reacting at refluxing temperature, the title compound was obtained as a colorless solid (68%), mp 155.5°–7.5° C.; MS(CI): 456(M+H); H-NMR (300 MHz, DMSO-$d_6$): 1.40(m, 2H), 1.72(m, 2H), 2.60(t, J=11.4 Hz, 2H), 2.45(br s, 2H), 2.95(m, 2H), 3.31(m, 3H, submerged by $H_2O$), 4.31(s, 1H), 5.10(s, 2H), 6.92(m, 4H), 7.18(m, 2H), 7.26(m, 2H), 7.40(m, 3H), 7.47(d, J=7.8 Hz, 1H), 8.30(m, 1H).

1. N. Hata, *Bull. Chem. Soc. Jpn.*, 1958, 31, 224.

Analysis for $C_{28}H_{29}N_3O_3 \cdot 0.25H_2O$ Calculated: C, 73.10; H, 6.46; N, 9.13 Found: C, 73.00; H, 6.50; N, 9.18

Example 125

The following illustrate representative pharmaceutical dosage forms containing a compound of formula I, for example as illustrated in any of the previous Examples, (hereafter referred to as "compound X"), for therapeutic or prophylactic use in humans:

|  | mg/tablet |
|---|---|
| (a) Tablet | |
| Compound X | 50.0 |
| Mannitol, USP | 223.75 |
| Croscarmellose sodium | 6.0 |
| Maize starch | 15.0 |
| Hydroxypropylmethylcellulose (HPMC), USP | 2.25 |
| Magnesium stearate | 3.0 |
| (b) Capsule | |
| Compound X | 10.0 |
| Mannitol, USP | 488.5 |
| Croscarmellose sodium | 15.0 |
| Magnesium stearate | 1.5 |

The above formulations may be obtained by conventional procedures well known in the pharmaceutical art. The tablets may be enteric coated by conventional means, for example to provide a coating of cellulose acetate phthalate.

Chemical Formulae

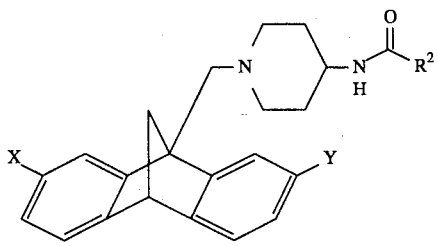

I

-continued
Chemical Formulae

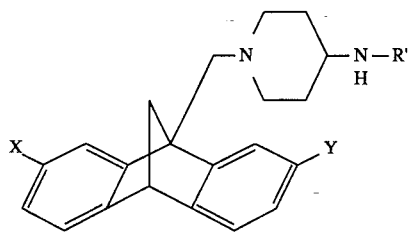

Ia

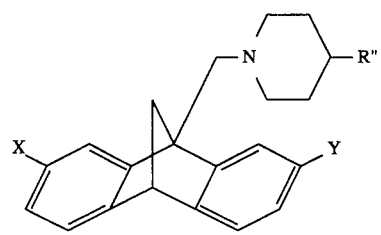

Ib

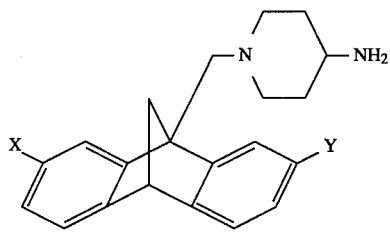

II

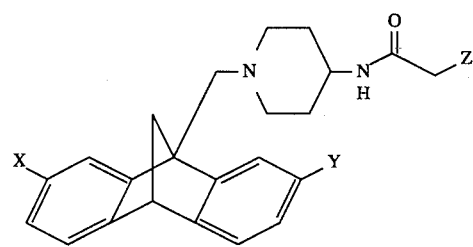

III

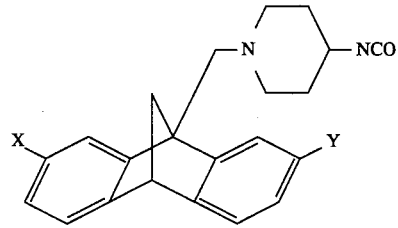

IV

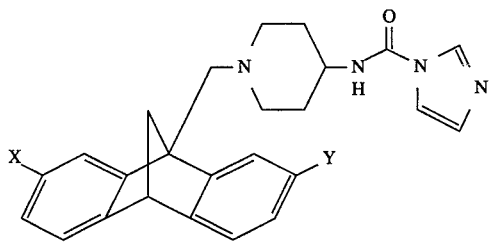

V

-continued
Chemical Formulae
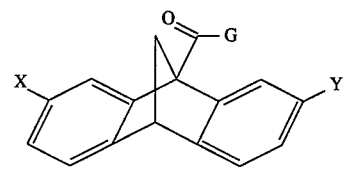
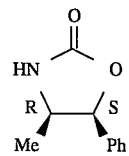
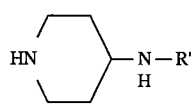
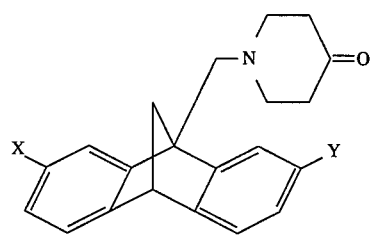
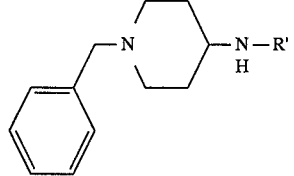
Scheme I
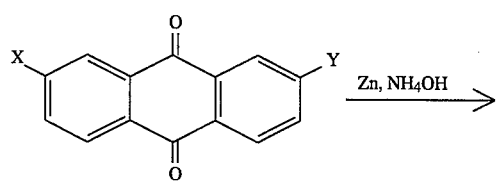
10
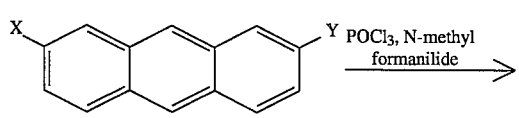
12
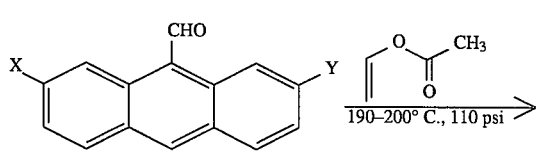
14
-continued
Scheme I
VI
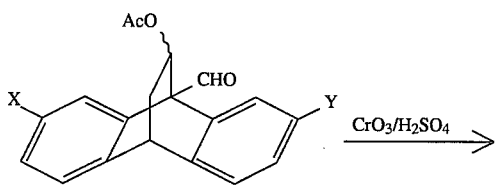
16
VII
VIII
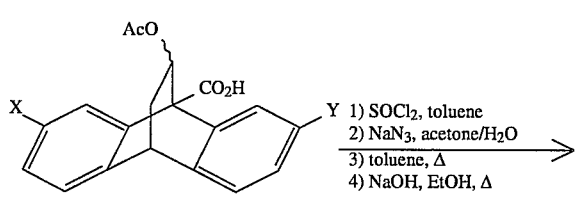
18
IX
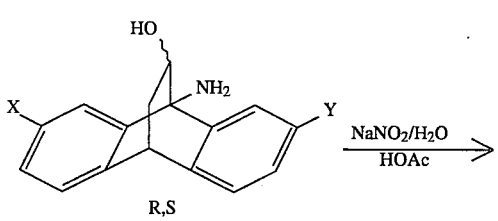
20
XI
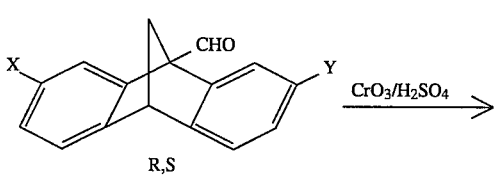
22
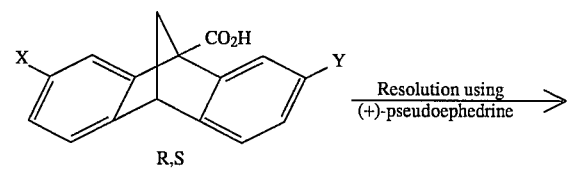
24
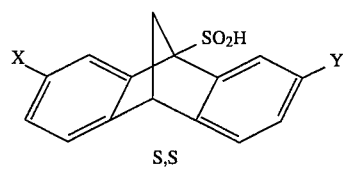
26

Scheme II

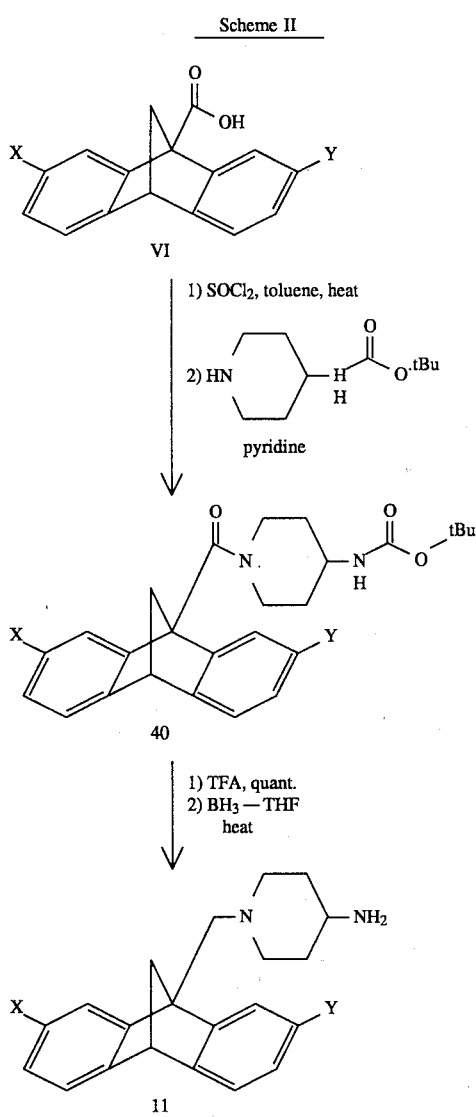

Scheme III

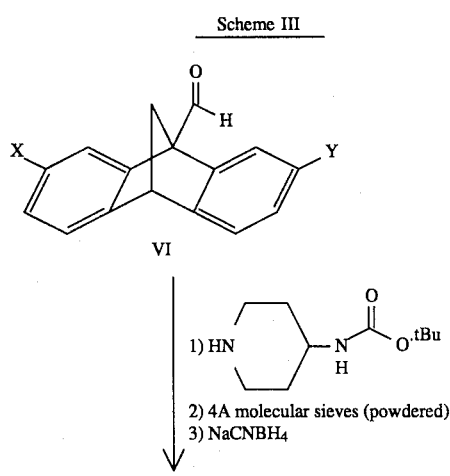

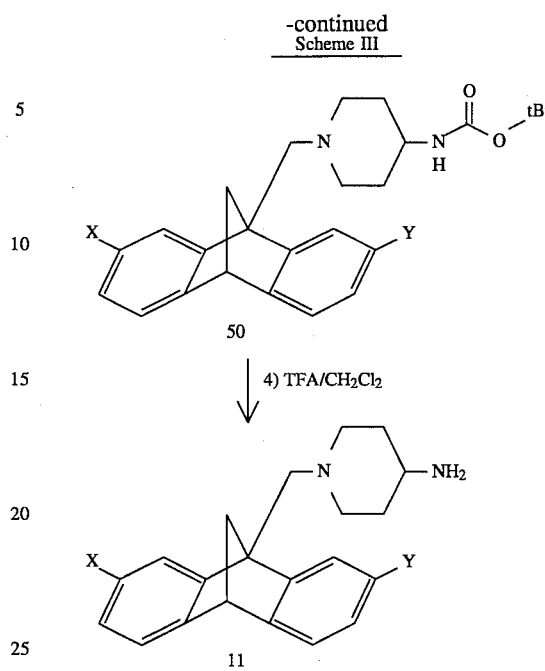

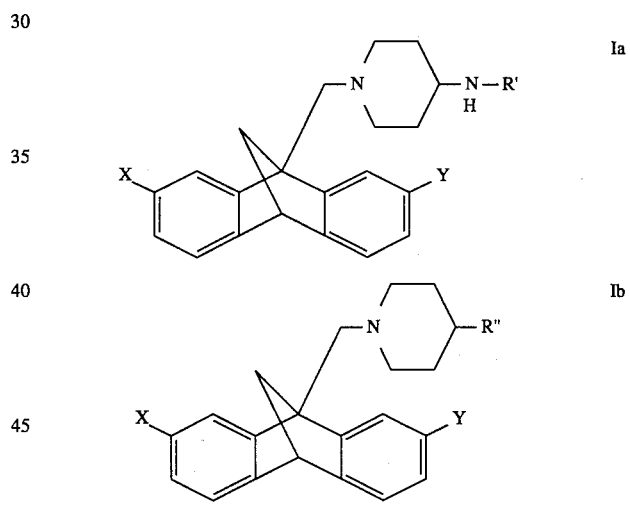

What is claimed is:

1. A compound having formula Ia or Ib or a pharmaceutically acceptable salt thereof, wherein:
X and Y are independently selected from hydrogen, halo and (1–6C)alkoxy;
R' is selected from
2-pyrimidinyl, which may be substituted with from 0–2 substituents selected from halo, phenyl, amino, (1–6C)alkoxy, hydroxy, nitro, and (1–6C)alkyl,
4-pyrimidinyl, 2-pyridyl, 2-purinyl; and
R" is 4-morpholinyl substituted by 0–2 substituents selected from (1–6C)alkyl.

2. A compound as defined in claim 1, wherein X and Y are independently selected from hydrogen and halo.

3. A compound as defined in claim 2, wherein X and Y are independently selected from hydrogen and chloro; R' is 2-pyrimidinyl; and R" is selected from trans-2,6-dimethyl- 4-morpholinyl and 4-morpholinyl.

4. A compound as defined in claim 3, wherein said compound is selected from:

1-(2-Chloro-9,10-dihydro-9,10-methanoanthracen-9-yl-methyl)-4-(trans-2,6-dimethyl-4 -morpholinyl)piperidine;

1-(2-Chloro-9,10-dihydro-9,10-methanoanthracen-9-yl-methyl)-4-(4-morpholinyl)piperidine dihydrochloride; and 2-[1-(9S,10S-2-Chloro-9,10-methanoanthracen-9-yl-methyl)-4-piperidylamino]pyrimidine.

5. A composition comprising a compound of formula Ia or Ib,

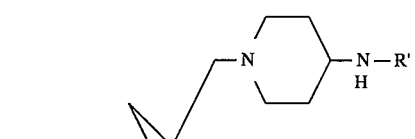

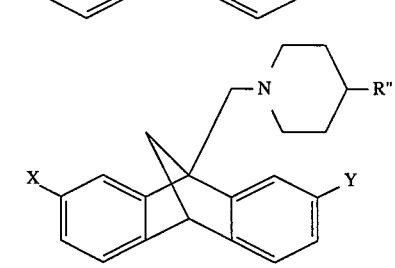

or a pharmaceutically acceptable salt thereof, wherein:

X and Y are independently selected from hydrogen, halo, and (1–6)alkoxy;

R' is selected from 2-pyrimidinyl, which may be substituted with from 0–2 substituents selected from halo, phenyl, amino, (1–6C)alkoxy, hydroxy, nitro, and (1–6C)alkyl, 4-pyrimidinyl, 2-pyridyl, 2-purinyl; and R" is 4-morpholinyl substituted by 0–2 substituents selected from (1–6C)alkyl and a pharmaceutically acceptable diluent or carrier.

6. A composition as claimed in claim 5, wherein X and Y are independently selected from hydrogen and halo.

7. A composition as defined in claim 6, wherein X and Y are independently selected from hydrogen and chloro; wherein R' is 2-pyrimidinyl; and R" is selected from trans-2,6-dimethyl-4-morpholinyl and 4-morpholinyl.

8. A composition as defined in claim 7, wherein said compound is selected from:

1-(2-Chloro-9,10-dihydro-9,10-methanoanthracen-9-yl-methyl)-4 -(trans-2,6-dimethyl-4-morpholinyl)piperidine;

1-(2-Chloro-9,10-dihydro-9,10-methanoanthracen-9-yl-methyl)-4-(4-morpholinyl)piperidine dihydrochloride; and 2-[1-(9S,10S-2-Chloro-9,10-dihydro-9,10-methanoanthracen-9-yl-methyl)-4 -piperidylamino]pyrimidine.

9. A method of treating neuropsychiatric disorders comprising administering to a person in need of such treatment an effective amount of a compound of formula Ia or Ib,

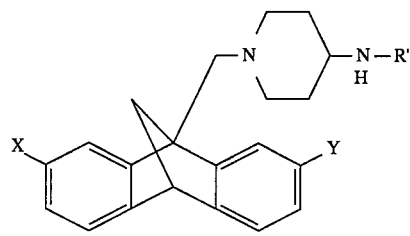

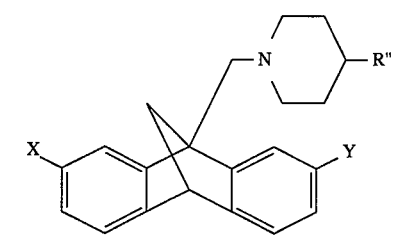

or a pharmaceutically acceptable salt thereof, wherein:

X and Y are independently selected from hydrogen, halo, and (1–6C)alkoxy;

R' is selected from 2-pyrimidinyl, which may be substituted with from 0–2 substituents selected from halo, phenyl, amino, (1–6C)alkoxy, hydroxy, nitro, and (1–6C)alkyl, 4-pyrimidinyl, 2-pyridyl, 2-purinyl; and R" is 4-morpholinyl substituted by 0–2 substituents selected from (1–6C)alkyl.

10. A method as defined in claim 9, wherein X and Y are selected from hydrogen and halo.

11. A method as defined in claim 10, wherein X and Y are independently selected from hydrogen and chloro; wherein R' is 2-pyrimidinyl; and R" is selected from trans-2,6-dimethyl-4-morpholinyl and 4-morpholinyl.

12. A method as defined in claim 11, wherein said compound is selected from:

1-(2-Chloro-9,10-dihydro-9,10-methanoanthracen-9-yl-methyl)-4 -(trans-2,6-dimethyl-4-morpholinyl)piperidine;

1-(2-Chloro-9,10-dihydro-9,10-methanoanthracen-9-yl-methyl)-4-(4-morpholinyl)piperidine dihydrochloride; and 2-[1-(9S,10S-2-Chloro-9,10-dihydro-9,10-methanoanthracen-9-yl-methyl)-4 -piperidylamino]pyrimidine.

13. A method as defined in claim 9, wherein said disorders are psychoses.

14. A compound of formula II,

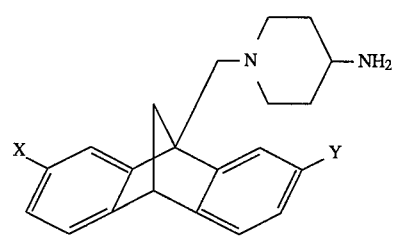

wherein X and Y are independently selected from hydrogen, halo, and (1–6C)alkoxy.

15. A compound of formula III,
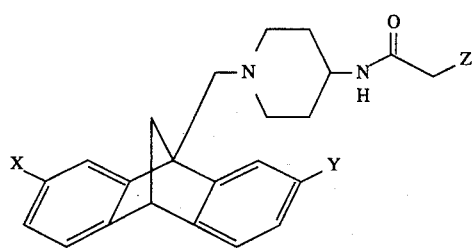
wherein X and Y are independently selected from hydrogen, halo, and (1–6C)alkoxy and Z is a halo group.
16. A compound of formula IX,
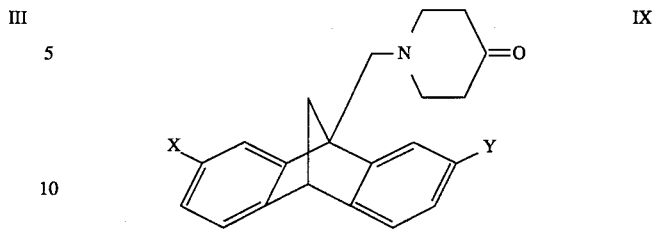
wherein X and Y are independently selected from hydrogen, halo, and (1–6C)alkoxy.
* * * * *